(12) United States Patent
Park

(10) Patent No.: US 10,139,807 B2
(45) Date of Patent: Nov. 27, 2018

(54) METHOD FOR CREATING A CUSTOMIZED ARTHROPLASTY RESECTION GUIDE UTILIZING TWO-DIMENSIONAL IMAGING

(71) Applicant: Somersault Orthopedics Inc., Pleasanton, CA (US)

(72) Inventor: Ilwhan Park, Walnut Creek, CA (US)

(73) Assignee: Somersault Orthopedics Inc., Pleasanton, CA (US)

( * ) Notice: Subject to any disclaimer, the term of this patent is extended or adjusted under 35 U.S.C. 154(b) by 573 days.

(21) Appl. No.: 14/820,473

(22) Filed: Aug. 6, 2015

(65) Prior Publication Data

US 2016/0038245 A1    Feb. 11, 2016

Related U.S. Application Data

(60) Provisional application No. 62/034,085, filed on Aug. 6, 2014.

(51) Int. Cl.
| | |
|---|---|
| *A61F 2/46* | (2006.01) |
| *G05B 19/4097* | (2006.01) |
| *A61B 34/10* | (2016.01) |
| *A61B 17/15* | (2006.01) |

(52) U.S. Cl.
CPC ........ *G05B 19/4097* (2013.01); *A61B 17/155* (2013.01); *A61B 17/157* (2013.01); *A61B 34/10* (2016.02); *A61B 2034/108* (2016.02); *G05B 2219/34165* (2013.01); *G05B 2219/45145* (2013.01)

(58) Field of Classification Search
CPC combination set(s) only.
See application file for complete search history.

(56) References Cited

U.S. PATENT DOCUMENTS

2009/0138020 A1*  5/2009  Park ................ A61B 5/055
                                                    606/88

* cited by examiner

*Primary Examiner* — Sameh Boles
(74) *Attorney, Agent, or Firm* — Stephen E. Zweig

(57) ABSTRACT

Aspects of the present disclosure involve systems, methods, computer program products for customized arthroplasty cutting guides or jigs. In particular, the present disclosure provides for a method of creating a customized arthroplasty cutting jig from one or more two-dimensional (2D) images of the patient's joint. The method includes receiving the 2D images of the joint from an imaging device, reformatting the images, and creating a customized jig template from the images. One or more landmarks are electronically marked on one or more of the series of 2D images of the patient's joint through a computing device. Once the template for the cutting jig is created utilizing one or more of the electronic markers on the 2D images, a cutting or milling program is generated by the computing device that may then be provided to a milling machine to create the cutting jig corresponding to the milling program.

10 Claims, 88 Drawing Sheets

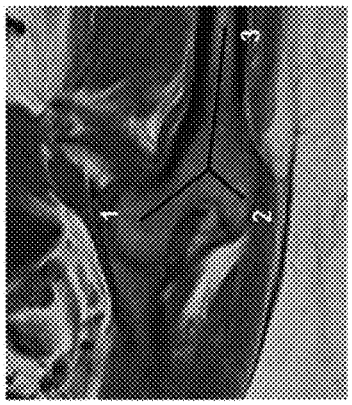
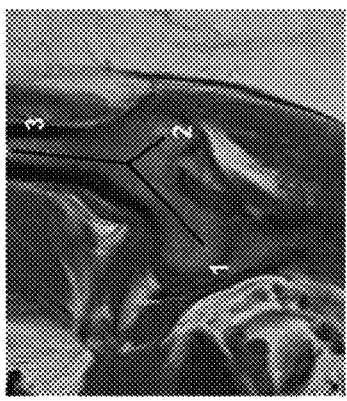
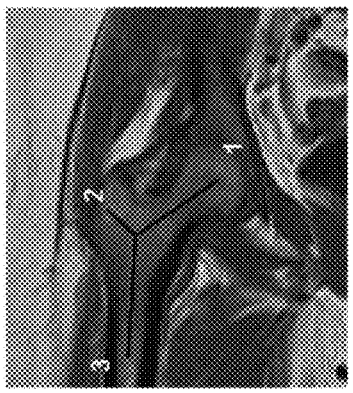
FIG. 9

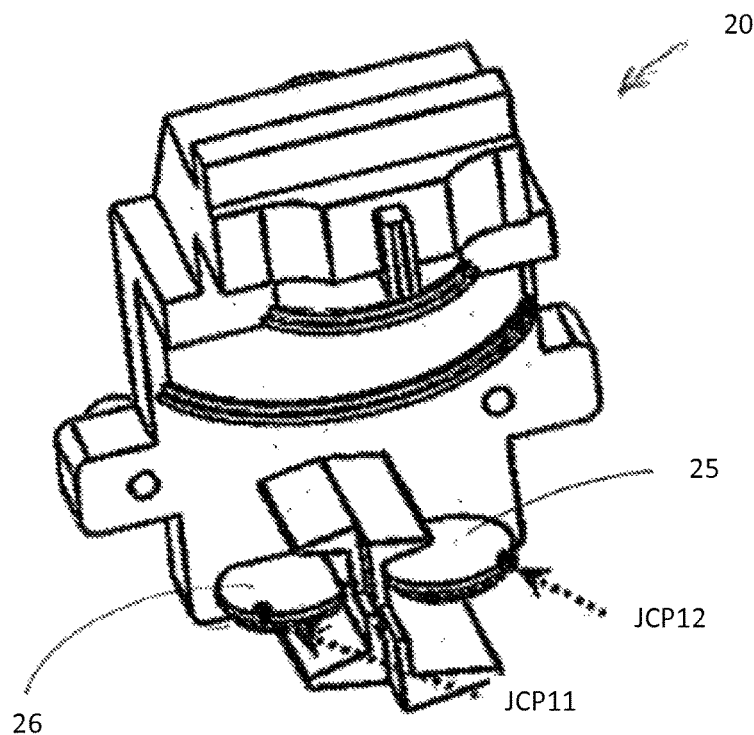
Fig. 1010A
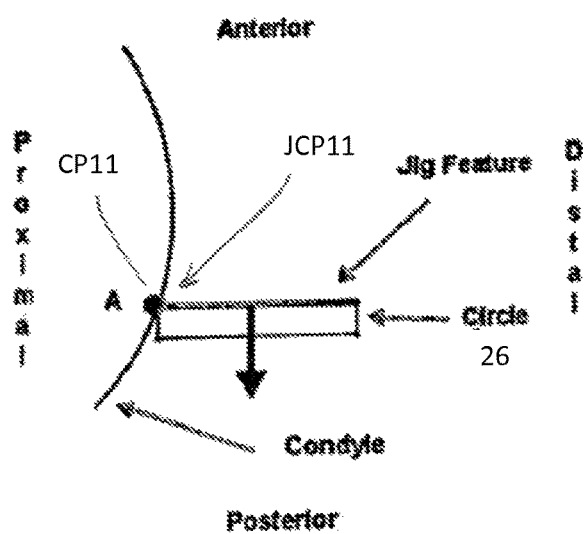
Fig. 1010B

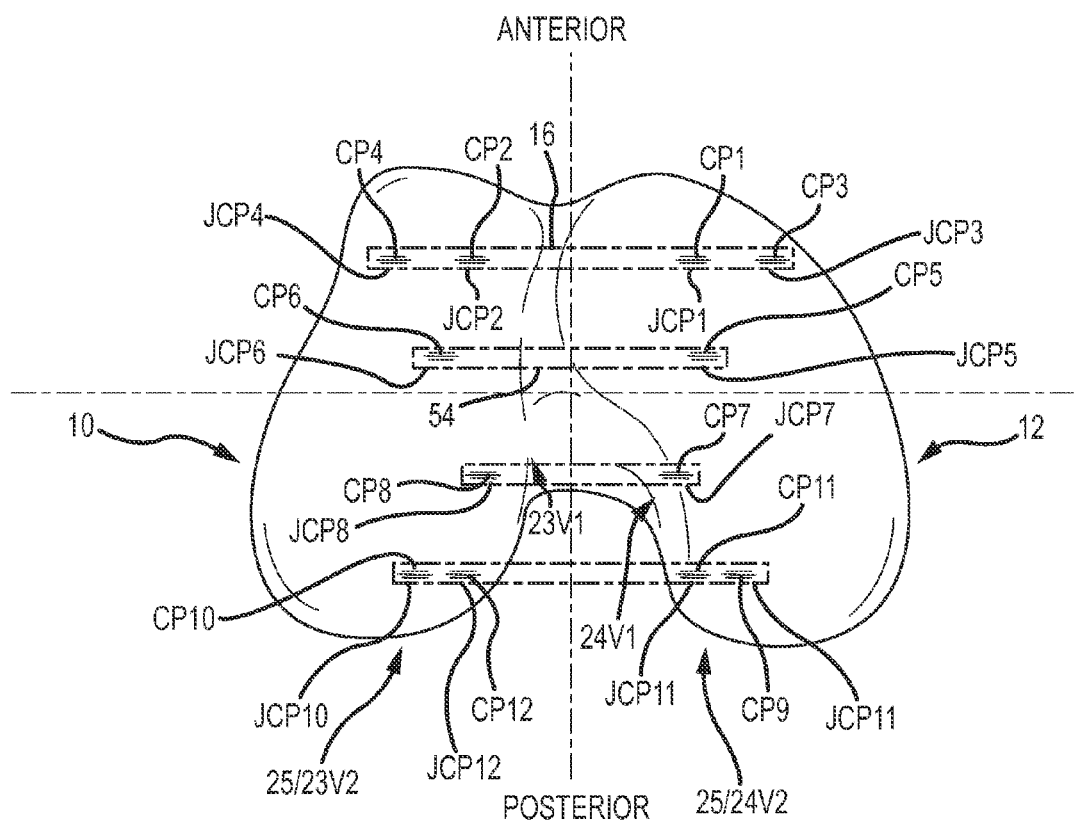
FIG. 1011

METHOD FOR CREATING A CUSTOMIZED ARTHROPLASTY RESECTION GUIDE UTILIZING TWO-DIMENSIONAL IMAGING

RELATED APPLICATIONS

This application claims priority under 35 U.S.C. § 119 from U.S. provisional application No. 62/034,085 entitled "METHOD FOR CREATING A CUSTOMIZED ARTHROPLASTY RESECTION GUIDE UTILIZING TWO-DIMENSIONAL IMAGING," filed on Aug. 6, 2014, the entire contents of which are fully incorporated by reference herein for all purposes.

TECHNICAL FIELD

Aspects of the present disclosure generally relate to systems and methods for creating and manufacturing customized arthroplasty cutting or resection guides for joint replacement procedures. More specifically, the present disclosure relates to methods for creating arthroplasty cutting guides customized to a particular patient from one or more two-dimensional images of a patient's joint taken from an imaging device.

BACKGROUND

Through over-use, traumatic events and/or debilitating disease, a person's joint may become damaged to the point that the joint is repaired. One type of procedure to address damage to a person's joint is an arthroplasty procedure. Arthroplasty is a medical procedure where a joint of a patient is replaced, remodeled, or realigned, often done to relieve pain in the joint after damage. Damage to the joint may result in a reduction or wearing away of cartilage in the joint area, which operates to provide frictional, compressive, shear, and tensile cushioning within the joint. As such, reduction in cartilage in a joint causes pain and decreased mobility of the joint. To combat this joint pain, a patient may undergo the arthroplasty procedure to restore function and use back to the damaged joint.

One type of arthroplasty procedure is known as Total Knee Arthroplasty (TKA). In general, TKA involves replacing the diseased or damaged portion of the knee with metal or plastic components that are shaped to approximate the shape of the replaced portion or shaped to allow movement of the joint and relieve the joint pain. Thus, a TKA procedure may include replacement of a portion of the femur and a portion of the tibia that make up the knee joint. Similar procedures may be performed on other damaged joints, such as a hip, a shoulder, an elbow, and the like. General discussion of arthroplasty procedures herein are directed specifically to TKA-type procedures, but may be applied to arthroplasty procedures of other types of joints.

In a TKA procedure, a damaged portion of the distal region of the femur is removed and replaced with a metal or plastic component that is shaped to mirror or approximate the replaced portion. The metal or plastic component may be impacted onto the femur or fixed using a type of surgical cement or other fastening system. Further, a proximal portion of the tibia may also be removed and replaced with a generally flat metal or plastic component that is shaped to mirror or approximate the replaced portion. The tibia replacement implant may also be attached to the tibia through impaction onto the bone or fixed using a type of cement. In general, the femur implant and the tibia implant are mated to form a joint that approximates the shape and operation of the knee joint. In some examples, a plastic surface is placed between the femur implant and the tibia implant to prevent metal-on-metal interaction between the implants during use of the replaced joint.

As mentioned above, a TKA procedure often involves the removal and replacement of portions of the femur and/or tibia of the injured knee. During the removal, the portions of the femur and tibia may be cut, drilled, resurfaced, and the like to create a surface on the bones that mates with the respective implants. In one particular example, the ends of the bones (distal end of the femur and proximate end of the tibia) may be completely removed to create a generally flat surface to which the implants are mated. Once the mating surfaces for the implants are created on the receiving bones, the implants may then be attached to the bones as described above.

Although the broad outline of the TKA procedures is described above, there is much to consider when performing the procedure. For example, patients may undergo a preoperative planning phase of the procedure through one or more consultations with a doctor that could last a month or more before the TKA is performed. In addition, alignment of the implants in the joint with the rest of the patient's anatomy is crucial to the longevity of the implant and the implant's effectiveness in counteracting the pre-TKA joint condition. As such, systems and methods have been developed to produce customized arthroplasty cutting jigs that allow a surgeon to quickly and accurately perform the necessary resections of the bones that result in a successful TKA procedure. In particular, cutting jigs may be generally customized for the particular patient's joint undergoing the TKA procedure to ensure that the implants align with the patient's anatomy post-procedure. Through the use of such customized cutting jigs, the TKA procedure is both more accurate (ensuring more longevity to the implants) and quicker (reducing the time required for the surgical procedure, thereby reducing the potential for post-surgery complications).

In general, cutting guides or cutting jigs used in TKA procedures may attach to one or more bones of the knee and provide a cut line to the surgeon for use during the TKA surgery. In particular, a femur cutting jig may attach to the distal end of the femur and include a cut guide or line. A surgeon, during the procedure, inserts a saw device into or through the cut line to resect the distal end of the femur. Similarly, a tibia cutting jig may attach to the proximal end of the tibia and include a cut line that the surgeon uses to resect the proximal end of the tibia. In this manner, the ends of the femur and tibia are resected by the surgeon during the TKA procedure, thereby creating a smooth mating surface for the implants.

The cutting jigs used in the TKA procedure may attach to the bones of the knee in various ways. General cutting jigs (cutting jigs that do not incorporate customization to the particular patient's anatomy) may attach to the femur and tibia to provide the resection line for the surgeon. Such general cutting jigs often require the surgeon to align the cut line into the proper position during attachment of the cutting jig. As can be appreciated, such general cutting jigs result in vastly different quality of effectiveness, mostly based on the experience and skill of the surgeon. Customized cutting jigs, on the other hand, are designed to mate with the particular patient's femur and/or tibia to reduce the amount of incorrect attachment of the cutting jig to the patient's knee. Through the use of customized cutting jigs, surgeon error in TKA procedures may be greatly reduced.

The customization of the arthroplasty cutting jigs may vary from procedure to procedure. In one simple example, the customization may include merely selecting one jig from a group of generalized cutting jigs of various sizes in an attempt to match the size of the patient's anatomy. On the other end of the spectrum, the customized arthroplasty cutting jig may provide a mating surface that is the exact negative of the femur or tibia for attachment to the bone surface. Regardless of the customization of the cutting jig used, the jig should be designed to provide the proper location and orientation on the bones of the affected joint such that treatment of the region can be performed accurately, safely, and quickly.

Images of orthopedic joints that are candidates for partial or total replacement are often formed as MRI images, referred to here as "slices," with each such image being a projection on a two dimensional image forming substrate. Each such MRI image is actually a three dimensional "voxel," representing a thickness of approximately 2 mm of partial images of cortical bone, cancellous bone cartilage and open space, with each such material having its own range of grey scales in the MRI image. For a full three dimensional representation of an anatomical surface AS of interest, it is often necessary to provide tens to hundreds of MRI slices in two or more of three views (coronal or front view, axial or top view, and sagittal or side view) for a given anatomical component.

Many of the knee replacement procedures presently use what is characterized as "full segmentation" in order to represent a relevant portion of a femur or a tibia surface in three dimensions. This approach requires use of a dense, three dimensional grid of points to accurately represent a surface, especially a surface having cusps or sharp corners with very small associated radii of curvature. This approach has several disadvantages, including the following: (1) this approach is time consuming, often requiring 4-20 hours of intense numerical work to generate and check the accuracy of the grid point coordinates for a single surface; (2) because of the time required to implement this approach for a single surface, use of this approach in mass manufacturing of custom or semi-custom instruments is limited; (3) this approach may introduce geometrical errors, including closing errors; (4) because of the close spacing of grid points, polynomials of high mathematical degree are be used, which can introduce undesirable "ripples" in the mathematical surface produced by a full segmentation process; and (5) formation and analysis of a large number of MRI slices is required It is with these and other issues in mind that various aspects of the present disclosure were developed.

SUMMARY

One implementation of the present disclosure may take the form of a method for creating a cutting jig for an arthroplasty procedure. The method includes the operations of receiving a plurality of two-dimensional images of a patient's joint the subject of the arthroplasty procedure, reformatting the two-dimensional images to approximate a true anatomical coordinate of the patient's joint, and locating a plurality of mating shapes within the reformatted plurality of two-dimensional images of the patient's joint, the plurality of mating shapes corresponding to a plurality of mating shapes of a cutting jig for use during the arthroplasty procedure. The method may also include the operations of generating a milling program based at least on the placement of the mating shapes within the reformatted plurality of two-dimensional images of the patient's joint and milling the cutting jig based at least on the milling program.

Another implementation of the present disclosure may take the form of a system for creating a cutting jig for an arthroplasty procedure from a plurality of two-dimensional images. The system includes a network connection for receiving a plurality of two-dimensional images of a patient's joint the subject of the arthroplasty procedure, the plurality of two-dimensional images generated utilizing a magnetic-resonance imaging machine and a computing device. The computing device comprise at least one processing device and a non-transitory memory device in communication with the at least one processing device for storing one or more instructions that, when executed by the at least one processing device, cause the computing device to perform certain operations. Such operations may include reformatting at least a portion of the two-dimensional images to approximate a true anatomical coordinate of the patient's joint, locating a plurality of mating shapes within the reformatted plurality of two-dimensional images of the patient's joint, the plurality of mating shapes corresponding to a plurality of mating shapes of a cutting jig for use during the arthroplasty procedure, generating a milling program based at least on the placement of the mating shapes within the reformatted plurality of two-dimensional images of the patient's joint, and transmitting the generated milling program over the network connection to a milling device for milling the cutting jig based at least on the generated milling program.

BRIEF DESCRIPTION OF THE DRAWINGS

FIG. 9 is a screenshot of three orientations of a 2D image of a femoral head.

FIGS. 1010A-1010B are isometric and schematic views indicating suitable locations of FCJM contact points (11-12), according to an embodiment.

FIG. 1011 is an axial view of a distal femur illustrating jig contact points and femoral contact points, according to an embodiment.

DETAILED DESCRIPTION

Figure 1:
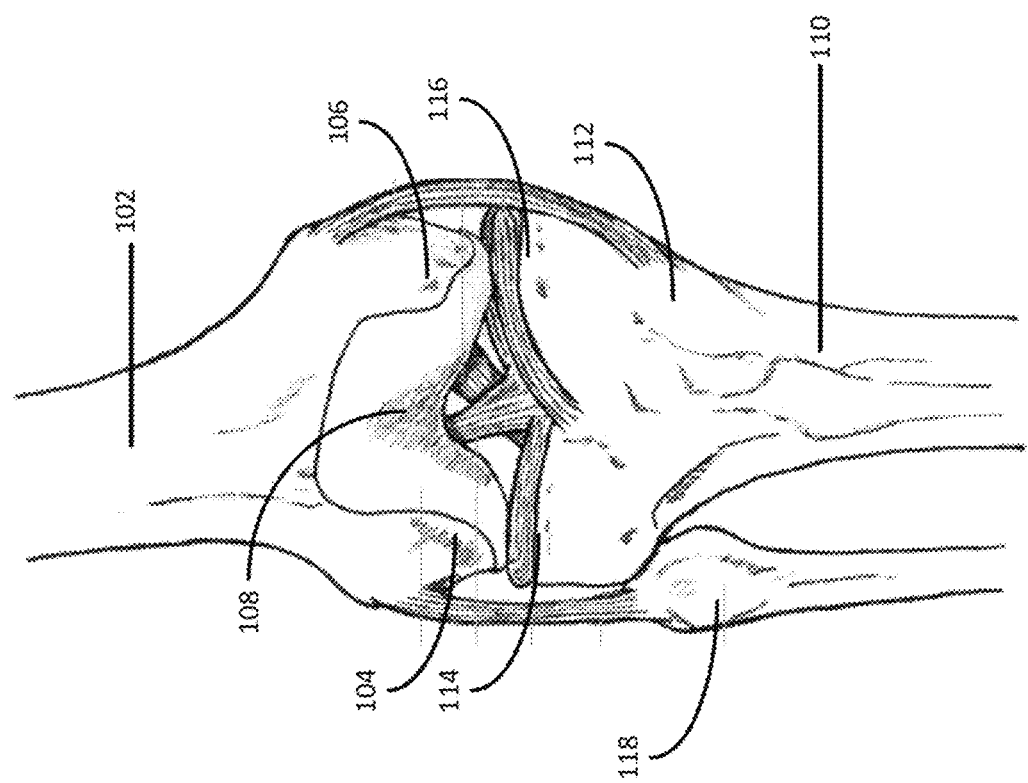
FIG. 1 is an anterior view of a knee joint illustrating the femur, tibia and ligaments of the joint.

Aspects of the present disclosure involve systems, methods, computer program products, manufacture process and the like, for customized arthroplasty cutting guides or jigs. In particular, the present disclosure provides for a method of creating a customized arthroplasty cutting jig from one or more two-dimensional (2D) images of the patient's joint to undergo the arthroplasty procedure. The method includes receiving the 2D images of the joint from an imaging device, reformatting the images, and creating a customized jig template from the images. In general, one or more landmarks are electronically marked on one or more of the series of 2D images of the patient's joint through a computing device. These electronic markers on the series of 2D images correspond to landmarks of the patient's joint undergoing the arthroplasty procedure. Once the template for the cutting jig is created by the computing device utilizing one or more of the electronic markers on the 2D images, a cutting or milling program is generated by the computing device. The cutting or milling program may then be provided to a milling machine to create the cutting jig corresponding to the milling program. The cutting jig is thus customized to the landmarks identified in the series of 2D images of the patient's joint. Further, the procedure does not require the generation of a three-dimensional (3D) model of the patient's anatomy to create the customized nature of the cutting jig. Rather, by utilizing one or more mating shapes that contact the joint anatomy at particular contact points of the joint anatomy corresponding to the identified landmarks in the 2D images, the customization of the cutting jig is achieved. Further, because the procedure does not require the generation of a 3D model, the customized cutting jigs may be produced more quickly and efficiently than previous customization methods.

To aid in the description below of the customized arthroplasty cutting jigs and methods for creating said jigs, a brief discussion of the bone anatomy of the human knee is now included. As mentioned above, the present disclosure may be applied to any type of joint of a patient. However, for ease of understanding, the discussion herein is limited to particulars of the human knee as an example of the joint relating to the present disclosure procedure and apparatus.

Further, would be desirable to eliminate the full segmentation process and the associated three dimensional anatomical modeling of a femur surface, and to replace this approach with data obtained from relatively few MRI "slices," as few as, for example, six two-dimensional slices, that permits flexibility in choice of contact points between the femur surface and the instrument (jig) that facilitates resectioning and removal of a portion of the knee component. It would be even more desirable to replace the full segmentation procedure, with its thousands of grid points, with a simpler, quicker procedure that works with as few as about twelve contact points between an anatomical surface, such as the posterior femur, and a resectioning mechanism, such as a jig that properly positions a cutting guide. In regards to the tibia, would be desirable to eliminate the full segmentation process and the associated three dimensional anatomical modeling of a tibia surface, among other things; and to replace this approach with data obtained from relatively few MRI "slices," as few as five, for example, two-dimensional slices, that permits flexibility in choice of contact points between the tibia surface and the instrument (jig) that facilitates resectioning and removal of a portion of the knee component. It would also be desirable to replace the full segmentation procedure, with its thousands of grid points, with a simpler, quicker procedure that works with as few as about seven contact points between the anatomical surface and resectioning mechanism for the tibia component. Aspects of the present disclosure may involve a "sparse contact" approach that provides a cutting jig mechanism, which defines a cut plane for a tibia component of a knee.

Aspects of the present disclosure involve a "sparse contact" approach that provides a cutting jig mechanism, which provides a cut plane for a femur 6 component of a knee 8. A lower (distal) portion of the femur component, illustrated in FIGS. 1A and 1B for a right knee, includes a lateral condyle (LC) 10 and an adjacent medial condyle (MC) 12, which together define a trochlear groove (TG) 14 that is positioned between the lateral and medial condyles, and extends from the anterior of the respective condyles posteriorly to the intercondylar fossa 16 between the posterior of each respective condyle. Each condyle is of generally convex shape with the intersection between the condyles forming the trochlear groove being concave. The remainder of the femur is positioned above the lateral and medial condyles.

Figure 101A:
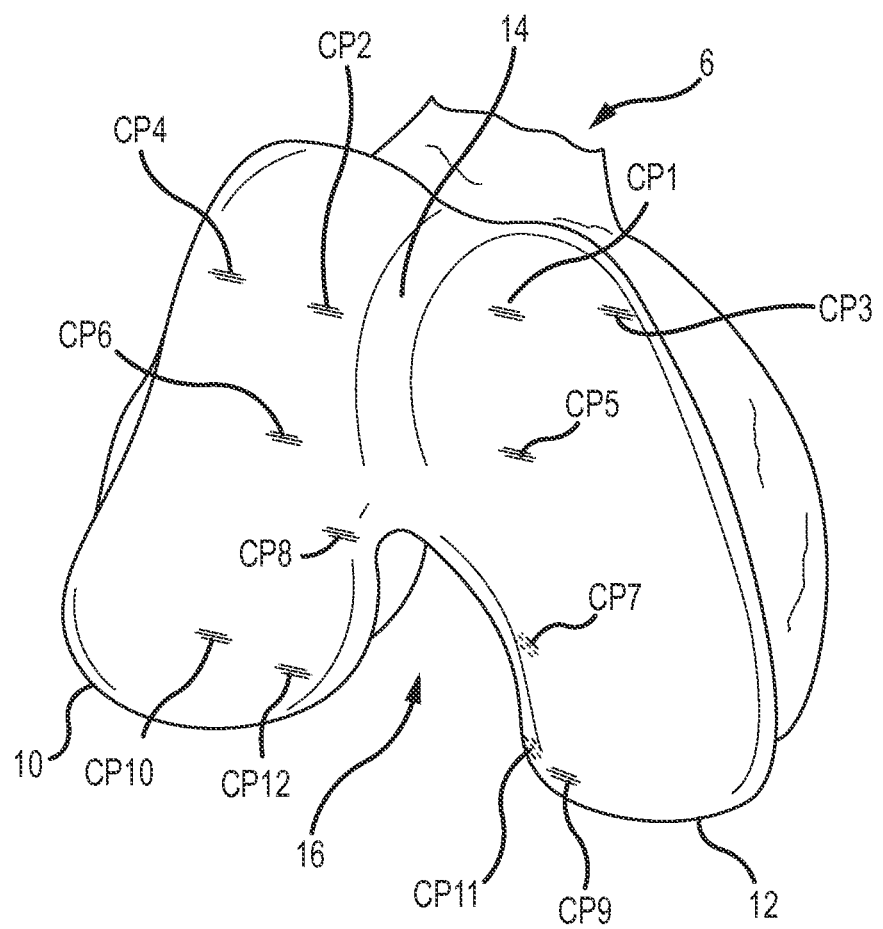
FIG. 101A is a representative isometric view of a lower portion of a femur (right knee), indicating contact points for a fibia cutting jig mechanism (FCJM) in one embodiment.
Figure 101B:
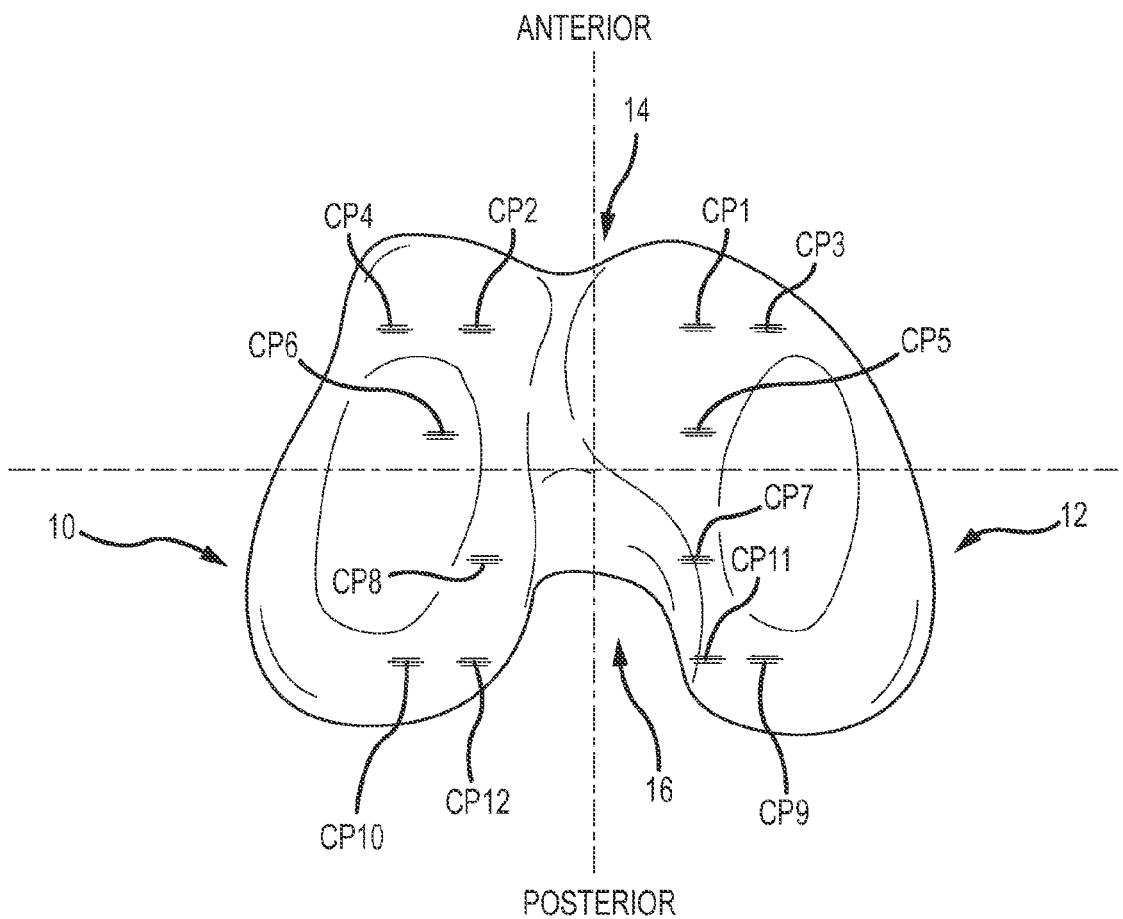
FIG. 101B is a representative top view of the lower portion of the femur as shown in FIG. 101A.
Figure 102A:
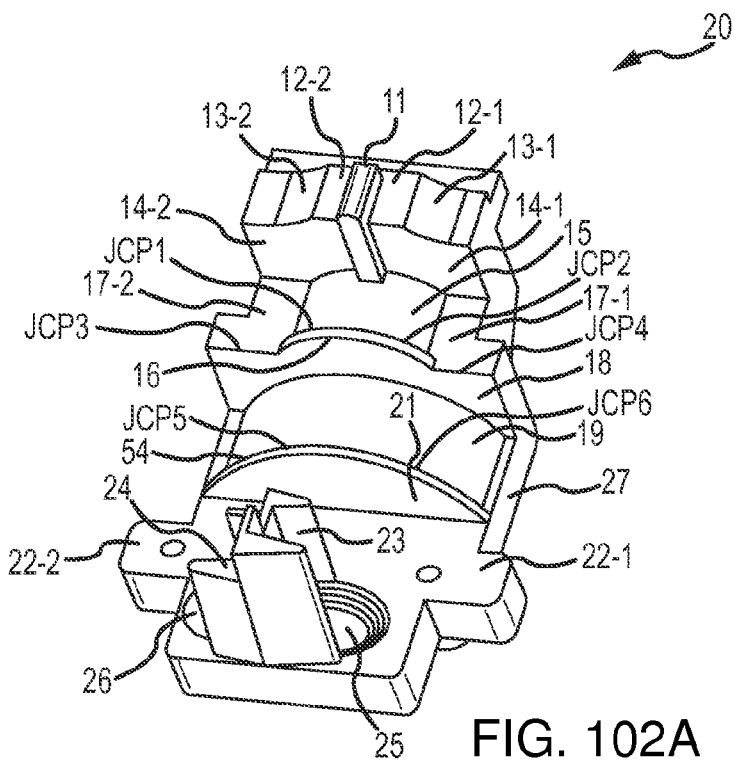
FIGS. 102A and 102B are isometric views of a femur cutting jig mechanism, indicating contact points that correspond to the contact points indicated in FIG. 101A, in one embodiment.
Figure 102B:
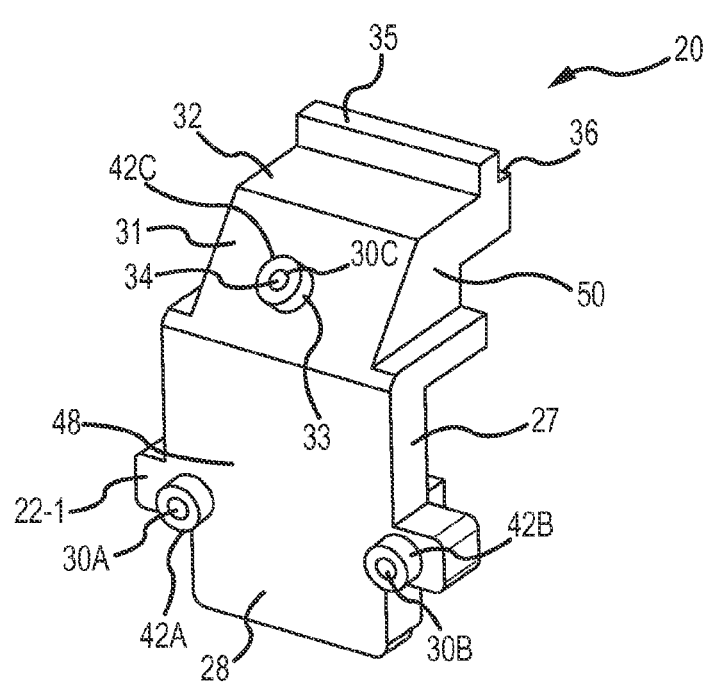

A femur cutting jig mechanism (FCJM or "jig") 20, illustrated in isometric views in FIGS. 102A and 102B and in FIGS. 103A-103E with the jig positioned on or relative to the femur 6, has a first number N1 of jig contact points (JCPs) that make contact with a small number of corresponding femoral contact points (CPs in FIGS. 101A and 101B) on the trochlear groove surface 14 of the femur, and/or on the respective condyles to either side and adjacent to the trochlear groove, and make contact with a second number N2 of contact points on the lateral condyle 10 and on the medial condyle 12, where the sum, N1+N2, may be about 12, and can be made smaller in some approaches. The number, N1+N2, of contact points and their placement on the femur surfaces is chosen so that, where each jig contact point makes contact with a corresponding contact point on the femur surface, the jig is stably positioned on the femur surface and resists any longitudinal, transverse, and/or rotational forces of modest magnitude that would otherwise move the jig. In this way, a surgeon may position the jig onto the femoral surface and when the various contact points are positioned and mildly pressed on the femur, the jig resists various forces that would cause it to move so long as some mild force is maintained to hold the jig in place. The jig may then be pinned to the femur and used to mount a cutting guide on the femur. When the jig contact points are properly positioned, the jig seats on the femur in accordance with a cut plane. When the femur is resected along the cut plane, a prosthetic may be placed on the femur in accordance with a determined prosthetic knee alignment.

Figure 103A:
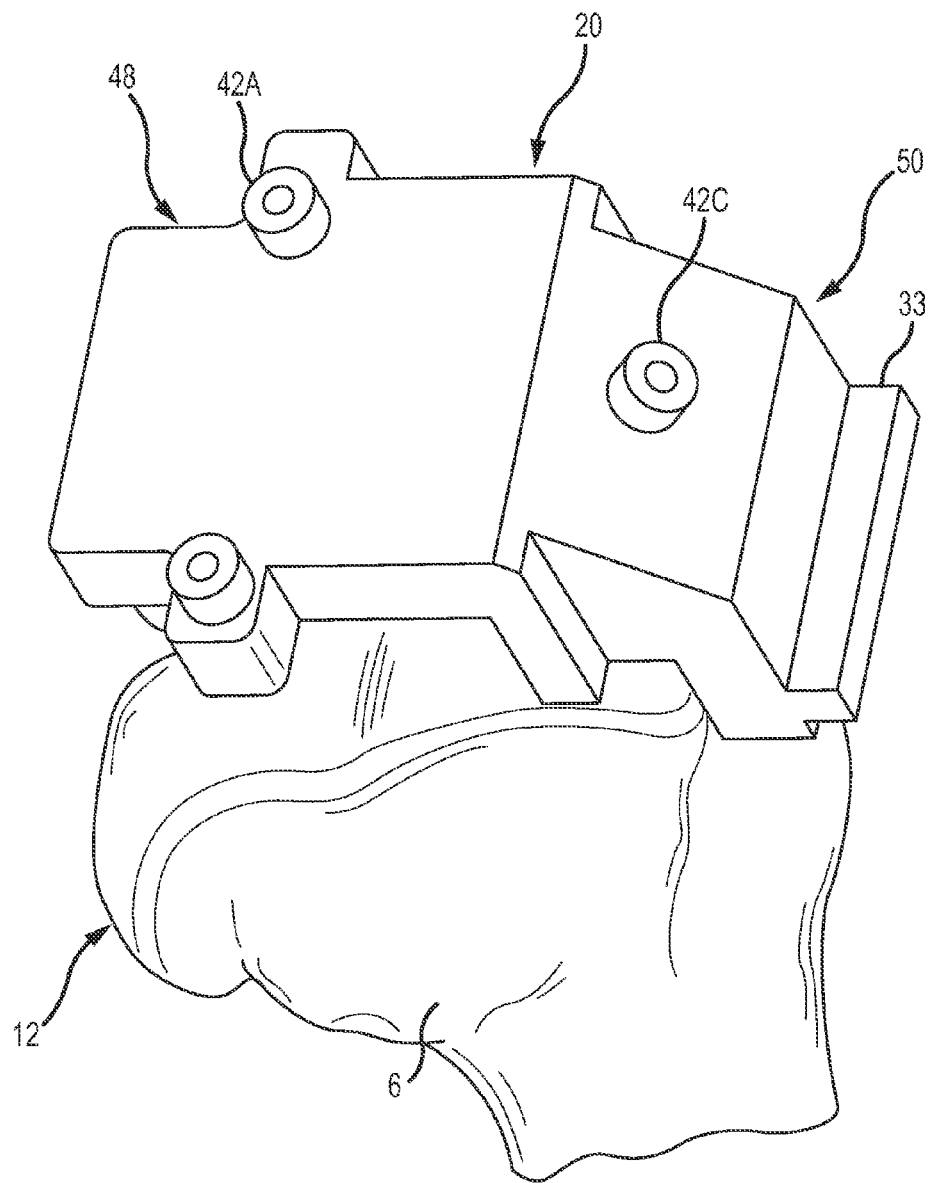
FIGS. 103A, 103B, and 103C illustrate various isometric views of one example of a FCJM on a distal region of a femur.
Figure 103B:
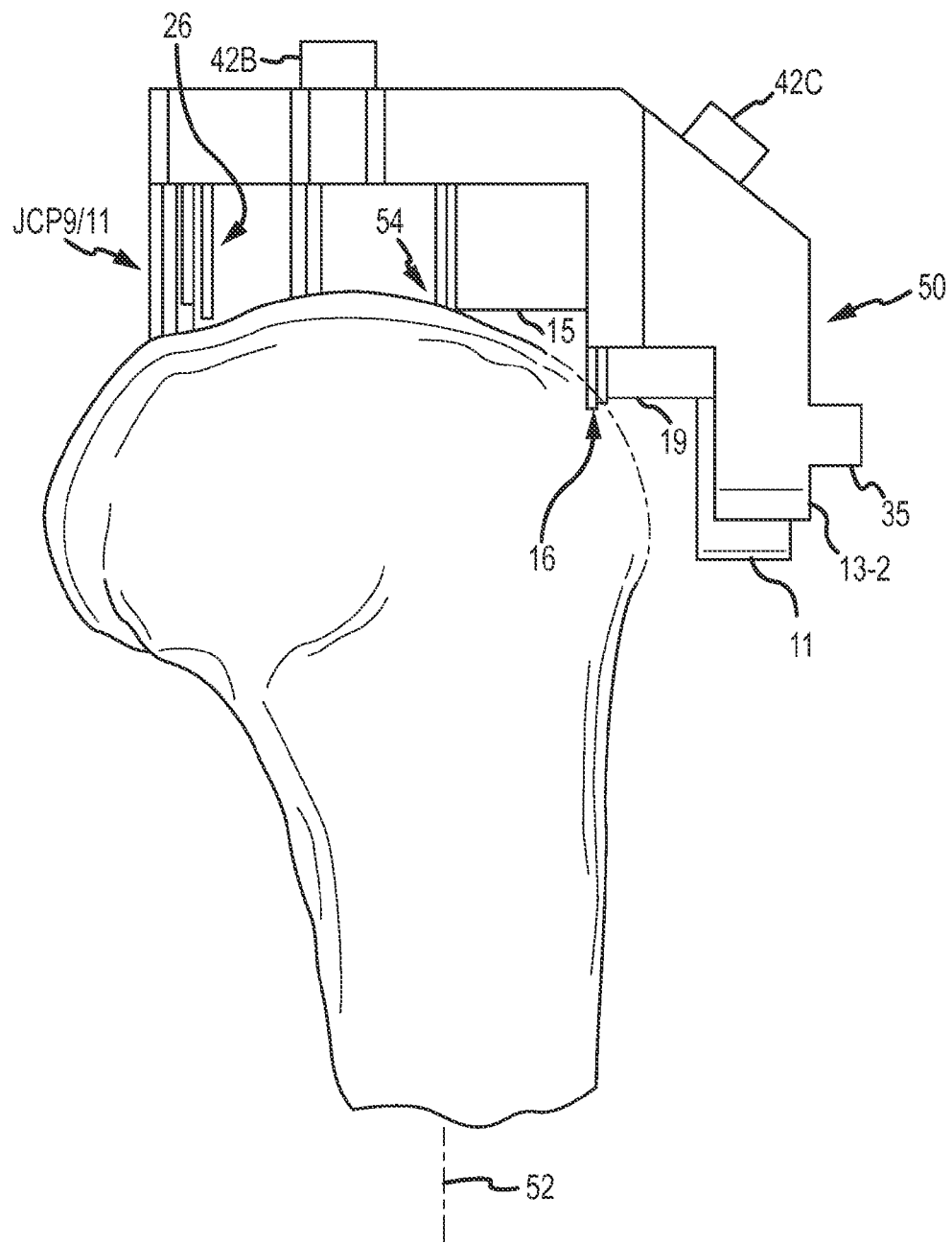
Figure 103C:
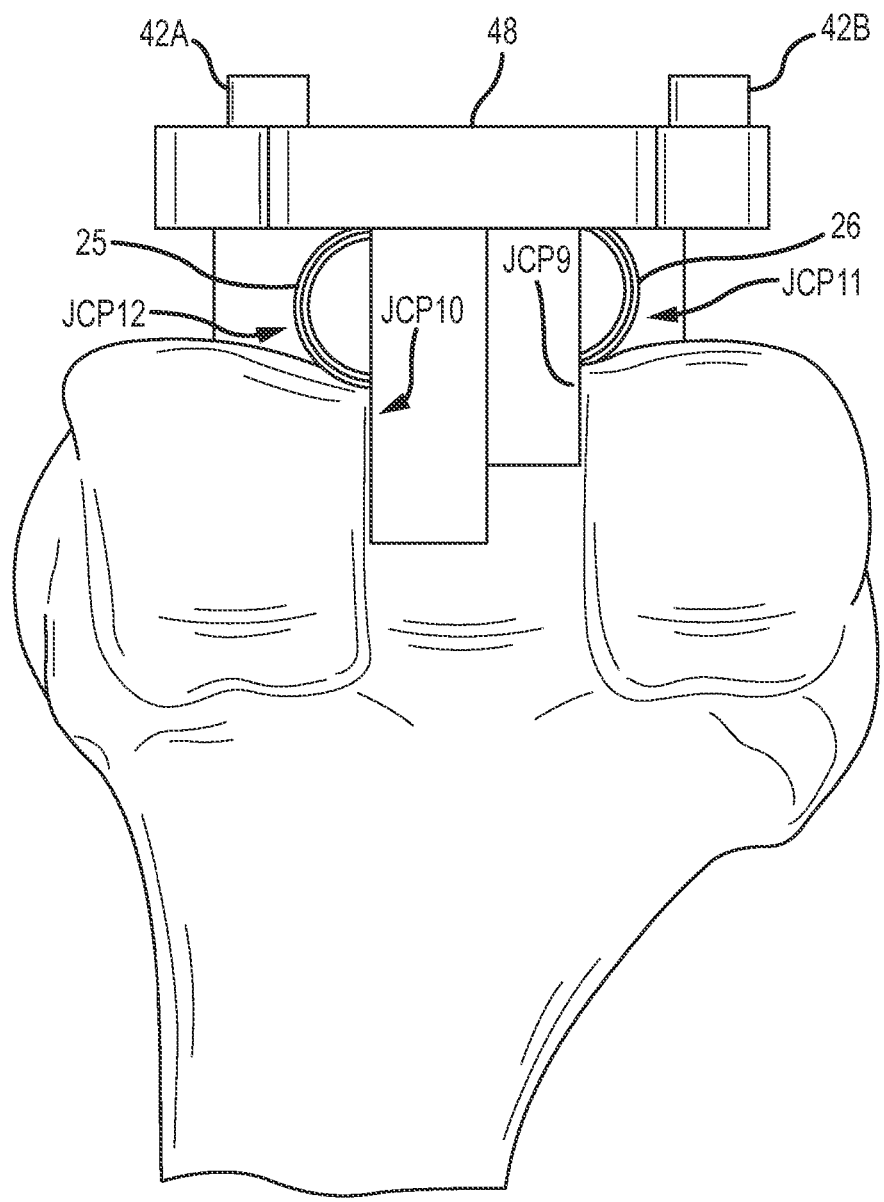
Figure 103D:
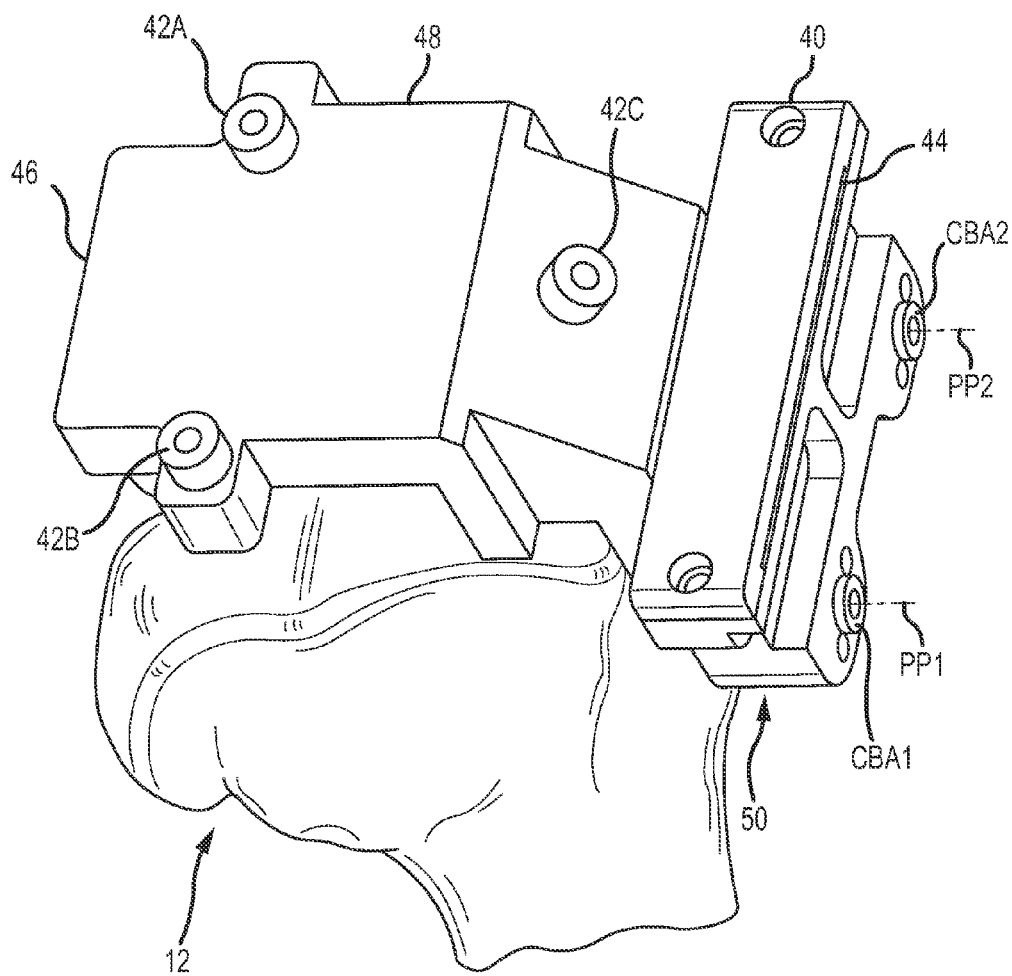
FIG. 103D illustrates an axial isometric view of the FCJM on the distal region of the femur, with a cut plane bar coupled with a mounting flange of the FCJM.
Figure 103E:
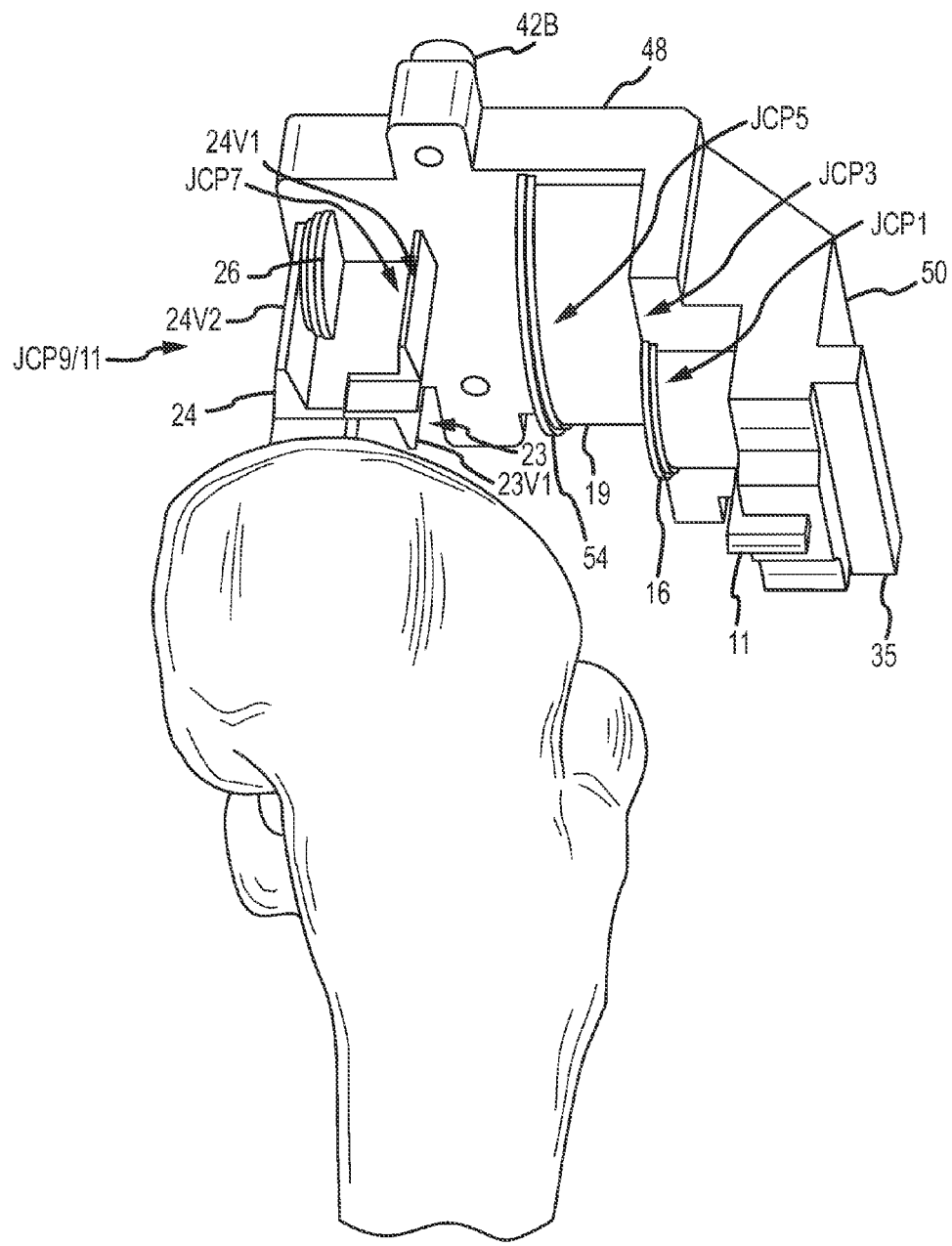
FIG. 103E illustrates the jig positioned above the femur prior to placement thereon.

Referring to FIGS. 103A-103E, more particularly, the jig 20 and a corresponding cut plane guide 40 (FIG. 103D) are positioned in contact with the condyles 10, 12 of the femur, and with the trochlear groove 14. FIGS. 103A-103E illustrate the jig slightly above and not fully in contact with the femur. The jig, once positioned correctly, is pinned to the femur by inserting three pins (not shown) through three corresponding bosses 42A, 42B, 42C projecting from the jig and defining apertures 30A, 30B, 30C through which the pins are inserted. It may be necessary to predrill the femur prior to placement of the pins. The cut plane bar is mounted to a mounting flange 35, and is pinned to the femur through two cut bar positioning apertures, CBA1 and CBA2, shown in FIG. 103D and defined in the cut plane guide 40. To secure the CPG, a surgeon drills into a portion of cortical bone, using CBA1 and CBA2 as guides. Two positioning pins, PP1 and PP2, are inserted into the apertures, CBA1 and CBA2, and into the drilled out portion of the cortical bone. Referring to FIG. 103B, the surgeon may then remove the jig by removing the three jig pins, and rotating the mounting flange 35 away from the cut plane guide and then withdrawing the jig away from the femur, leaving the guide in place. The jig, when mounted on the femur, pre-positions the mounting flange and the cut plane guide. The cut plane guide defines a slot (or channel) 44 positioned so that a bone saw may be guided to resection and remove a lower portion of the patient's femur, for replacement of the knee. After resectioning has occurred, the guide is removed and optionally can be reused in replacement of another patient's knee.

The "sparse contact" approach described herein relies on a small number (e.g., six or fewer) of spaced apart two-dimensional MRI images or "slices" of the femur anatomical surface, with each slice containing or illuminating one, two, or possibly more contact points between the femur anatomical surface and the jig 20 that helps define a cut plane position for resectioning and removing a portion of the femur. Using this approach, more than one jig contact point may be defined for a slice so that some jig contact points may be co-planar relative to the MRI slice and or relative to each other. The approaches discussed herein may have several advantages, including but not limited to: (1) the number of MRI slices actually formed and used is quite small (e.g., about 6) and represents about 5-10 percent of the total volume of the portion of the anatomy component of interest; (2) the number of contact points and associated coordinates needed for position stability of the jig is also small (e.g., about 12 or less, as compared with hundreds to thousands for a full segmentation approach); (3) the "design time" required to determine relevant component dimensions and coordinates of the contact points on the anatomical surface is estimated to be no more than 20 minutes and should decrease further as one accumulates experience in the dimensioning process; (4) it is anticipated that this "sparse contact" approach will permit semi-custom design and fabrication of the replacement components and associated tools; and/or (5) provides some flexibility for the orthopedic surgeon to exercise creativity and compensation in choices and modifications of some of the dimensions and angular orientations.

A femoral cutting jig 20 conforming with various aspects of the present disclosure includes a substrate 46 from which various jig contact points (JCPm) project, are otherwise supported or defined. In one possible implementation, the jig is a unified structure formed from a block of base material using a computer numerical control (CNC) machine. However, it is possible for the jig to be an assembly of various components that form the final cutting jig structure. Alternatively, the jig may be created through molding, machining, milling, forming, 3D printing, assembling, or other processes. The term "substrate" as used herein is meant to refer to a base structure upon which the various jig contact points and jig contact point supporting structures are provided or otherwise supported, and by which the relative positioning of the various jig contact points are maintained. As mentioned, the jig may be a unified structure and hence the substrate and jig contact points are formed from the same material and thus the relative positioning of the jig contact points is naturally maintained. Other processes, such as milling a base material or forming a jig in a mold, would provide a similar unified structure. It is not necessary, however, that the jig be unified structure in which case the substrate may be a frame or other structure or assembly on which various jig contact point defining structures are attached or otherwise associated.

The jig contact points are arranged and spaced such that a surgeon may press the jig onto the distal surface of the femur at the knee and the jig will be properly positioned when the jig contact points are seated on respective femoral contact points (CPm). Notably, there are a discrete number of jig contact points (e.g., 9-14) as opposed to full surfaces or far more numerous numbers of contact locations. The jig also includes a cutting guide support structure onto which may be mounted the cutting guide 40. When the jig is seated on the femur, the jig may be pinned to the femur to properly position the cutting guide so that a resection of the femur may be performed pursuant to a total knee replacement.

In regards to the tibia, a proximal, upper portion, of a tibia component 10, illustrated in FIGS. 201A and 201B for a right knee, a tibia table 11 having one or two concave surfaces 12, 13, a tibial spine 14 and intercondylar tubercles 14A, 14B separating these surfaces as a tibia top surface, having a tibia shank 15 that extends below the top surface, and having a fibula 16 for stability that extends roughly parallel to the tibia shank. Interest focuses here on the tibia top surface and on an upper portion of the tibia shank A tibia cutting jig mechanism (TCJM) or simply "jig" 20, illustrated in isometric views in FIGS. 202A and 202B, and in FIGS. 203A-203F showing the jig positioned on or relative to a tibia, has a number (N) of jig contact points (JCP) that make contact with the same number of corresponding points on and adjacent to the top surface of the tibia 10 (FIGS. 201A and 201B), where the number N is as few as seven (7) and may be slightly smaller or slightly larger in some embodiments. The number N used here may be compared with a corresponding number used in the prior art full segmentation approach, which typically involves hundreds to several thousand contacts for a tibia component. The number N used here depends, in part, on placement of the jig contact points on the jig 20 and on placement of the corresponding contact points on the proximal surface of the tibia. The contact points help stabilize the jig 20, even in the small number proposed, against longitudinal, transverse and/or rotational movement relative to the tibia top surface when the jig and the tibia top surface are in contact. For example, when a surgeon is moving the jig onto the tibia in order to secure a cut plane guide 31 CPG (FIG. 3D) to the top area of the tibia, in order to resect the tibia before applying a prosthetic as part of a total knee replacement, it is important for the jig to be stably positioned on the tibia prior to pinning.

The jig 20 is positioned in contact with the top surface of the tibia 10 and oriented to properly position the cut plane guide 31. The jig, once positioned correctly, is pinned to the tibia by inserting three pins (not shown) through three corresponding bosses (33-1, 33-2, 33-3) projecting from the jig and defining apertures through which the pins are inserted. It may be necessary to predrill the femur, possibly using the bosses or drill guides, prior to placement of the pins. The cut plane guide 33 is mounted between two projections 30-1 and 30-2. The guide 31 is pinned to the tibia through two cut bar positioning apertures, CBA1 and CBA2, shown in FIG. 3D and defined in the cut plane guide. Two positioning pins securing the bar may be drilled into a portion of cortical bone (tibia below the tibial plateau) of the patient, taking care not to extend drilling of either of the apertures, CBA1 and CBA2. The jig 20 is then removed, leaving the guide 31 in place to provide a guide for resectioning and removal of an upper portion of the patient's tibia, for replacement of this component of the knee. As illustrated, the guide 31 defines a saw slot 35 that may receive and guide a bone saw for the resectioning procedure. After resectioning has occurred, the cut plane guide is removed and optionally can be reused in replacement of another patient's knee.

The "sparse contact" approach discussed here relies on a small number (e.g., five or fewer) of two dimensional MRI images or "slices" of the tibia, with each slice containing or illuminating one or two contact points between the anatomical surface (tibia) and the tibia cutting jig mechanism that helps define a cut plane position for resectioning and removing a portion of part of the tibial area of interest. This approach has one or more advantages: (1) the number of MRI slices used to identify femoral contact points for corresponding jig contact points is quite small (e.g., at most about five) and represents no more than about 5-10 percent of the total volume of the portion of the anatomy component of interest; (2) the number of contact points and associated coordinates needed for position stability of the jig is also small (e.g., at most about seven, as compared with hundreds to thousands for a full segmentation approach); (3) the "design time" required to determine relevant component dimensions and coordinates of the contact points on the anatomical surfaces of the tibia is estimated to be about 20 minutes and is expected to decrease further as one accumulates experience in the dimensioning process; (4) this "sparse contact" approach will permit semi-custom design and fabrication of the knee replacement components and associated tools; and (5) this approach provides some flexibility for the orthopedic surgeon to exercise creativity and compensation in choices and modifications of some of the dimensions.

FIG. 1 illustrates an anterior view of a patient knee joint, and in particular, the femur, tibia, and ligaments of the knee. The femur is proximal the tibia and includes two eminences, known as the condyles 104,106. Between the condyles is a smooth depression called the trochlea 108 or trochlear groove. The condyles are divided into a medial condyle 104 and a lateral condyle 106. The tibia 110 includes a head with two tuberosities, a medial tuberosity 114 and a lateral tuberosity 116. The medial 114 and lateral tuberosity 116 generally form concave surfaces (known as the tibia plateau) in the head 112 of the tibia 110. In general, the condyles 104,106 form two convex surfaces that engage and articulate with two convex surfaces of the tuberosities 114,116 of the tibia 110 during operation of the knee joint. A fibula bone 118 is also shown in FIG. 1 that attaches to the tibia 110 at or near the tibia head 112. Additional features and details of the femur 102 and the tibia 110 of the knee joint are discussed in more detail below with reference to FIGS. 2 through 5.

Figure 2A:
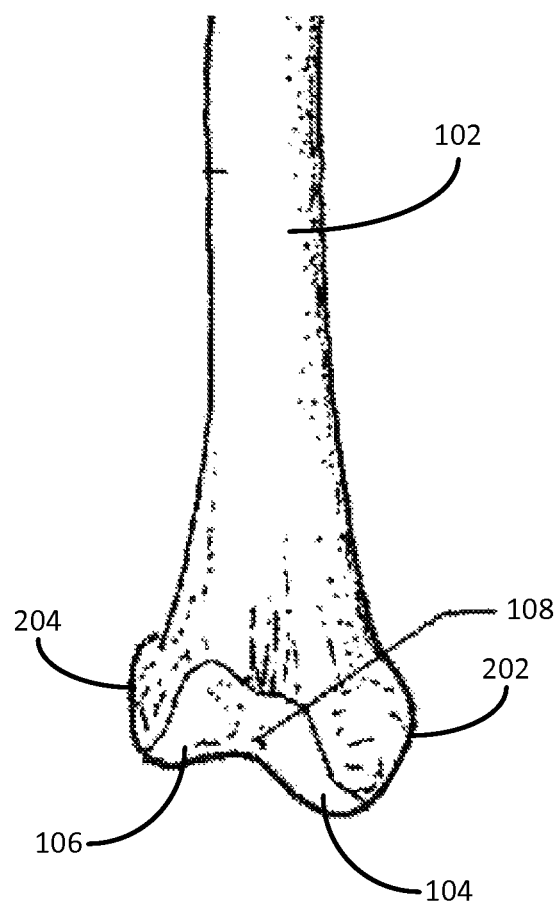
FIG. 2A is an anterior view of a lower femur.

FIG. 2A is an anterior view of the lower or distal end of the femur illustrating the portions of the femur associated with the knee joint. Thus, similar to the discussion above with reference to FIG. 1, the femur 102 includes a medial condyle 104 and a lateral condyle 106. Between the condyles is the trochlea 108. The outer surface of the medial condyle 104 is a small eminence known as the outer or medial tuberosity 202 which provides an attachment area for external lateral ligaments of the knee. Similarly, the outer surface (with reference to the center of the bone) of the lateral condyle 106 is an eminence known as the inner or lateral tuberosity 204 which provides an attachment area for the internal lateral ligaments.

Figure 2B:
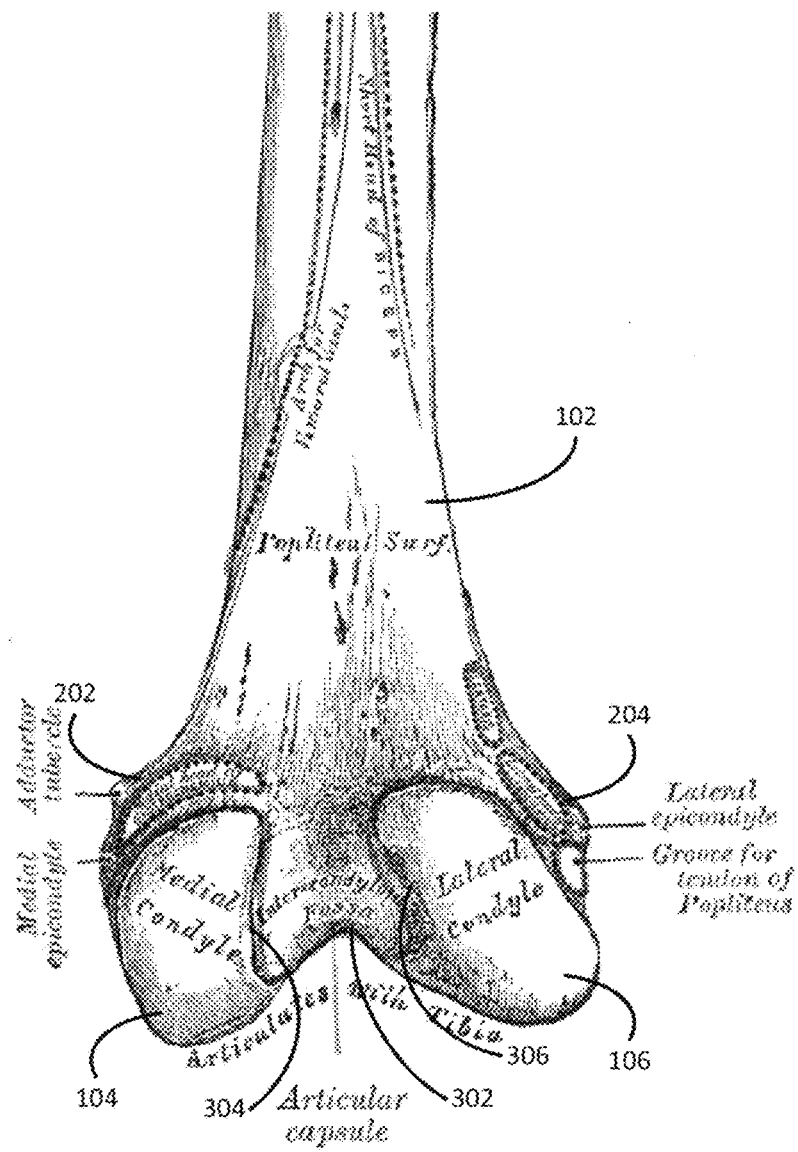
FIG. 2B is a posterior view of a lower femur.

Turning now to the posterior view of the lower femur illustrated in FIG. 2B, the posterior views of the medial condyle 104 and the lateral condyle 106 are shown. Between the condyles 104,106 of the posterior portion of the femur 102 lies a notch known as the intercondyloid notch 302. In particular, the inner surfaces 304, 306 of the posterior portions of the medial condyle 104 and the lateral condyle 106 form the surfaces of the intercondyloid notch 302. Also shown in FIG. 3 is the posterior view of the medial tuberosity 202 and the lateral tuberosity 204 along the outer surfaces of the medial condyle 104 and the lateral condyle 106, respectively.

Figure 3A:
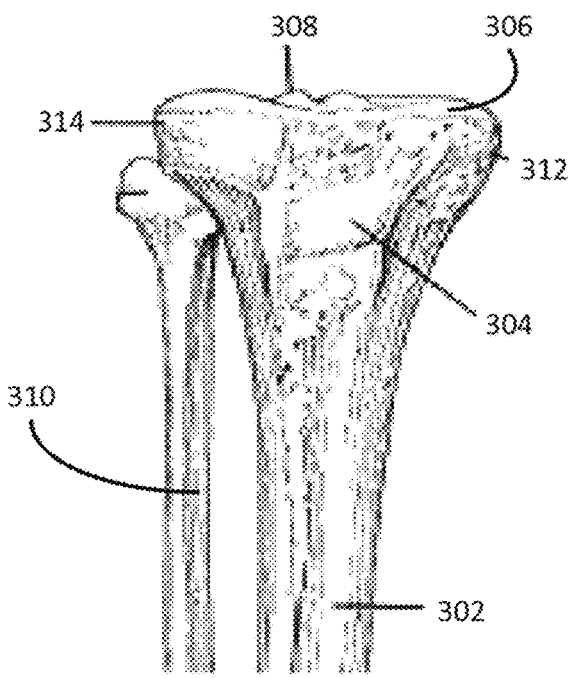
FIG. 3A is an anterior view of an upper tibia.
Figure 3B:
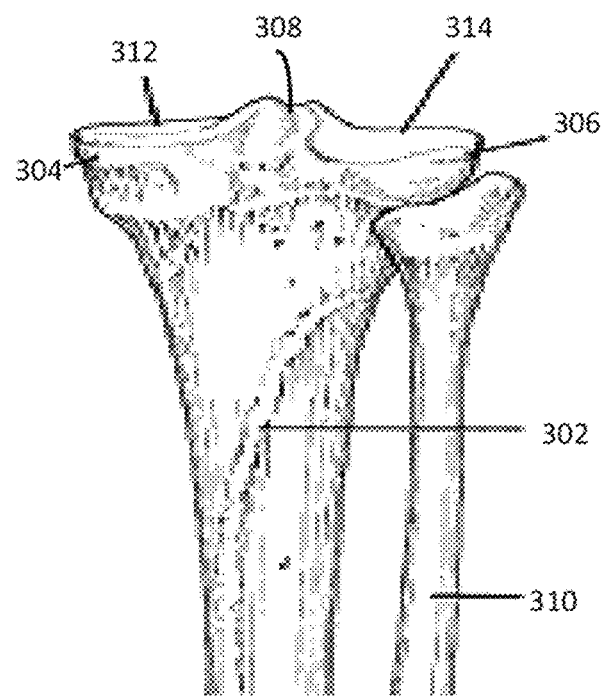
FIG. 3B is a posterior view of an upper tibia.

FIG. 3A is an anterior view of the upper or proximal tibia and FIG. 3B is a posterior view of the upper tibia. The proximal end of the tibia generally includes a tibia shaft 302 and a tibia head 304. The tibia head 304 forms a plateau surface 306 at the proximal end of the tibia. The plateau surface 306 includes a spine feature 308 that runs down the middle of the plateau surface. Attached to the tibia head 304 is the fibula 310. The tibia head 304 also includes a lateral condyle 312 and a medial condyle 314 that correspond to and articulate with the condyles of the femur, described above.

Figure 4:
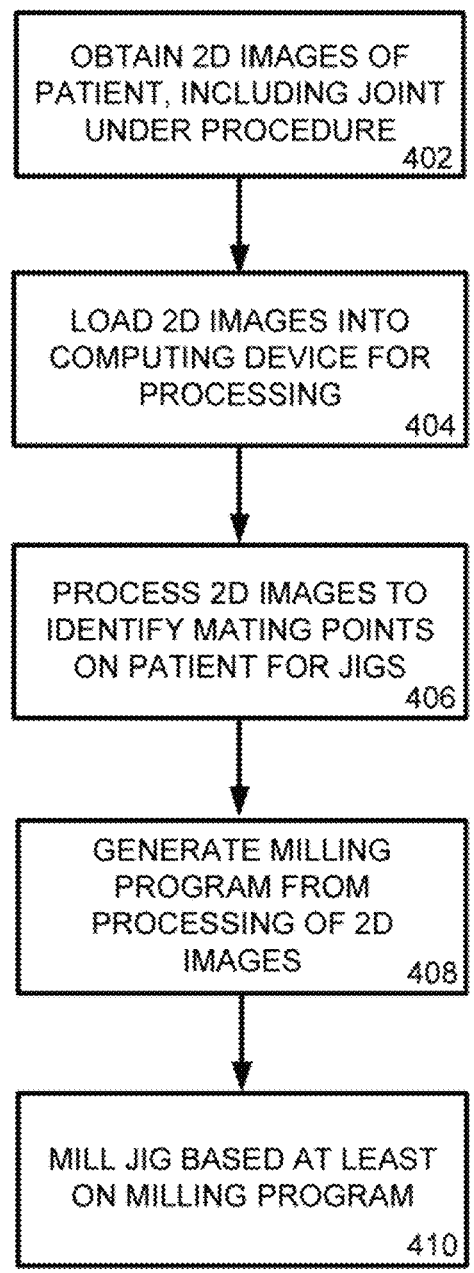
FIG. 4 is a flowchart illustrating a method to create a customized arthroplasty cutting jig from one or more two-dimensional images of a patient's joint.

In general, during a TKA procedure, portions of the distal end of the femur (such as that shown in FIGS. 2 and 3) and the proximal end of the tibia (such as that shown in FIGS. 3A and 3B) are removed by the surgeon and replaced with an implant that approximates the shape and function of the ends of the respective bones. To aid in resecting portions of the femur and tibia, the surgeon may employ a femur cutting jig and tibia cutting jig that provides a cut or resection line for the surgeon to cut along. In some instances, the femur and tibia cutting jigs may be customized to fit onto the particular patient's bones of the knee. One method for creating a customized cutting jig for an arthroplasty procedure (such as a TKA) is illustrated in the flow chart of FIG. 4. In particular, the method described in FIG. 4 provides for creating a cutting jig that is customized to the patient's anatomy from 2D images of the patient's joint. Although more or fewer operations may be included in the process to generate a customized arthroplasty cutting jig, the operations of FIG. 4 provide a general outline of one such process that utilizes 2D images of the patient's joint.

Figure 5:
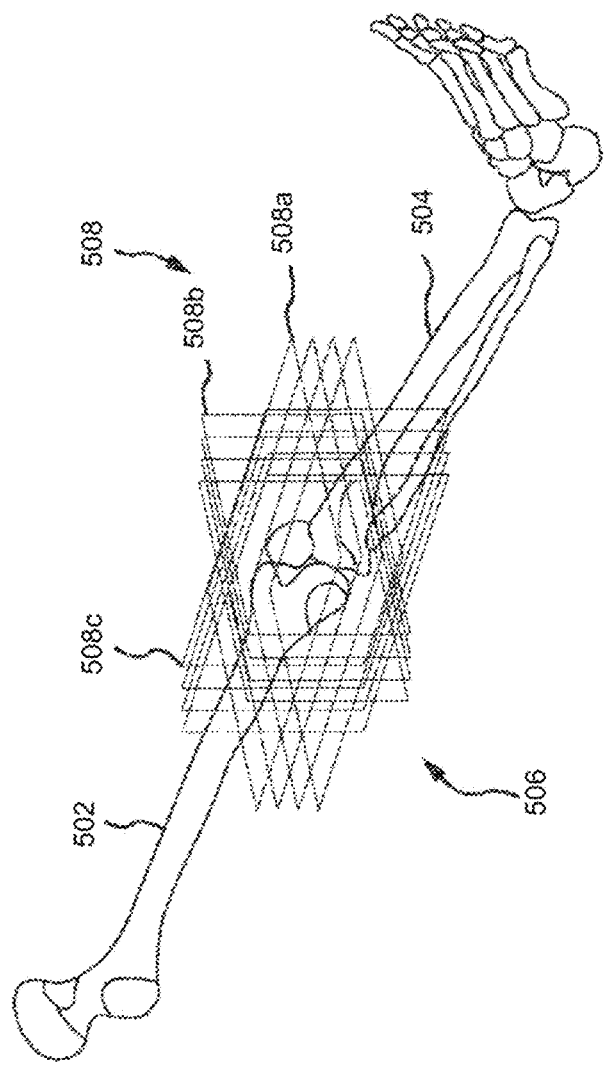
FIG. 5 is an illustration of one embodiment for obtaining 2D images of a knee of a patient.

Beginning in operation 402, a series of two-dimensional (2D) images of the patient's joint on which the arthroplasty procedure is to be performed may be obtained or received through a network connection. The 2D images of the patient's joint may be obtained from an imaging device (such as an X-ray or magnetic resonance imaging (MRI) machine) from several aspects of the joint. For example, FIG. 5 illustrates one embodiment for obtaining 2D images of a knee 506 of a patient. In particular, the patient's knee 506, including portions of the femur 502 and tibia 504, is scanned in a MRI knee coil to generate a plurality of 2D knee coil MRI images of the patient's knee. In one embodiment, the 2D images 508 of the knee include a plurality of images taken along a coronal plane 508a through the knee, a plurality of images taken along an axial plane 508b through the knee, and/or a plurality of images taken along a sagittal plane 508c through the knee. In other embodiments, the 2D images may be any combination of coronal, sagittal and/or axial views. In one embodiment, the MRI imaging spacing for the 2D knee coil images may range from approximately 2 mm to approximately 6 mm and may vary from aspect to aspect. For example, the coronal image slices 508a may be spaced 2 mm apart, while the axial image slices 508b may be spaced 6 mm apart.

While the embodiments herein are discussed in the context of the imaging being via an MRI machine, in other embodiments the imaging is via computed tomography (CT), X-ray, or other medical imaging methods and systems. Further, although it is discussed herein as a scan of the knee, the 2D images may be obtained for any joint or other area of the patient's body, such as images of the patient's ankle, hip, shoulder, etc. For example and as explained in more detail below, imaging of the patient's hip and ankle may also be utilized in the development of customized cutting jigs for TKA procedures.

Once the 2D images of the joint at issue are obtained, the images may be entered into a computing device for processing and to further the procedure through which the arthroplasty cutting jig is created in operation 404. The computing device may receive the images through any form of electronic communication with the imaging device. In one particular example, the 2D images may be obtained by the imaging device (such as the MRI imaging machine) and transmitted to a website accessible by the computing device. In general, however, the 2D images may be obtained from the imaging machine in any fashion for further processing by the computing device. Once received, the 2D images may be stored in a computer-readable medium for further processing by the computing device.

In operation 406, the 2D images of the joint are processed to reformat the images to convert the images from a machine-defined coordinate system to approximate a true anatomical coordinate system for the images and/or to identify one or more points or landmarks associated with the patient's joint that mate with contact points or surfaces of the customized cutting jig. In general, a true anatomical coordinate of the patient's joint corresponds to the natural alignment of the patient prior to damage to the joint. For example, true anatomical alignment of the patient's knee may correspond to an axial plane through the center of the knee parallel to the ground while the patient is walking. It should be appreciated, however, that reformatting the 2D images to achieve an image that is a true anatomical alignment of the knee is not required. Rather, the reformatting of the images may approximate images of true anatomical alignment of the knee. The images that illustrate the joint at a true anatomical coordinate system may be used for jig creation and to aid a surgeon in approving the jig placement in the damaged joint.

In one embodiment, an operator of the computing device may sit at a monitor or other interface of the computing device through which the images are viewed. Utilizing a software program executed by the computing device, the operator may view the 2D images and provide one or more electronic markers on at least one of the 2D images. These electronic markers may correspond to one or more reference points within the images for processing and reformatting of the images by the computing device and/or identify features or landmarks within the 2D images of the patient's anatomy that correspond to contact surfaces of the customized cutting jig. The operations to create the reference points and features of the customized cutting jig are described in more detail below.

In another embodiment, a program executed by the computing device may obtain the 2D images, determine the one or more reference points within the images, reformat the images to correspond to a true anatomical coordinate system, and/or identify the landmarks within the 2D images that correspond to contact surfaces of the customized cutting jig, with or without the aid of an operator of the computing device. In yet another embodiment, one or more of these operations are performed by the operator, while other operations are performed by the computer program. As such, any of the operations and methods described herein may be performed by an operator of the computing device or the computing device itself through hardware, software, or a combination of both hardware and software. The particular operations and considerations of operation 406 are discussed in more detail below with reference to FIGS. 7-45.

With the various electronic markers identified on the 2D image(s), the computing device may generate a program or computational information based on the electronic markers in operation 408. This computational information may be provided to a milling device, such as a computer numerical control (CNC) milling device in operation 410, to create the customized cutting jig for the arthroplasty procedure based at least on the computational information provided to the milling device. In general, a CNC machine or device is operated by programmed commands included in a program or list of commands to mill or create an apparatus based on the instructions provided in the commands. Thus, in this example, CNC milling machines translate the commands into control signals of a cutting device to mill a jig out of a jig blank according to the provided information. As pertaining to the method of FIG. 4, the computational information generated by the computing device associated with the electronic markers in the 2D images are utilized to generate the series of commands to operate the CNC milling machine. Thus, a customized arthroplasty cutting jig is created by providing the milling or cutting program that includes information concerning the electronic markers in the 2D images and a jig or guide blank to the CNC machine so that the machine mills or otherwise creates the customized jig based on the instructions of the milling program. In this manner, 2D images of a joint may be utilized to create a customized arthroplasty cutting jig for use in arthroplasty procedures to restore function and use to the joint of a patient.

Figure 6:
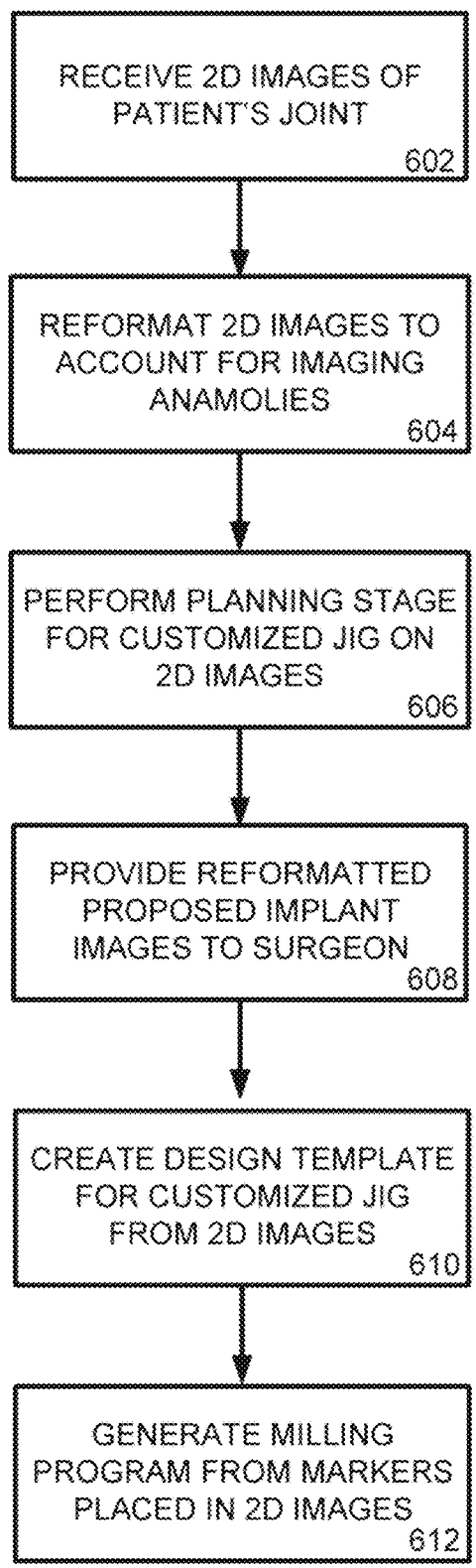
FIG. 6 is a flowchart illustrating a method for creating a milling or cutting program to provide to a milling machine to create a customized arthroplasty cutting guide for use in an arthroplasty procedure.

FIG. 6 is a flowchart illustrating a method for creating a milling or cutting program to provide to a CNC machine (or the like) to create a customized arthroplasty cutting jig for use in an arthroplasty procedure. In general, the operations of the flowchart of FIG. 6 are performed by an operator of a computing device, the computing device itself, or a combination of the operator and the computing device. Also, the operations are a further description of operation 406 discussed above with reference to FIG. 4.

In one embodiment, the operations described below may be performed multiple times for the different bones that make up a particular joint. For example, in a TKA procedure, the operations of FIG. 6 may be performed for images of the patient's femur as well as for images of the patient's tibia. For a hip replacement procedure, the operations may be performed for images of the patient's femur and for images of the patient's pelvis. The operations may be performed for the bones of the joint separately to account for arthritic or other damage done to the patient's joint. In particular and as explained in more detail below, the operations described herein are utilized to reformat the received 2D images of the patient to approximate true anatomical coordinate images of the patient's anatomy. In other words, the images are reformatted to approximate true sagittal, axial, and coronal images of the joint. However, due to damage of the joint, reformatting of the femur and the tibia to a true anatomical coordinate may be difficult. Thus, the operations utilized to reformat the images may be performed separately on the femur and the tibia (or other bones of the patient's joint, depending on the joint undergoing the procedure).

Further, many of the operations may be performed multiple times. For example, the images may be reformatted as described below any number of times to approach images illustrating the joint in a true anatomical coordinate. Thus, a first iteration of the reformatting may be performed for a first correction of the images closer to a true anatomical coordinate. Additional iterations of the reformatting process may then be performed to fine tune the images into a coordinate system that approximates true anatomical coordinates of the patient's joint. Further, the reformatting of each bone of the joint may be performed multiple times so that the approximation of the true anatomical coordinates of the images is performed for the images of the femur and the tibia separately. As such, one or more of the operations described below may be performed any number of times to aid in reformatting the received 2D images to approximate a true anatomical coordinate image of the portions of the joint in relation to the joint replacement procedure.

Beginning in operation 602, the computing device receives the 2D images of a patient's joint or joints generated from an imaging device, as described above. In one embodiment, the computing device receives the 2D images over a network or virtual network from the imaging device or other computing device associated with the imaging device. The 2D images may be packaged into a series of images that are available to be viewed through a display of the computing device. Also, as described above, the 2D images of the joint may include a plurality of images taken along a coronal plane, an axial plane, a sagittal plane through the knee and/or other joints of the patient, or a combination of coronal, sagittal and/or axial views.

Once the 2D images of the joint are uploaded or otherwise available, the computing device or operator may conduct a reformatting stage on the 2D images in operation 604. In general, the reformatting of the 2D images is conducted on the 2D images to create a 2D image or reorient the 2D images to a coordinate system that approximates the true anatomical coordinate of the patient's joint. Thus, reformatting of the 2D images includes reorientation of the images and/or extrapolation of the joint between captured 2D images. In this manner, the 2D images may be rotated in three dimensions to reformat the images or create new images that approximate the true anatomical coordinate of the patient's joint. These images with the approximation of the true anatomical coordinate may be used to create the arthroplasty cutting jig discussed herein.

In general, the reformatting of the 2D images occurs through the placement of one or more reference points or lines within the 2D images and to reformat the images. The one or more reference points in the images provide the computing device with orientation markers in the images to aid in the process of identifying the landmarks of the patient's anatomy within the images. Through these selected landmarks and reference lines, the computing device can reformat the images into images that may be used to create a customized arthroplasty cutting jig.

In addition, reformatting the 2D images through the computing device may provide several functions to the overall customized cutting jig creation method. For example, during the reformatting stage of the customized cutting jig creation method, unusable or misaligned 2D images of the patient's joint may be noted and/or discarded. This allows for a request for additional images be taken of the patient early in the jig creation process. In addition, the imaging process may include several irregularities that may affect the effectiveness of the customized cutting jig. For example, during imaging, the patient may be oriented at an angle within the imaging device such that each of the images taken may not align with the imaging device coordinates. In this example, the resulting images may be misaligned with the global coordinates of the imaging device, making the location of the landmarks within the 2D images be similarly off axis from the global coordinate system. However, through the reformatting stage described below, one or more of the 2D images may be realigned or reoriented to compensate for the angle in which the patient was placed in the imaging device.

In another example, the 2D images, as received at the computing device, may be blurry due to movement of the patient during the imaging process. In general, the imaging procedure may take several minutes to complete, depending on the spacing between the image slices obtained. This requires that the patient remain still throughout the imagine procedure. However, it may be difficult for some patients to remain still within the imaging device during the entire procedure, due to patient discomfort due to injury or improper imaging device use, such that some movement by the patient is captured in the 2D images. Depending on the severity of the movement, the 2D images may become blurry or provide an inaccurate representation of the patient's joint. In these cases, the reformatting stage of the method illustrated in FIG. 6 may identify and account for such patient movement, as described in more detail below with reference to FIG. 7.

After reformatting of the images occurs, the operator or computing device may then perform a planning stage on the 2D images, as shown in operation 606. During the planning stage, one or more landmarks on the 2D images of the patient's joint are identified and noted with electronic markers on the images in the computing device. In one embodiment, these landmarks are utilized by the computing device to create a footprint within the 2D images in which a customized cutting jig may be located in relation to the anatomy contained within the 2D images. For example, during the planning stage, the operator may indicate a medial-lateral length of a femoral cutting jig based on the 2D images of the patient's femur. As described in more detail below, the planning stage provides several reference points or landmarks in the 2D images to the computing device that may be utilized by the computing device in creating a customized cutting jig template. As also discussed below, the planning stage may be performed for separate portions of the joint, such as the femur and the tibia. This is due to the reformatting of the 2D images operation occurring on the femur and the tibia separately. In other words, the femur may be reformatted in a particular orientation while the tibia is reformatted in another orientation. As such, the planning operations may be performed for the various portions of the joint that undergo the reformatting operation.

Figure 6A:
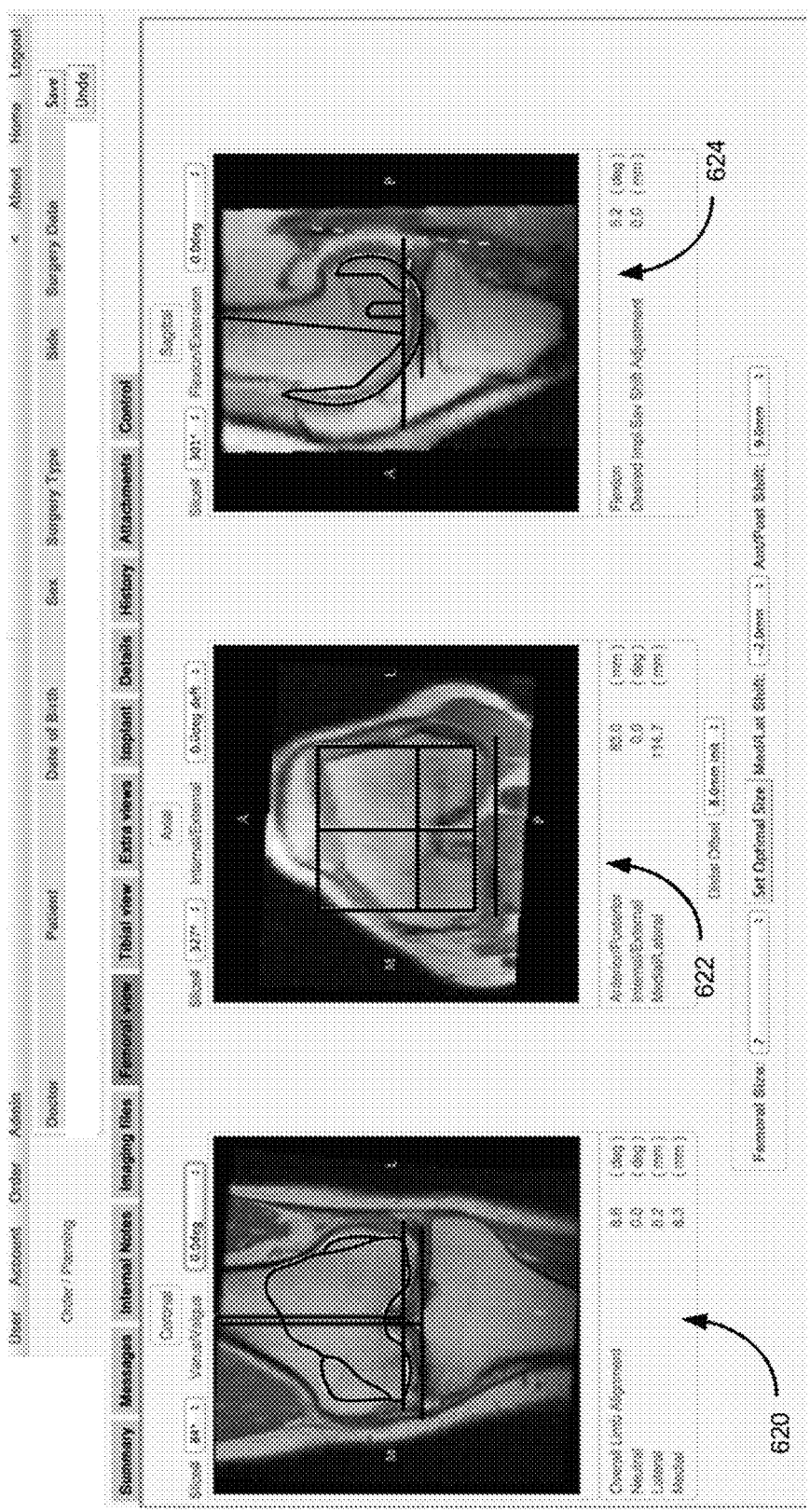
FIG. 6A is an illustration of a series of reformatted 2D images of a patient's femur with a superimposed femur implant contained within the images.
Figure 6B:
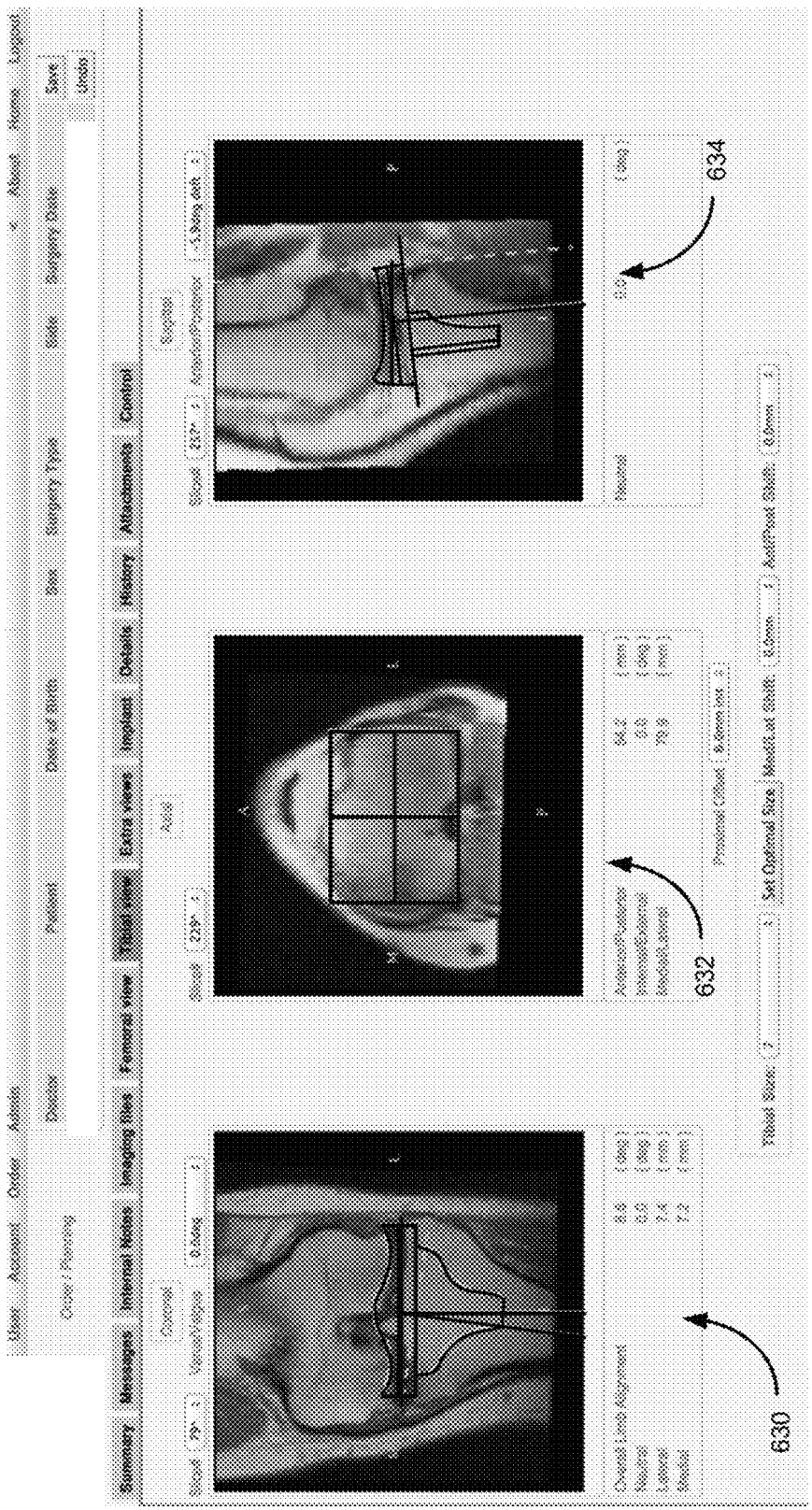
FIG. 6B is an illustration of a series of reformatted 2D images of a patient's tibia with a superimposed tibia implant contained within the images

In operation 608, the reformatted 2D images may be captured by the computing device and a stencil of the implant may be superimposed on the reformatted 2D images. For example, the reformatted femur images may be captured and a generic femur implant may be superimposed on the reformatted femur 2D images. One example of combined reformatted images and implant stencil for a patient's femur is illustrated in FIG. 6A and an example of combined reformatted images and implant stencil for a patient's tibia is illustrated in FIG. 6B. Also, the combined reformatted images and implant stencil such as those shown in FIGS. 6A and 6B may be provided to the surgeon for approval by the surgeon. In particular, the images may be transmitted from the computing device to the surgeon for review. In one embodiment, the images are available through a website for review by the surgeon. For example, the surgeon may verify that the surface of the femur implant is located below the anterior cortex point on the femur shaft and the femur shaft angle is parallel to a reference line in the implant stencil. In general, any criteria may be utilized by the surgeon when evaluating the proposed implant positioning on the reformatted images.

Upon approval by the surgeon, the design of the cutting jig may occur. In one embodiment, the surgeon may visually determine the proper alignment of the proposed implant on the reformatted 2D images of the patient's joint and indicate an approval with an input device to a computer on which the images are being reviewed. The provided reformatted images may also include specific measurements of the implants or images, such as medial-lateral length, anterior-posterior length, angle of the implant, and the like. Also, the provided reformatted images may include a reformatted sagittal image of the joint 624,634, a reformatted coronal image of the joint 620,630, and/or a reformatted axial image of the joint 622,632.

In operation 610, the operator or computing device may then perform a template design stage on the 2D images. During the template design stage, one or more electronic markers or shapes are placed on one or more of the reformatted 2D images of the patient's joint. It should be noted that reference and discussion of 2D images in this disclosure may refer to either the original 2D images of the patient, the reformatted images of the patient as described above, or a combination of both the original and the reformatted images, unless specifically noted. In one example, the electronic shapes correspond to contact shapes of the customized cutting jigs for the femur and tibia. Thus, the electronic shapes may be placed by the operator or computing device in the 2D image in locations similar to mating locations on the patient's joint for the customized cutting jig. As such, as described in more detail below, the computing device may utilize the template design to generate a cutting or milling program from the 2D images in operation 612. The milling program, as described above, may then be provided to a CNC machine to generate the arthroplasty cutting jig. In particular, the template design features identified in the 2D images are translated into the milling program to create a cutting jig that is customized to the particular joint shown in the 2D images. As mentioned above, one or more additional reformatting stages of the 2D images may also be conducted at any point in the method illustrated in FIG. 6.

Figure 7A:
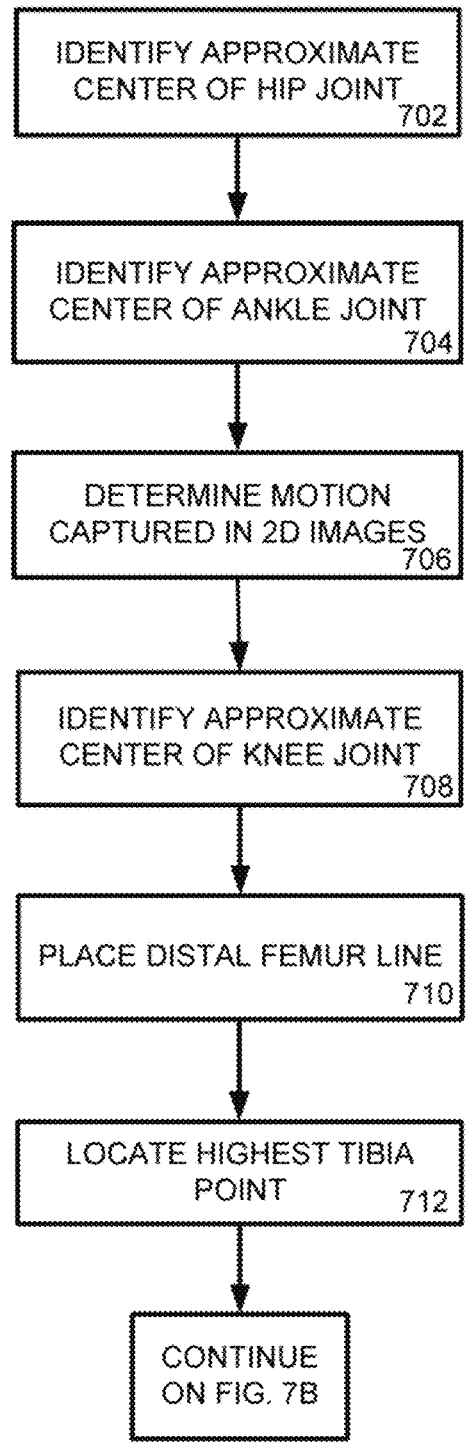
FIGS. 7A and 7B is a flowchart illustrating a method for reformatting a series of 2D images of a patient's joint to reorient the images along a common axis.
Figure 7B:
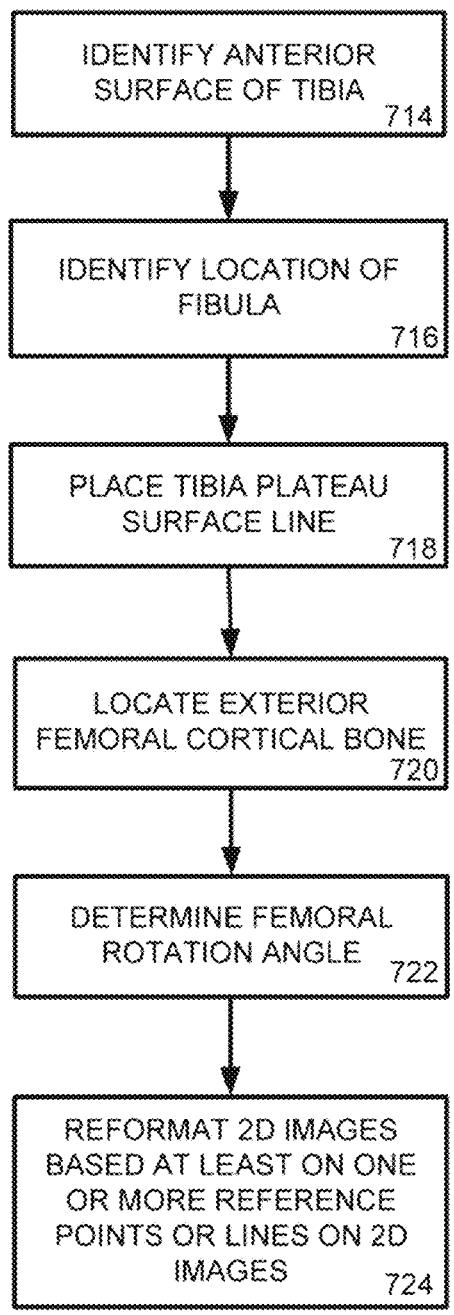

As mentioned above, a reformatting of the 2D images of the patient's joint may be conducted to reorient in three dimensions and verify the accuracy of the images. FIGS. 7A and 7B is a flowchart illustrating a method for reformatting a series of 2D images of a patient's joint to reformat the images from an image machine-determined coordinate axis to an approximate true anatomical coordinate axis. Additionally, the flowchart of FIGS. 7A and 7B allows an operator or the computing device to identify and reject a series of 2D images that may not be accurate or applicable to the process of creating the customized arthroplasty cutting jig. The operations detailed in FIGS. 7A and 7B may be performed as operation 604 described above with relation to FIG. 6. As such, the operations may be performed by an operator of a computing device or the computing device itself through which the 2D images are available for viewing, alterable, and available for placing electronic markers within the images.

Figure 8:
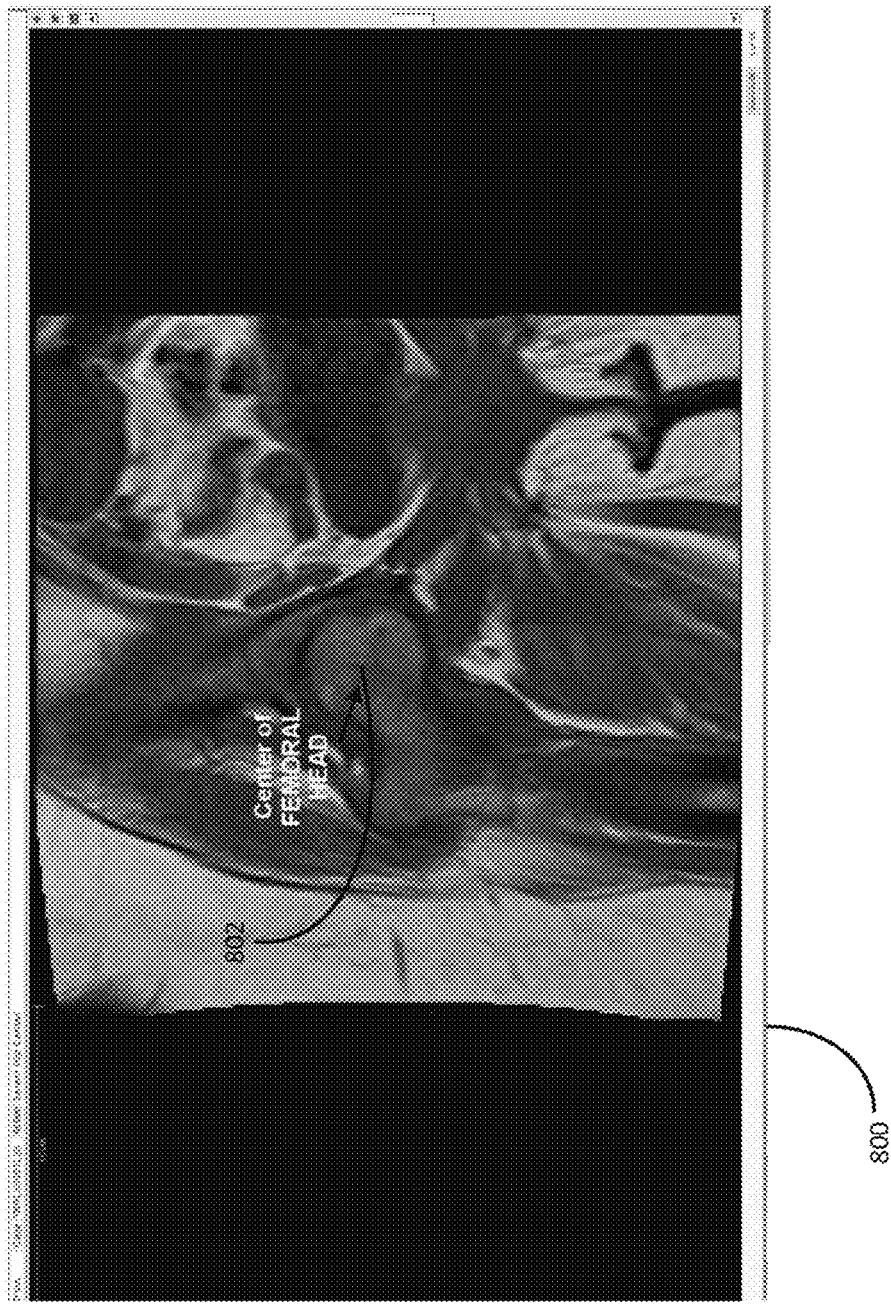
FIG. 8 is a screenshot of a 2D image used for locating an approximate center of a patient's hip.

Beginning in operation 702, the computing device may identify the approximate center of the patient's hip in one of the 2D images. In one embodiment, as indicated in FIG. 8, an operator sitting in front of a monitor of the computing device tabs through the various 2D images. In one example, the 2D images are coronal 2D images of a patient's joint, such as a hip. In other examples, however, the 2D images may be sagittal or axial images. As explained above, the 2D images may be a set of 2D images obtained through an imaging device as the device takes a series of slice images of the joint. Thus, any number of coronal images may be present in the set of 2D images from which the clearest or best fit image may be selected by the operator by tabbing through the images. In particular, the operator tabs through the series of images to determine visually a particular 2D image until a clear image of the hip, and in particular the top section of the femur, is visible in the image. In one embodiment, the selected 2D image includes the largest instance of the femoral head in the coronal view of image slices.

Once a 2D image is selected, the operator then utilizes an input device (such as a mouse or a keyboard) of the computing device to locate and electronically mark the center of the hip 802 on the selected 2D image. In particular, the operator attempts to locate and electronically mark the center of the femoral head in the selected 2D image. The electronic marking of the femoral head is then stored in the computing device as a marker related to a global coordinate system within the system for orienting the 2D images. In the example of FIG. 8, the center of the femoral head is indicated as point 802.

In one embodiment, the selected hip center 802 may be an approximate center point of the femur head via visual examination of the 2D image. Thus, it is not necessary that the operator or computing device select the exact center of the femoral head. Rather, the selection of the center can be approximate. Further, in another embodiment, the computing device itself may analyze the 2D images to select an image (perhaps based on clarity of image) and electronically mark the center 802 of the femoral head. In this embodiment, the location of the femoral head is thereby at least partially automated.

In addition to locating the center of the hip, the operator or computing device may visually inspect any of the 2D images and reject the images for various reasons. For example, one constraint may be that the images must be oriented such that the femoral shaft within the image points to the bottom of the screen. If the 2D images are oriented in another direction, the images may be noted as unacceptable for the procedure and a new set of images may be conducted. FIG. 9 illustrates several 2D image orientations of the femoral head that may be deemed unacceptable for the customizing procedure and rejected.

Figure 10:
FIG. 10 is a screenshot of a coronal view of a patient's hip with the medial end of the femur head identified.
Figure 11:
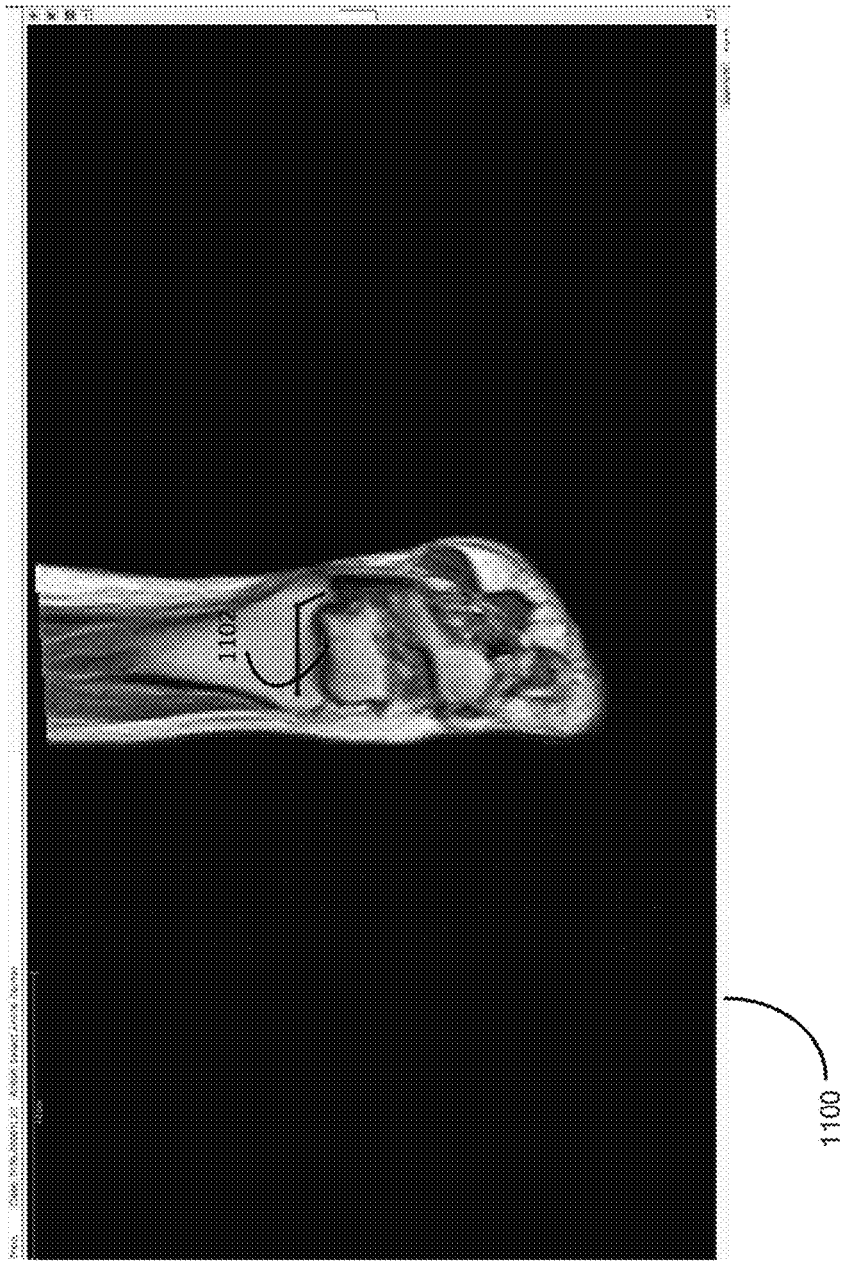
FIG. 11 is a screenshot of a coronal view of a patient's ankle with the center of the ankle identified.
Figure 12:
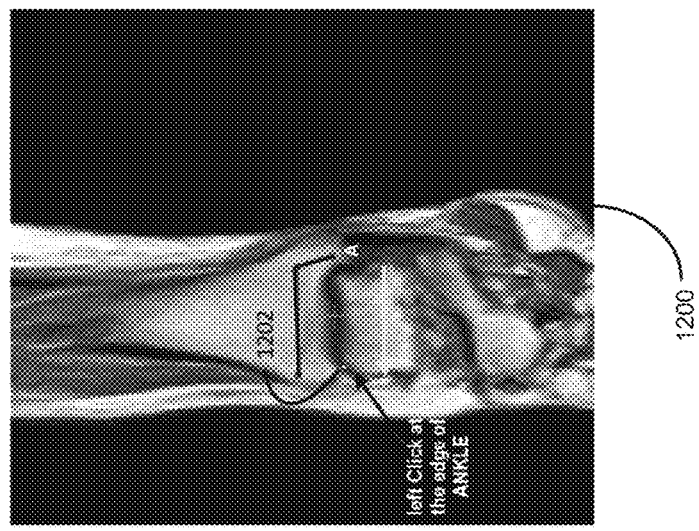
FIG. 12 is a screenshot of a coronal image of a patient's ankle with the edge of the ankle identified.
Figure 13:
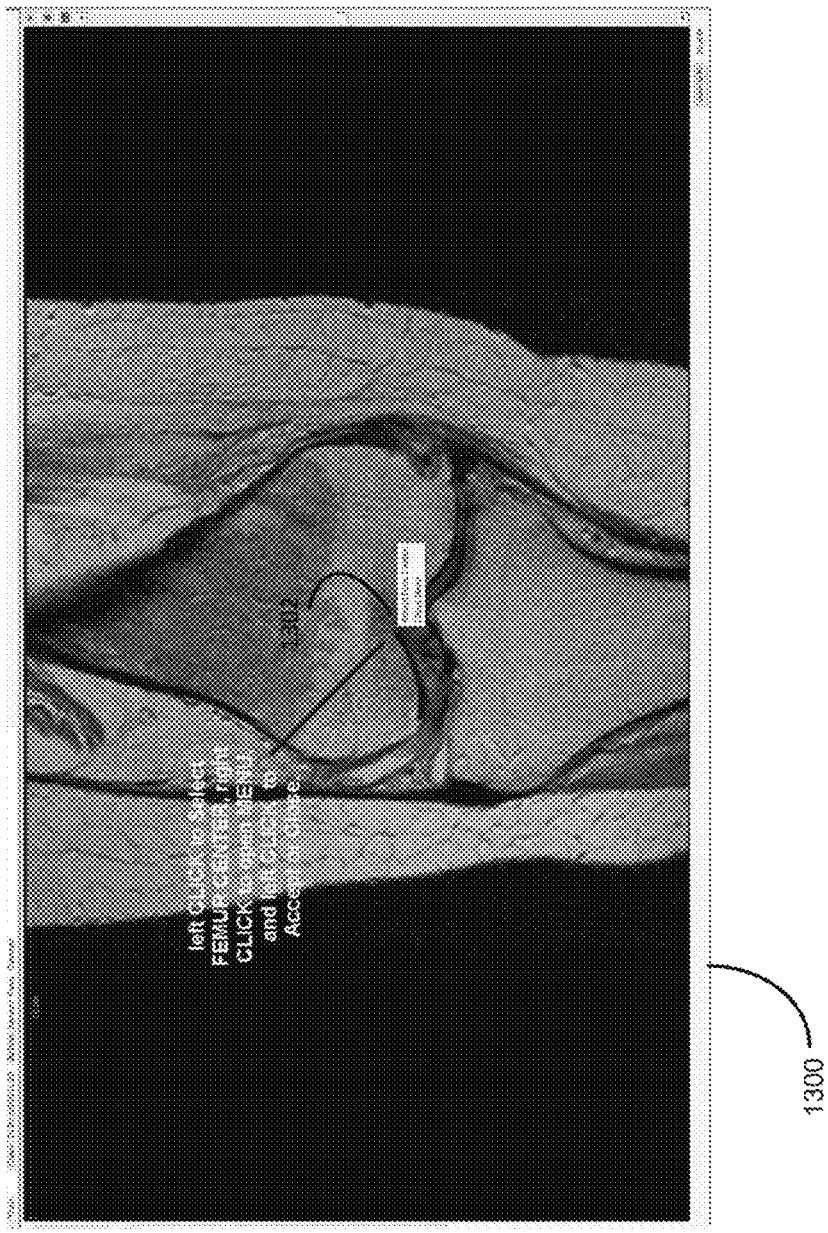
FIG. 13 is a screenshot of a coronal image of a patient's knee with the center of the knee identified.
Figure 14:
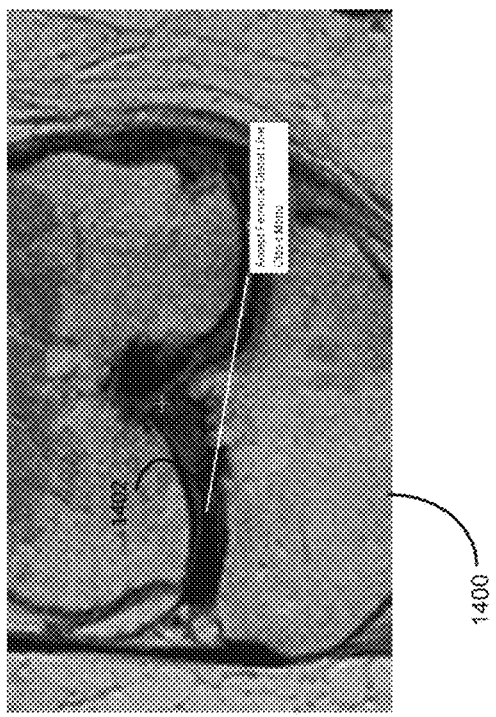
FIG. 14 is a screenshot of a coronal image of a patient's knee with the distal femur line of the knee identified.
Figure 15:
FIG. 15 is screenshot of a coronal image of a patient's knee with the highest tibia point of the knee identified.
Figure 16:
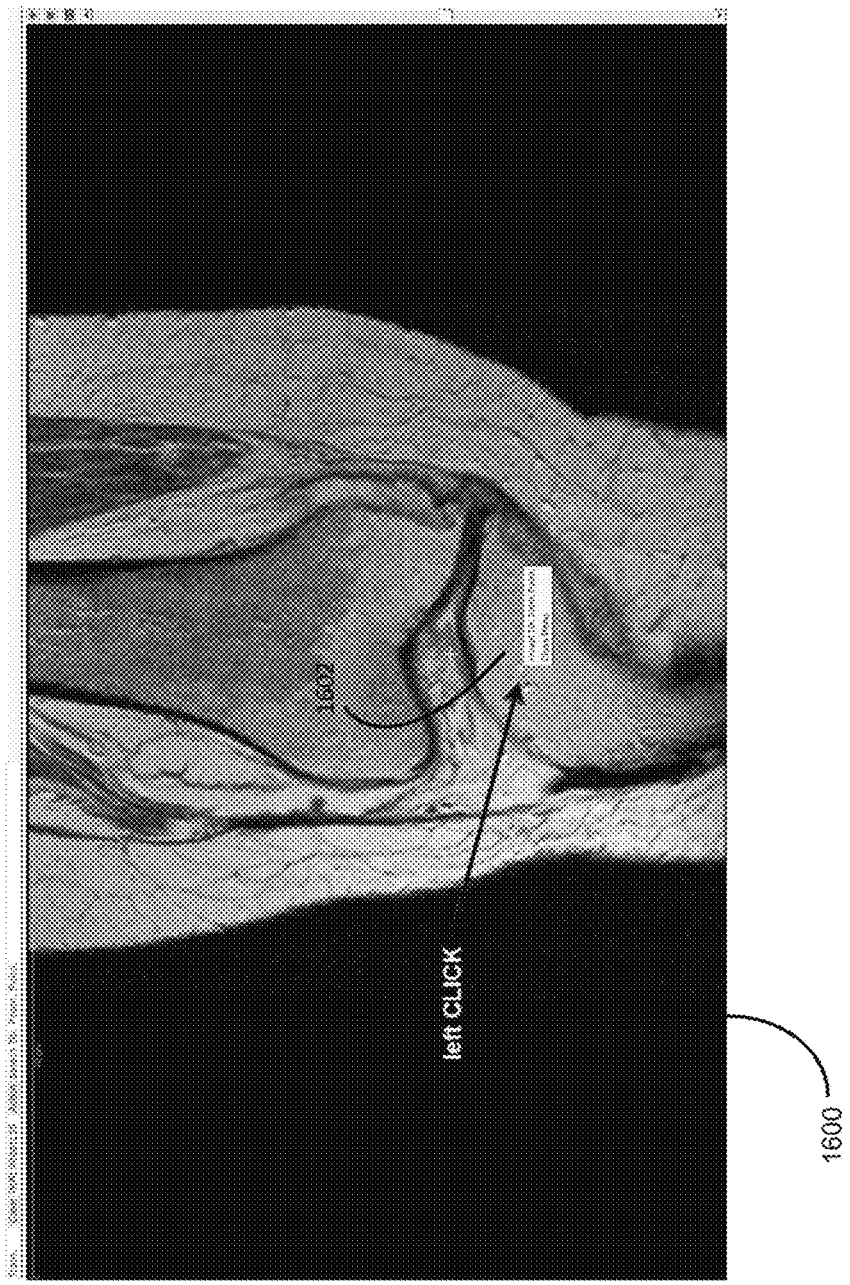
FIG. 16 is a screenshot of a coronal image of a patient's knee with the anterior surface of the tibia of the knee identified.
Figure 17:
FIG. 17 is a screenshot of a coronal image of a patient's knee with the location of the fibula of the knee identified.
Figure 18:
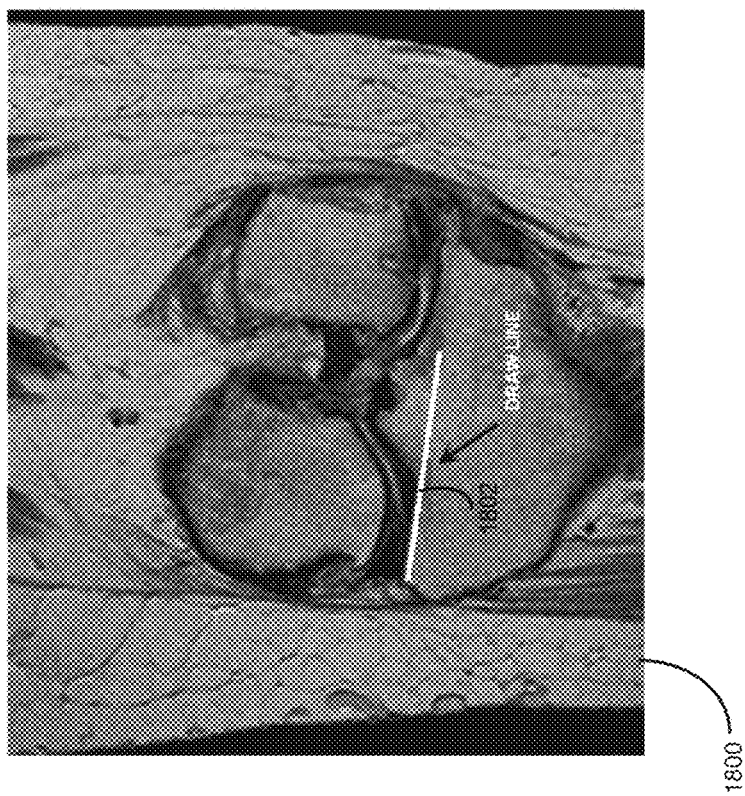
FIG. 18 is a screenshot of a coronal image of a patient's knee with a tibia plateau surface line of the knee identified in the image.
Figure 19:
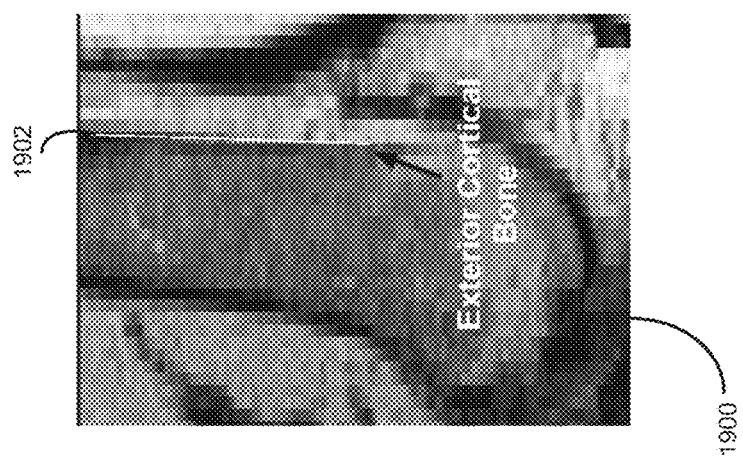
FIG. 19 is a screenshot of a coronal image of a patient's knee with an exterior femoral cortical bone shaft of the knee identified in the image.
Figure 20:
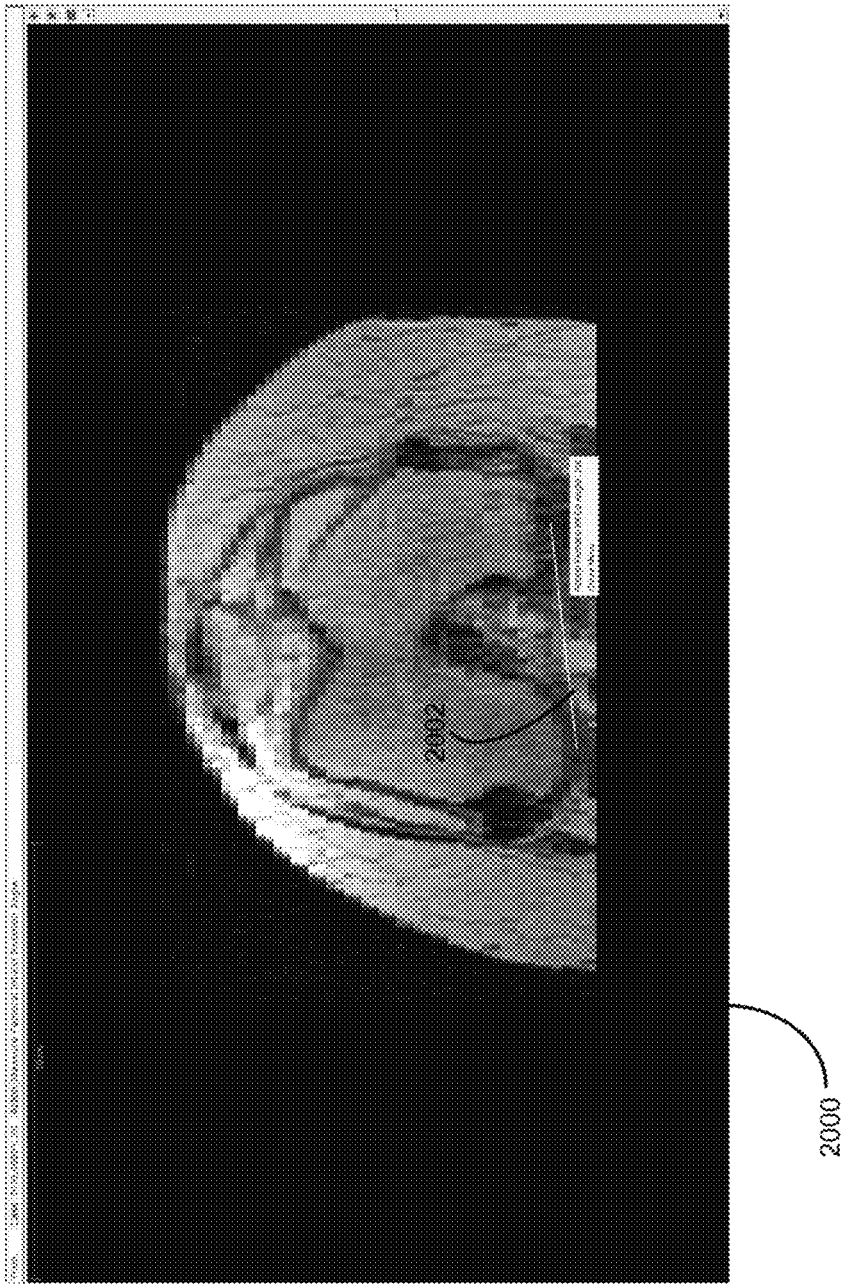
FIG. 20 is a screenshot of an axial image of a patient's knee with a femoral rotation line of the knee identified in the image.

As shown in the screenshot 1000 of FIG. 10, one embodiment of the method of FIG. 7 includes identifying the end of the femur, opposite the femoral shaft. In particular, the screenshot 1000 illustrates a coronal view of a patient's hip with the medial end of the femur head identified. In this example, the operator or computing device identifies the edge of the bone 1002 on the femoral head opposite the femoral shaft 1004. As explained in more detail below, the end of femur point 1002 and hip center point 802 may be used by the computing device to reorient the 2D images, ensure the images are proper, and to establish a global coordinate reference for the images.

Returning to FIG. 7, the operator or computing device identifies the center of the ankle joint of the patient utilizing one or more of the 2D images in operation 704. The identification of the ankle center is conducted in a similar manner as identifying the center of the hip, described above. Thus, an operator sitting in front of a monitor of the computing device tabs through a set of coronal 2D images of the ankle and selects one or more images to identify points on the image. In other embodiments, the images may be sagittal or axial images. Once the 2D image is selected, the operator then utilizes the input device to the computing device to locate and electronically mark the center of the ankle on the selected 2D image, as shown as point 1102 in the coronal screenshot of the patient's ankle in FIG. 11. The electronic marking of the ankle center 1102 is then stored in the computing device as a marker related to a global coordinate system within the system for orienting the 2D images. As with the center of the hip, the location of the center of the ankle 1102 may be approximate and may be at least partially automated by the computing device.

In addition to locating the center of the ankle, the operator or computing device can visually inspect the 2D images and reject the images for various reasons, such as blurriness or improper alignment. Further, as shown in the coronal 2D image 1200 in the screenshot of FIG. 12, one embodiment of the method includes identifying the edge of the ankle 1202, opposite the fibular. As such, an electronic marker may be placed in the 2D image 1200 at the edge of the ankle 1202 by the operator or computing device. The visual markers on the 2D images may be used by the computing device to reorient the 2D images, ensure the images are proper, and to establish a global coordinate reference for the images.

Returning again to FIG. 7, the operator or computing device determines whether substantial movement of the patient occurred during imaging of the patient's joint, such as the patient's knee, in operation 706. In particular, the operator or computing device may utilize the input device to scroll rapidly through the set of 2D images of the patient's joint. By scrolling through the images, movement or wobbling of the images may become apparent. In some instances, significant movement of the patient during imaging may make the resulting set of 2D images unusable for creating a customized cutting guide. In such an instance, the operator or computing device notes the failings of the received 2D images and requests additional images of the patient's joint be taken.

In operation 708, the center of the knee (based on the 2D images) is determined. In one embodiment, the center of the knee is identified as the approximate center of the trochlear valley of the femur in the 2D image, which is identified in a similar manner as identifying the center of the hip and ankle, described above. Thus, an operator sitting in front of a monitor of the computing device tabs through the various coronal 2D images of the knee and selects one or more images to identify points on the image. In one embodiment, the selected 2D image shows the deepest trochlear valley when viewed from anterior aspect. In this image, the center point of the knee is the center of the trochlear valley in the selected 2D image. Similar to above, the images may also be sagittal or axial images of the knee.

Once a 2D image is selected, the operator then utilizes the input device to the computing device to locate and electronically mark the center of the knee on the selected 2D image. An example of the location of the knee center 1302 is indicated in the 2D coronal image 1300 of the screenshot of FIG. 13. The electronic marking of the knee center 1302 is then stored in the computing device as an electronic marker related to the knee for orienting the 2D images. The location of the center of the knee may be approximate and may be at least partially automated by the computing device. As discussed above, the selected centers of the hip, ankle, and knee may be used to orient the 2D images to a global coordinate system that aids the computing device in creating an accurate customized cutting guide. In addition, by identifying the end of the femur and the edge of the ankle, the operator or computing device may determine if the received 2D images are of the proper limb and joints of the patient, based on a doctor's indication of the intended procedure. For example, the edge markers may verify that the set of 2D images is of the patient's right leg, which may then be verified based on a doctor's indication that the patient's right knee will undergo the arthroplasty procedure.

At this point in the process, the computing device may determine whether the 2D images are of the patient's right leg to the patient's left leg. However, the 2D images are still oriented in the image machine-defined coordinate system. To begin a first reformatting of the 2D images into a coordinate system that approximates the true anatomical coordinate system of the patient's joint, additional operations may be performed. For example, in operation 710, a femur distal line of the 2D knee images knee is identified on the images. One example of a femur distal line 1402 is illustrated in the coronal 2D image of the patient's knee in the screenshot 1400 of FIG. 14. In general, the femur distal line 1402 is a straight line from the most distal end of one condyle of the femur to the most distal end of the other condyle as shown in the selected 2D image. To determine the femur distal line, an operator sitting in front of a monitor of the computing device tabs through the set of coronal 2D images of the knee and selects one or more images to identify points on the image. The operator then locates or approximates the location of the most distal end of one of the femur condyles and, utilizing the input device, electronically selects the most distal end of the condyle. The operator may also drag a line to the most distal end of the other femoral condyle or simply select the most distal end of the other condyle. In this manner, a line that indicates a straight line from the distal end of one condyle of the femur to the distal end of the other condyle is represented on the selected 2D image. As should be appreciated, the femur distal line 1402 may indicate an orientation angle of the patient during the imaging process. This angle may be noted by the computing device for re-orienting the 2D images and ensure a proper customized cutting guide, as described below.

In operation 712, the operator or computing device determines the 2D image with the highest point of the tibia spine and identifies the highest point in the 2D image. In one embodiment, the operator sitting in front of the monitor tabs through the set of coronal 2D images of the knee and selects one or more images that shows the tibia spine with the highest point. Once a 2D image is selected, the operator then utilizes the input device to the computing device to locate and electronically mark the highest point of the tibia spine. An example of the electronic marker located at the highest tibia spine point 1502 is shown in the 2D coronal image of the knee in the screenshot 1500 of FIG. 15. The electronic marking of the tibia spine high point 1502 is then stored in the computing device as a marker related to the knee for orienting the 2D images.

In operation 714, the operator or computing device selects a 2D image from the set of images and identifies the anterior edge of the tibia. In particular, the anterior edge of the tibia may be observed in one of a series of coronal 2D images by scrolling. Thus, the operator sitting in front of the monitor tabs through the various coronal 2D images of the knee and selects a 2D image closest to the anterior edge of the tibia. Once a 2D image is selected, the operator then utilizes the input device to locate and electronically mark the anterior tibia edge. An example of the electronic marker located at the highest tibia spine point 1602 is shown in the 2D coronal image of the knee in the screenshot 1600 of FIG. 16. The electronic marking of the anterior tibia edge 1602 is then stored in the computing device as a marker related to the knee for orienting the 2D images. The anterior tibia edge 1602 provides the computing device with a relative anterior point of the set of 2D images.

Continuing the reformatting of the 2D images, the operator or computing device identifies the fibula in operation 716. Similar to the above, the operator tabs through the various 2D images of the knee and selects one or more coronal images that show the fibula of the patient. Once a 2D image is selected, the operator then utilizes the input device to the computing device to locate and electronically mark the fibula in the image. An example of the electronic marker identifying the fibula 1702 in the image is shown in the 2D coronal image of the knee in the screenshot 1700 of FIG. 17. The electronic marking of the fibula 1702 is then stored in the computing device as a marker related to the knee for orienting the 2D images. The location of the fibula in the 2D images may aid the computing device in determining the left and right side of the patient in relation to the 2D images.

In operation 718, the operator or computing device identifies a tibia plateau surface line in at least one of the 2D images. One particular example an identification of the tibia plateau surface line 1802 is shown in the 2D coronal image of the knee in the screenshot 1800 of FIG. 18. To determine the tibia plateau line, an operator sitting in front of a monitor of the computing device tabs through the set of coronal 2D images of the knee of the patient and selects one or more images to identify points on the image. In particular, the operator or computing device identifies a 2D image that includes a nearly straight cortical bone feature on an undamaged side of the tibia plateau. The operator then, utilizing the input device, electronically draws a line along the tibia plateau line identified in the 2D image. In general, the tibia plateau line follows the nearly straight cortical bone feature of the tibia described above. In this manner, a line that indicates a straight line along the tibia plateau line is represented on the selected 2D image. As should be appreciated, the tibia plateau line 1802 may indicate an orientation angle of the patient during the imaging process. This angle may be noted by the computing device for re-orienting the 2D images and ensure a proper customized cutting guide.

In operation 720, the operator or computer device identifies the femoral cortical bone exterior line in one or more of the 2D images. One example of a femoral cortical bone exterior shaft line 1902 is shown in the 2D coronal image of the knee in the screenshot 1900 of FIG. 19. To determine the femoral cortical bone exterior shaft line, an operator sitting in front of a monitor of the computing device tabs through the various coronal 2D images of the knee and selects one or more images to identify points on the image. In particular, the operator or computing device identifies a coronal 2D image that includes the largest femoral shaft thickness within the set of images. This particular 2D image may provide the best image of identifying the femoral cortical bone exterior line.

The operator then utilizing the input device, electronically draws a line along the femoral cortical bone exterior line identified in the selected 2D image. In general, the femoral cortical bone exterior line follows the exterior of the femoral cortical bone along the shaft of the femur. In this manner, a line that indicates a straight line along the femoral cortical bone exterior shaft line is represented on the 2D image. As should be appreciated, the femoral cortical bone exterior shaft line 1902 may indicate an orientation angle of the patient during the imaging process. For example, the exterior cortical bone of the femoral shaft provides an indication of the medial-lateral angle at which the patient was oriented during the imaging process. As such, this angle may be noted by the computing device for re-orienting the 2D images and ensure a proper customized cutting guide. Further, the line along the femoral cortical bone exterior may be adjusted by the operator to align best with the femoral line in the 2D image.

The operator or computer device may also identify an interior-exterior rotation angle of the femur in one or more of the 2D images in operation 722. For this operation, a series of axial images of the knee may be employed, such as the axial 2D image shown in the screenshot 2000 of FIG. 20. To determine the interior-exterior rotation angle of the femur, an operator sitting in front of a monitor of the computing device tabs through the various axial 2D images of the knee and selects one or more images to identify points on the image. In particular, the operator or computing device identifies an axial 2D image that shows the image with the largest condyles of the femur. This particular 2D image may provide the best image for identifying the interior-exterior rotation angle of the femur.

The operator then utilizing the input device, electronically draws a line 2002 from the most posterior location of one femoral condyle to the most posterior location of the other femoral condyle in the 2D axial image of the knee. For example, in the 2D image shown in FIG. 20, the most posterior location of each condyle is closest to the bottom of the image. In this manner, a line 2002 that indicates a straight line from the posterior edges of the femoral condyles is determined and electronically marked on the 2D image. As should be appreciated, the line 2002 may indicate an interior-exterior rotation angle of the patient during the imaging process. In other words, the interior-exterior rotation angle 2002 as drawn in the image provides the computing device with an indication of the rotation of the patient during the imaging process. This angle may be noted by the computing device for re-orienting the 2D images and ensure a proper customized cutting guide.

Finally, in operation 724, the operator or computing device utilizes one or more of the electronic markers and/or lines determined above to reformat the series of 2D images along a coordinate system that more closely approximates a true anatomical coordinate system for the patient based on the 2D images. In general, the reformatting of the images may include reorientation of the images and/or extrapolation of data from between image slices. In this manner, the images are reformatted in three dimensions to approximate the true anatomical coordinate system. For example, based on the femoral cortical bone exterior shaft line 1902, the computing device determines an angle at which the patient was placed in the imaging device thereby angling each of the generated 2D images. Thus, from the information entered into the computing device above, each of the 2D images in the set of images may be reformatted to account for the angle of the images obtained during imaging. Similarly, the femur distal line 1402 may provide other angle information about the 2D images. The reference lines and points identified on the 2D images through the operations described above may or may not be utilized by the computing device to reformat the 2D images to account for imaging errors, such as patient movement and placement angle during the imaging process. In general, any of the reference lines and points identified on the 2D images may be considered by the computing device when reformatting the 2D images. In one embodiment, the computing device utilizes all of the points and lines indicated above. In other embodiments, one or more of the lines or points may be dismissed or not considered when reformatting the 2D images. In some circumstances, such reformatting may adjust for an imaging angle of over 3 degrees from the true anatomical coordinate axis of the patient to an imaging angle of less than 2 degrees from the true anatomical coordinate axis.

After the 2D images are reformatted, a pre-planning stage of the 2D images may be performed by the operator or computing device. In general, the pre-planning stage results in a further refinement of the reformatting of the 2D images discussed above. In other words, the pre-planning stage reformats the 2D images even further to the true anatomical coordinate axis of the patient. After pre-planning, the resulting 2D reformatted images may be used during a jig design phase, discussed in more detail below. Also, many of the reference lines and/or boxes placed in the 2D images and discussed below reference non-damaged portions of the patient's joint to provide a more accurate placement on the images. By utilizing the non-damaged portion of the joint (rather than the arthritic or damaged portion), a cleaner location in the image of the reference points, lines, and boxes may be achieved. This is discussed in more detail throughout the description of the flowcharts of FIG. 21 and FIG. 29.

Figure 21:
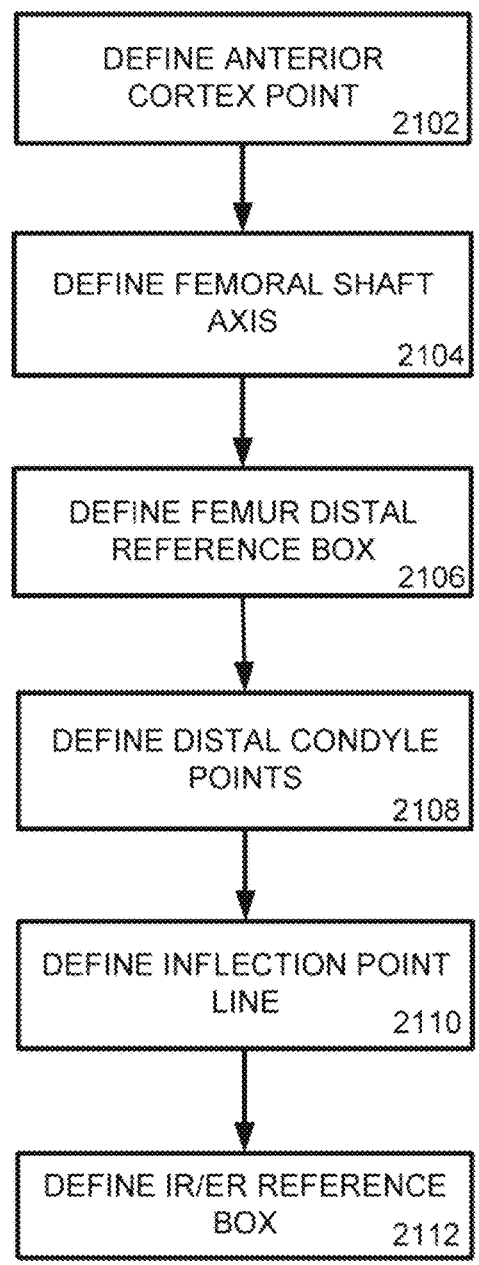
FIG. 21 is a flowchart illustrating a method for a planning stage for a customized arthroplasty cutting jig based on a series of two-dimensional images of a patient's joint to identify one or more landmarks on a patient's femur in preparation for creating the cutting jig template for the femur.
Figure 22:
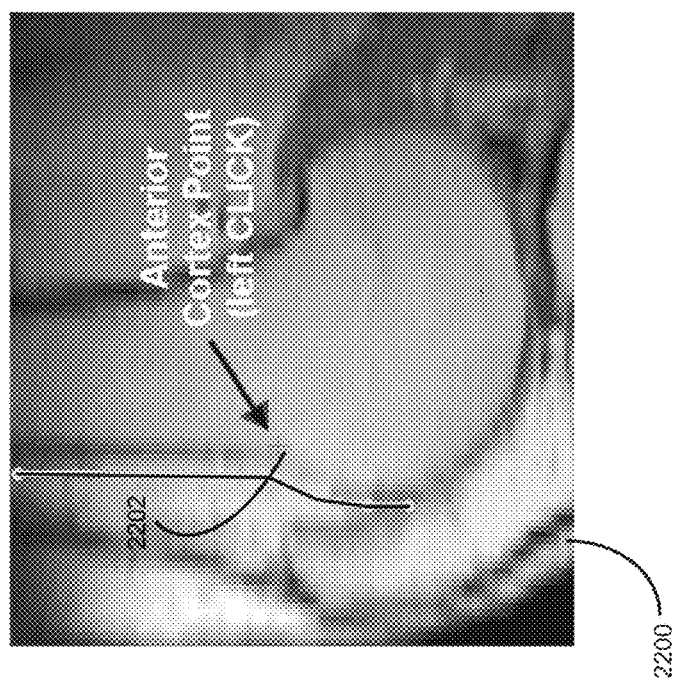
FIG. 22 is a screenshot of a sagittal image of a patient's knee with a femoral anterior cortex point of the knee identified in the image.
Figure 23:
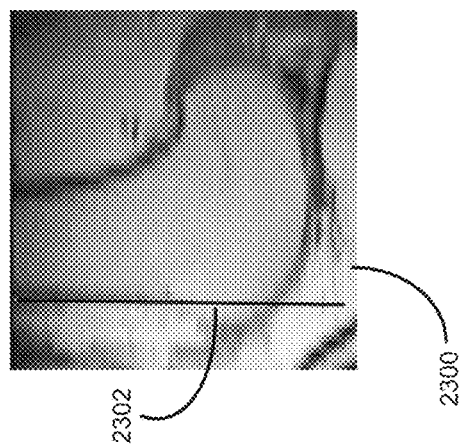
FIG. 23 is a screenshot of a sagittal image of a patient's knee with a femoral shaft axis of the knee identified in the image.

FIG. 21 is a flowchart illustrating a method for a pre-planning stage for a customized arthroplasty cutting jig based on a series of two-dimensional images of a patient's joint to identify one or more landmarks on a patient's femur in preparation for creating the cutting guide template for the femur. The operations detailed in FIG. 21 may be performed as part of operation 606 described above with relation to FIG. 6. As such, the operations may be performed by an operator of a computing device or the computing device itself through which the 2D images are available for viewing, alterable, and available for placing electronic markers within the images. In general, the planning stage operations of FIG. 21 results in a further refinement of the reformatting of the 2D images for the femur of the patient's knee.

Similar to the operations described above in relation to the method of FIGS. 7A and 7B, the operations of the method of FIG. 21 involve the operator or computing device analyzing the series of 2D images, selecting one or more of the 2D images, and utilizing an input device to the computing device to mark a point, line, or box in the images. The point, line, and/or box may be used by the computing device in the process of creating a customized arthroplasty cutting jig for the patient's femur. In particular, the marker points, lines, and boxes defined in the images in the operations of FIG. 21 provides a pre-planning stage to the customized cutting guide that is used by the computing device to reformat the coordinate system of the images into a coordinate system that approximates the true anatomical coordinate system for the patient's joint. In general, the planning stage of the customized cutting jig provides reference information to the computing device in preparation for generating the customized cutting jig milling program by reformatting the 2D images that are utilized to design the cutting jig.

Beginning in operation 2102, the operator or computing device may identify the anterior cortex point of the femur in one of the 2D images. The anterior cortex point 2202 of the femur is the location on the femur, as seen in the sagittal image of the screenshot 2200 illustrated in FIG. 22, where there is a sudden change in the anterior surface slope. Thus, an operator sitting in front of a monitor of the computing device tabs through the various sagittal 2D images of the patient's knee to select one where it appears the femoral shaft is the thickest. Once the image is selected, the operator then utilizes the input device (such as a mouse or a keyboard) to the computing device to locate and electronically mark the point near the anterior cortex point 2202 of the femur. In particular, a point adjacent the approximate anterior cortex point 2202 on the interior side of the cortical bone is noted on the 2D image. The electronic marking of the anterior cortex point is then stored in the computing device for reference.

In one embodiment, the anterior cortex point 2202 is utilized by the computing device as an outer limit of the template for the customized cutting guide. In particular, the customized cutting guide may not extend past the anterior cortex point 2202 of the femur to avoid the cutting guide resting or mating with the femur on the femur shaft. Implants that mate with the femur on the femoral shaft may not be as stable as those implants that are limited to mating on the femoral head. Thus, in this example, the anterior cortex point 2202 provides an outer limit for the implant through which the cutting guide provides the location on the patient's femur.

Returning to FIG. 21, the operator or computing device defines the femoral shaft axis in operation 2104. In particular, an operator sitting in front of a monitor of the computing device selects one or more sagittal images and, utilizing the input device, orients a line on the image to run parallel along the femoral shaft. In this manner, a line 2302 that indicates the angle of the femoral shaft in the 2D images is represented on the selected 2D image, as shown in the sagittal 2D image in the screenshot 2300 of FIG. 23. Similar to the placement of the femoral shaft axis discussed above, the femoral shaft axis line 2302 may indicate an angle of the 2D images that is noted by the computing device for reformatting the 2D images around a coordinate axis based on the patient's anatomy.

Figure 24:
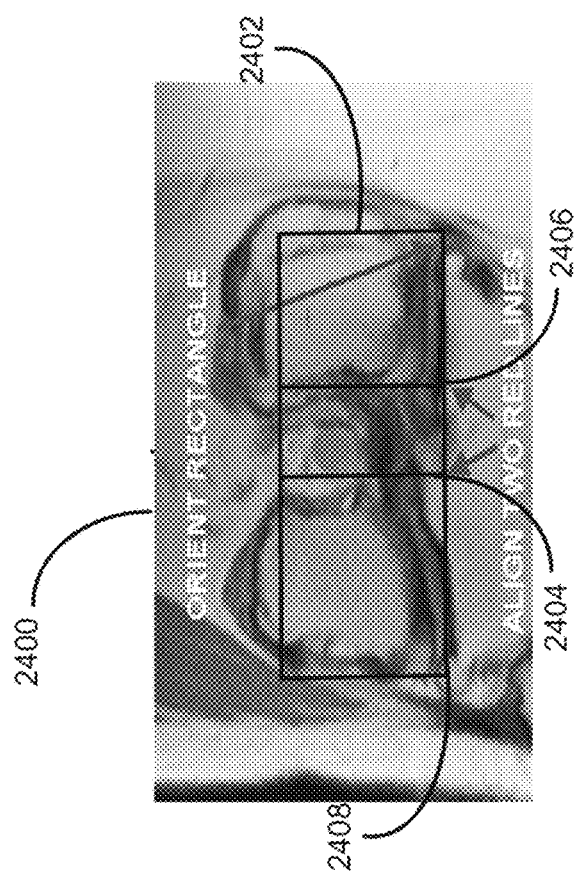
FIGS. 24 and 25 are screenshots of a coronal image of a patient's knee with a distal reference box of the knee identified in the image.
Figure 25:
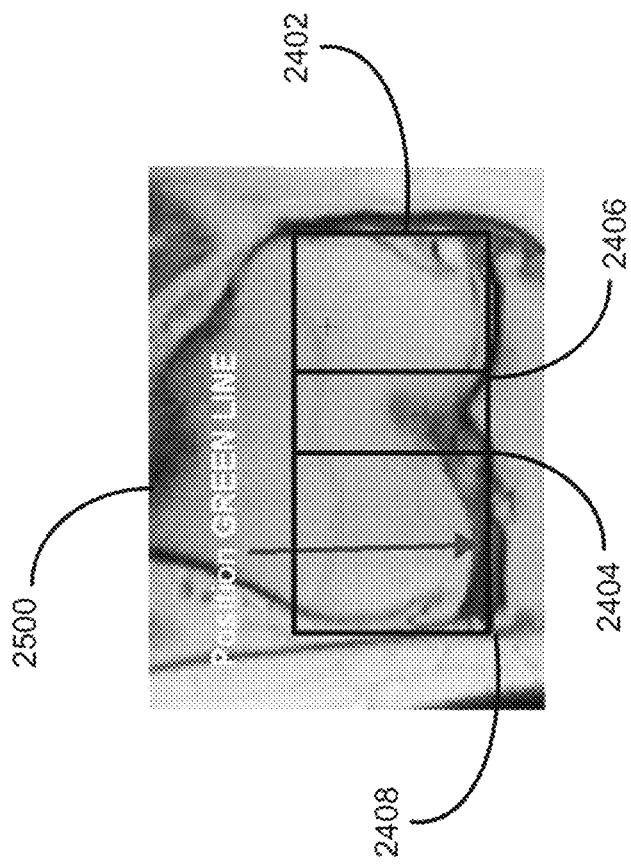
Figure 26:
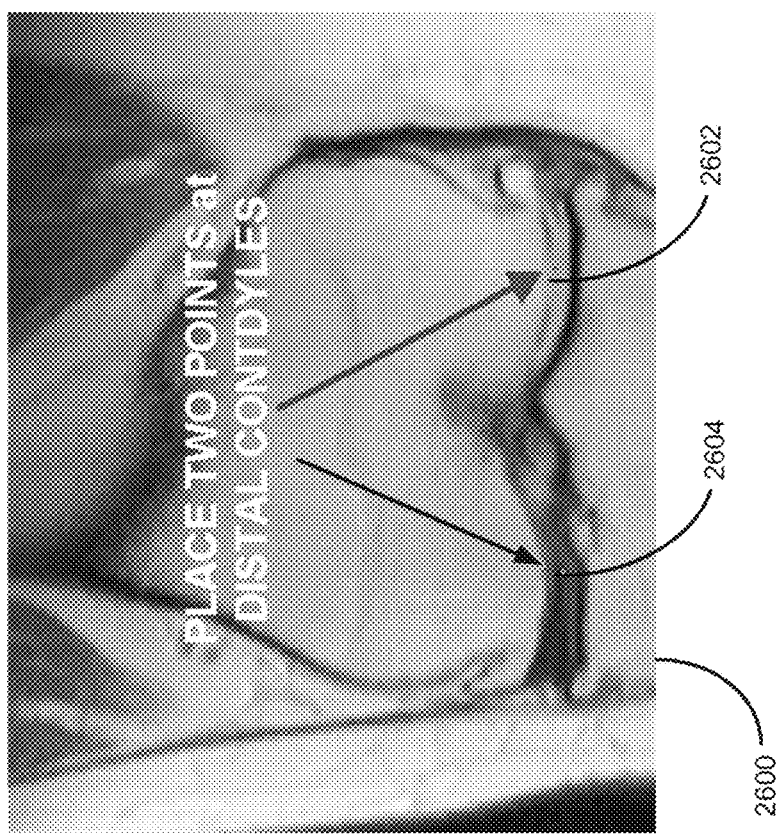
FIG. 26 is a screenshot of a coronal image of a patient's knee with a two distal condyle points of the knee identified in the image.
Figure 27:
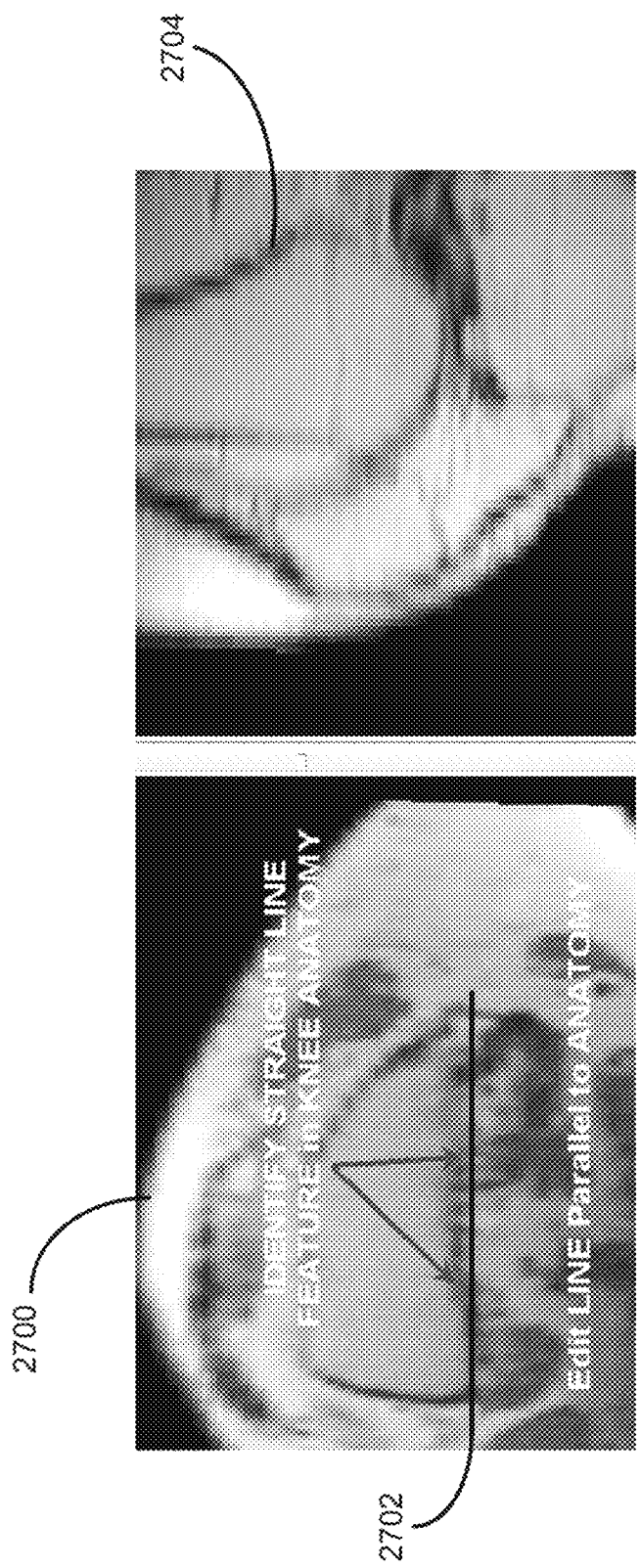
FIG. 27 is a screenshot of a coronal image of a patient's knee with an inflection point line of the knee identified in the image.
Figure 28A:
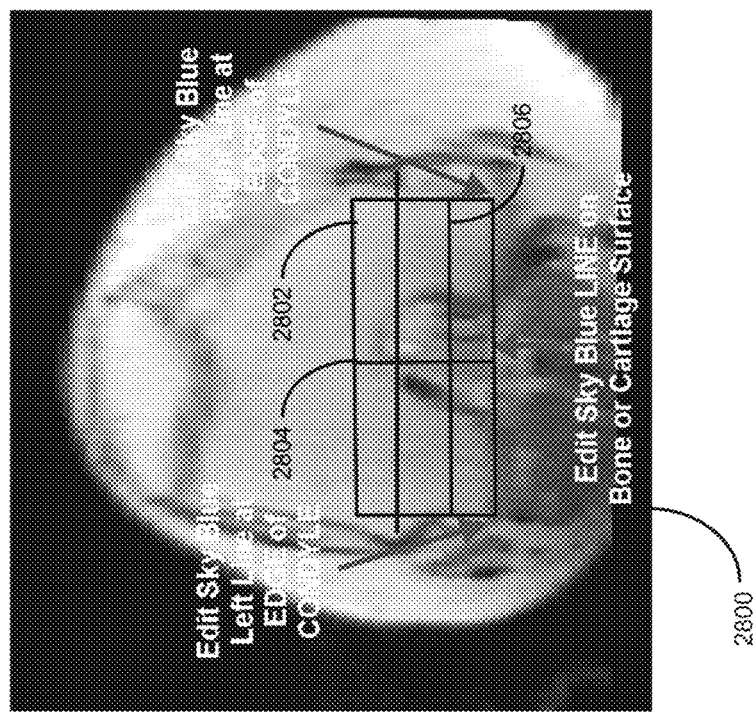
FIG. 28A-28C is a screenshot of a patient's knee with a rotation reference box of the knee identified in the image.
Figure 28B:
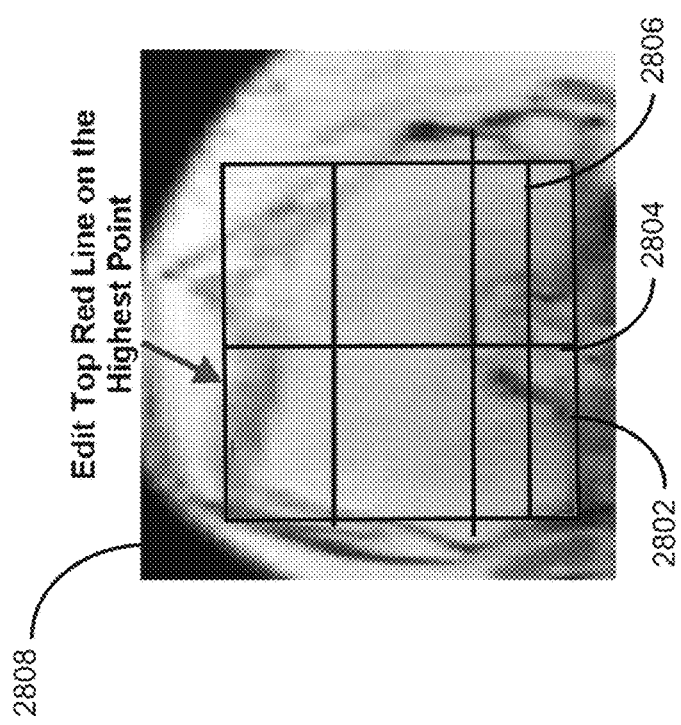
Figure 28C:
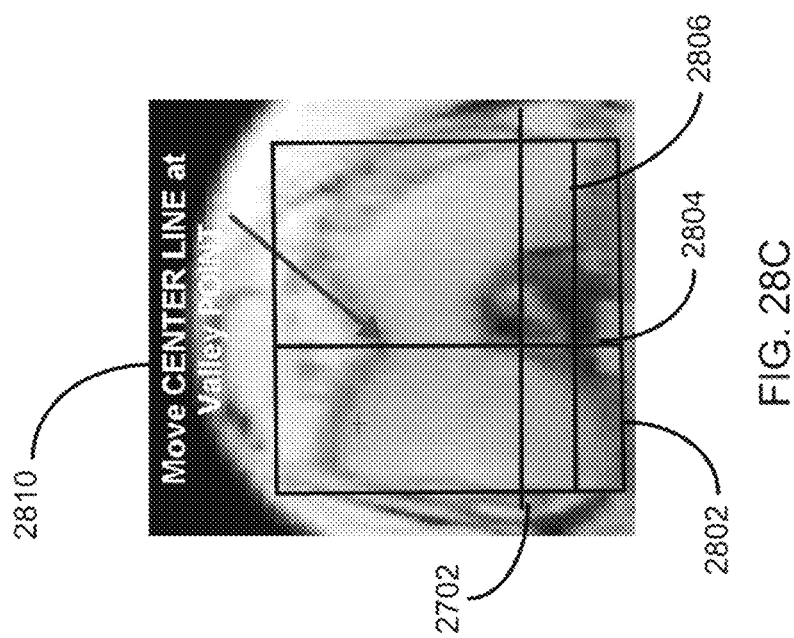

In operation 2106, the operator or computing device defines a distal reference box for the femur in the 2D images. In particular, the operator sitting in front of a monitor of the computing device selects one or more images to define a reference box. In one example, the 2D image is a coronal image near the posterior edge of the femur showing the femoral condyles. Additionally, the computing device provides a reference box for placement within the 2D image. For example, the coronal 2D image shown in the screenshot 2400 of FIG. 24 illustrates one type of reference box 2402. In particular, the reference box 2402 is a four-sided box, with two vertical internal definition lines 2404, 2406 within the reference box. Utilizing the input device, the operator positions the reference box 2402 such that the bottom edge 2408 of the reference box creates a straight line from the bottom-most point of the one femoral condyle to the bottom-most point of the other femoral condyle. In other words, the bottom edge 2408 of the reference box 2402 is positioned to define a distal femur line angle along the condyle edges in the axial 2D image of the femur. The user may also adjust, utilizing the input device, the two vertical internal definition lines 2404, 2406 of the reference box 2402. The two vertical internal definition lines 2404, 2406 may be located in the 2D image to be tangential to the inner notch of the condyles. In general, the two vertical internal definition lines 2404, 2406 of the reference box 2402 provide a reference to the edges of the inner notch between the femoral condyles. By referencing the distal reference box 2402 around the inner notch between the femoral condyles, the computing device utilizes a non-damaged portion of the femur by which the reformatting of the images may occur. Utilizing the non-damaged portion of the femur may provide a more detailed orientation of the reference box 2402. As shown in FIG. 24, vertical internal reference line 2404 is aligned on the inner edge of the left condyle and vertical internal reference line 2406 is aligned on the inner edge of the right condyle. The angle of the reference box 2402, bottom edge 2408 of the reference box, and the vertical internal definition lines 2404, 2406 may be stored by the computing device as reference markers for the 2D images for use in generating the customized cutting guide.

Further, in one embodiment, more than one 2D image may be utilized and/or selected when determining the distal reference guide. For example, a 2D image slice that is near the posterior end of the condyle (when viewing the axial image slices, an image slice near the bottom of the illustrated condyles) may be selected when adjusting the reference box 2402 angle and the two vertical internal definition lines 2404, 2406 near the edges of the inner notch between the femoral condyles. An image slice closer to the middle of the condyles when viewing the axial image slices, such as the screenshot 2500 image in FIG. 25, may be selected when adjusting the bottom side 2408 of the reference box 2402 to create a straight line from the bottom-most point of the one femoral condyle to the bottom-most point of the other femoral condyle. In another embodiment, a different 2D image slice may be selected for each placement of the angle of the reference box 2402, bottom edge 2408 of the reference box, and the vertical internal definition lines 2404, 2406. In this manner, any number of image slices may be utilized to orient the features of the reference box 2402 within the 2D images. Thus, the best fit or clearest image slices may be selected to enhance the accuracy of the reference box 2402 placement.

In operation 2108, the operator or computing device defines distal condyle points in at least one of the 2D images. Similar to above, an operator sitting in front of a monitor of the computing device selects one or more images and, utilizing the input device, provides an electronic indicator point at the bottom edge of the femoral condyles. In one embodiment, the distal condyle points are marked on a coronal image slice, such as shown in the coronal 2D image of the screenshot 2600 in FIG. 26. Further, the operator may place the distal condyle points 2602, 2604 on a cartilage surface for condyles that appear healthy and have cartilage attached and to the bone surface for condyles that are damaged and have less cartilage in the knee. The distal condyle points 2602, 2604 may provide a reference point for the computing device for ensuring a proper customized cutting guide fit from the 2D images.

Similarly, in operation 2110, the operator or computing device may define an inflection point line in at least one of the 2D images. In particular, an operator sitting in front of a monitor of the computing device selects one or more images (such as a sagittal image) and, utilizing the input device, provides an electronic indicator point at the inflection point, or the location on the femur where there is a sudden change in the slope of the bone surface. Then, in an axial view that corresponds to the noted inflection point, the operator may orient a straight line along the anatomy of the knee. For example, as shown in the 2D image of the screenshot 2700 of FIG. 27, a straight line reference 2702 is oriented along the anatomy of the knee is located on the image. The straight line reference 2702 may provide a reference point for the computing device for ensuring a proper customized cutting guide fit from the 2D images.

In one embodiment, the straight line reference 2702 is located along a rotation of axis line 2704 of the femoral notch and the condyles of the femur. In particular, the rotation of axis 2704 may be located at the inflection point of the posterior portion of the knee, at the base of the trochlear groove. This axis of rotation 2704 is seen in the sagittal view of the femur in FIG. 27. As such, the straight line reference 2702 may be a line that coincides with the axis of rotation 2704 line of the patient's femur. Again, this location is in an un-damaged area of the femur to provide for a clear location of the straight line reference 2702.

Continuing on to operation 2112, the operator or computing device defines an internal rotation/external rotation (IR/ER) box for the femur in the 2D images. In particular, the operator sitting in front of a monitor of the computing device selects one or more images, such as an axial image slice located near the posterior edge of the femoral condyles. In this image slice, the reference box appears on the computing device screen. In the example illustrated the 2D image in the screenshot 2800 in FIG. 28A, the reference box 2802 is a four-sided box, with a vertical internal definition line 2804 and a horizontal internal definition line 2806 within the reference box. With the axial 2D image slice selected, the operator, utilizing the input device, positions the left border of the reference box 2802 to align with the outer edge of the left condyle in the image. Similarly, the right border of the reference box 2802 is aligned with the outer edge of the right condyle in the image. Also, the bottom border of the reference box 2802 is aligned along the lower edges of the two condyles. As should be appreciated, the left and right borders of the reference box 2802 now approximate the medial-lateral length of the knee in the 2D images.

Although additional modifications to the reference box 2802 may be conducted with reference to the selected 2D image, in one embodiment, one or more additional 2D images are selected to which the reference box is manipulated. For example, the operator may select another axial image slice located near the anterior edge of the patient's knee for further refinement of the reference box 2802. With this image selected, the operator may orient the upper border of the reference box 2802 to align with the highest point (most anterior point) in the 2D image. One example of the modification of the reference box 2802 manipulated in this manner to define the upper boundary of the box is shown in the 2D image in the screenshot 2808 of FIG. 28B. As should be appreciated, the upper and bottom borders of the reference box 2802 now approximate the anterior-posterior length of the knee in the 2D images.

Using the same or a different image slice, the operator may utilize the reference box 2802 to indicate the center of the trochlear groove of the knee. In particular and shown in the image of the screenshot 2810 of FIG. 28C, the internal vertical reference line 2804 of the reference box 2802 is selected by the operator and located at or near the center line of the trochlear valley. Finally, the reference box 2802 may be rotated by the operator or computing device to balance the box based on the trochlear groove shape. In general, the reference box 2802 is balanced on the trochlear groove shape when it appears that the internal vertical reference line of the reference box bisects the peaks of the trochlear groove through the valley center. Additionally, the inflection point line 2702 defined above may also be shown on the monitor of the computing device as a reference guide. In general, the inflection point line 2702 may be used by the operator or computing device as a reference line to ensure that proper alignment and selection of landmarks in the 2D images has been proper. As such, if the internal horizontal reference line 2806 of the reference box 2802 crosses the inflection point line 2702, then the reference box is out of alignment. This may be the case when the selected landmarks are incorrect or the 2D images are not properly aligned. In these cases, the operator may restart the process or reject the 2D images outright. The various parameters of the reference box 2802 may then be stored by the computing device as reference markers for the 2D images for use in generating the customized cutting guide.

Through the operations of FIG. 21, the reference lines for reformatting the 2D images may be obtained by placing electronic markers on the 2D images of the patient's joint, and in particular on the patient's femur. For example, the rotation of axis line 2702 is oriented in the image to be parallel to the femur distal line defined above. In addition, the center line of the trochlear groove may be perpendicular to rotation of axis line and the femur distal reference line. These constraints in the location and orientation of the reference lines may be based at least on the parameters of the cutting jig to be created from the reformatted 2D images. Also, with these reference lines (and any other landmark identified above), the 2D images may be further reformatted to approximate or align with the patient's true anatomical coordinate system.

Figure 29:
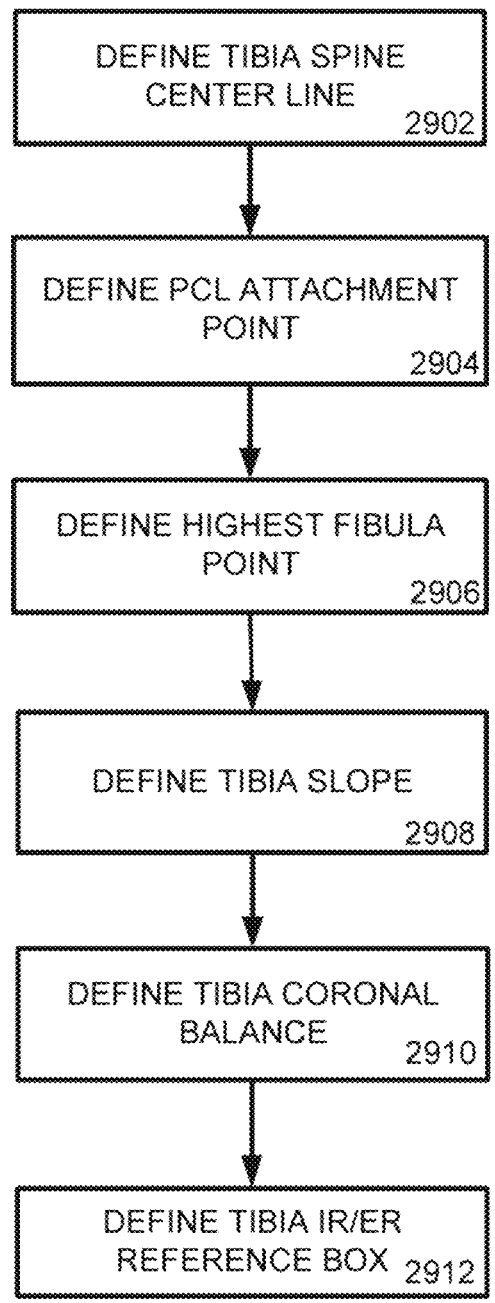
FIG. 29 is a flowchart illustrating a method for a planning stage for a customized arthroplasty cutting jig based on a series of two-dimensional images of a patient's joint to identify one or more landmarks on a patient's tibia in preparation for creating the cutting jig template for the tibia.

The planning stage of the 2D images may also include a planning stage for the tibia portion of the patient's knee. FIG. 29 is a flowchart illustrating a method for a planning stage for a customized arthroplasty cutting guide on a series of two-dimensional images of a patient's joint to identify one or more landmarks on a patient's tibia in preparation for creating the cutting guide template for the tibia. The operations detailed in FIG. 29 may also be performed as part of operation 606 described above with relation to FIG. 6. As such, the operations may be performed by an operator of a computing device or the computing device itself through which the 2D images are available for viewing, alterable, and available for locating electronic markers within the images Similar to the operations described above in relation to the method of FIG. 21, the operations of the method of FIG. 29 involve the operator or computing device analyzing the series of 2D images, selecting one or more of the 2D images, and utilizing an input device to the computing device to mark a point, line, or box in the images. The point, line, and/or box may be used by the computing device in the process of creating a customized arthroplasty cutting jig for the patient's tibia. In particular, the marker points, lines, and boxes defined in the images in the operations of FIG. 29 provide a pre-planning stage to the customized cutting guide that is used by the computing device to reformat the coordinate system of the images into a coordinate system that approximates the true anatomical coordinate system for the patient's joint. In general, the planning stage of the customized cutting jig provides reference information to the computing device in preparation for generating the customized cutting jig milling program by reformatting the 2D images that are utilized to design the cutting jig.

Beginning in operation 2902, the operator or computing device may identify the tibia spine center in one of the 2D images. In particular, an operator sitting in front of a monitor of the computing device tabs through the various coronal 2D images to select one where it appears the peak and valley feature of the tibia is present. One example of such a coronal 2D image is illustrated in the screenshot 3000 in FIG. 30. Once the image is selected, a u-shaped reference marker 3002 is present on the computing device monitor on or with the selected 2D image. The operator then utilizes the input device (such as a mouse or a keyboard) to the computing device to align the right line of the u-shaped reference marker 3002 with the medial side peak on the tibia and to align the left line of the u-shaped reference marker with the valley on the tibia feature. The electronic marking of the medial tibia peak and the tibia valley is then stored in the computing device for reference.

Figure 30:
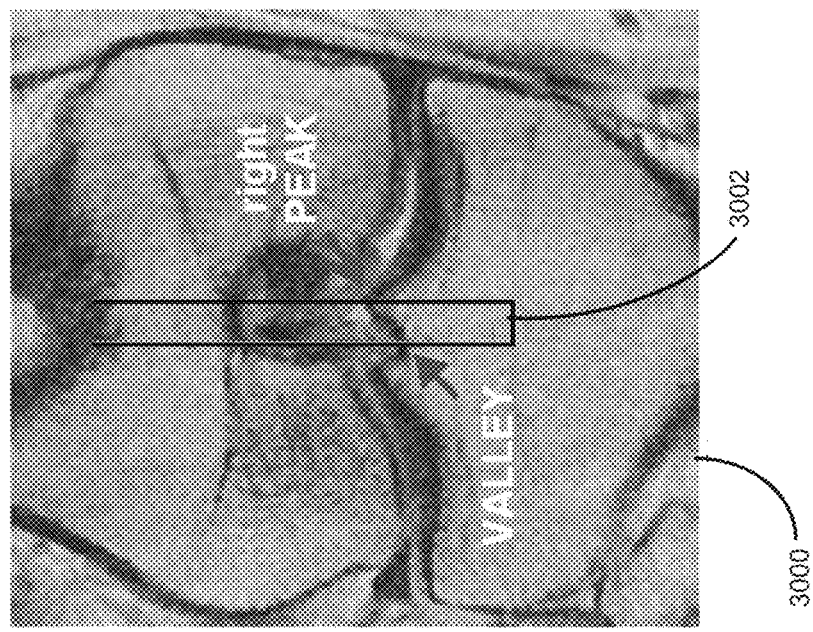
FIG. 30 is a screenshot of a coronal image of a patient's knee with tibia spine feature of the knee identified in the image.
Figure 31:
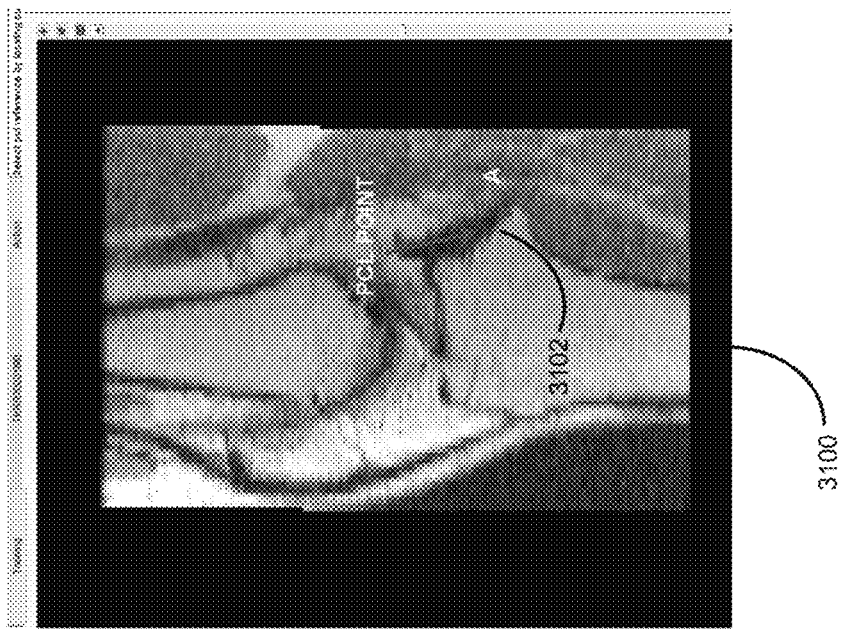
FIG. 31 is a screenshot of a sagittal image of a patient's knee with an attachment location of the posterior cruciate ligament of the knee identified in the image.
Figure 32:
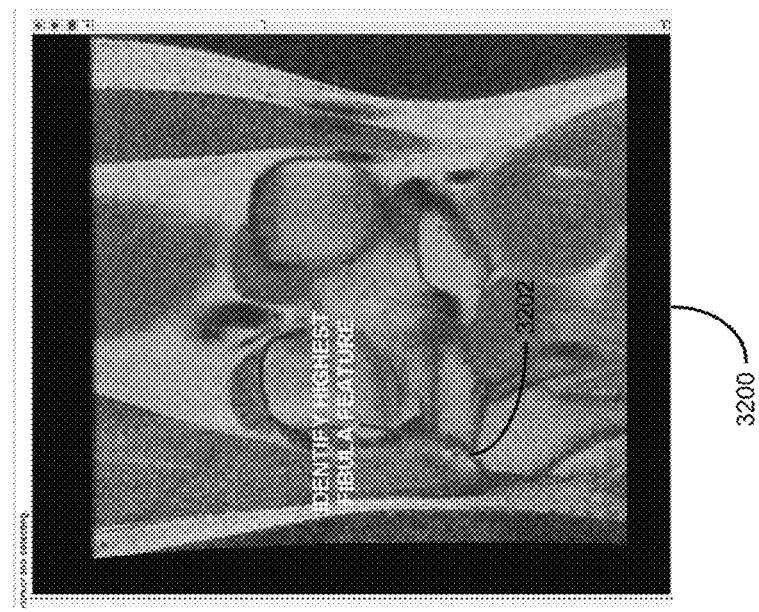
FIG. 32 is a screenshot of a coronal image of a patient's knee with a highest fibula attachment to the tibia location of the knee identified in the image.
Figure 33A:
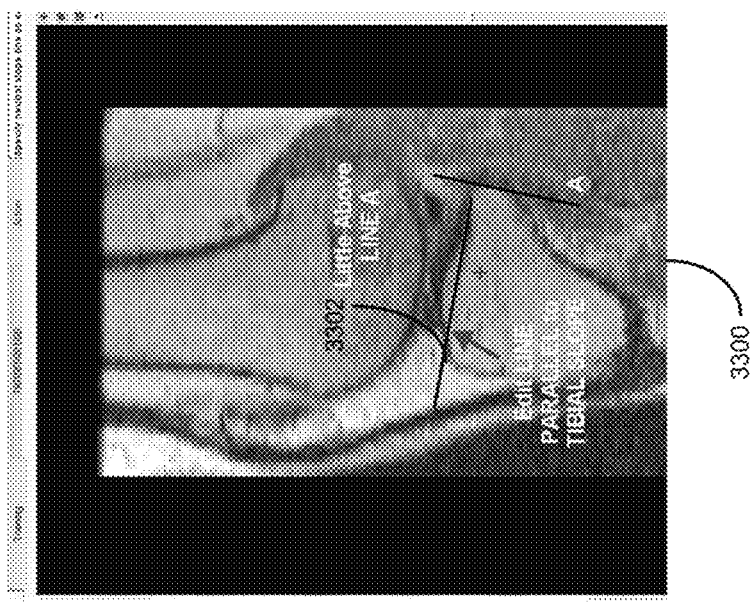
FIGS. 33A and 33B are screenshots of images of a patient's knee with tibia plateau slope of the knee identified in the images.
Figure 33B:
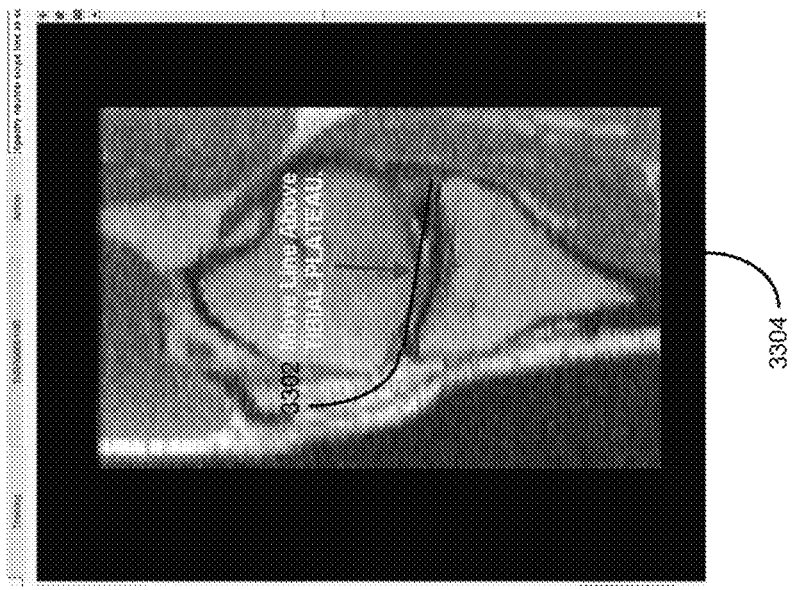

In one embodiment, the location of the u-shaped reference marker 3002, such as that shown in FIG. 30, may be located on more than one coronal image slice. Thus, in this embodiment, the operator may select a different 2D coronal image slice that shows the peak and valley feature of the tibia and orients the right and left lines of the u-shaped reference marker as discussed above. This process may be repeated as many times as desired to create several references to the peak and valley of the tibia of the 2D images.

Returning to FIG. 29, the operator or computing device defines a posterior cruciate ligament (PCL) attachment position on the tibia in operation 2904. In particular, an operator sitting in front of a monitor of the computing device selects one or more images and, utilizing the input device, identifies the position where the PCL attaches to the tibia and places an electronic marker on the position. One example of the PCL attachment marker 3102 in the image is shown in the screenshot 3100 of FIG. 31. The position may be slightly above the outer edge of the tibia. In this manner, the PCL attachment location in the 2D images is represented on the selected 2D image and is noted by the computing device for ensuring a proper customized cutting guide fit from the 2D images.

In operation 2906, the operator or computing device defines the highest fibular feature in the 2D images. In particular, an operator sitting in front of a monitor of the computing device tabs through the set of 2D coronal images and selects the one or more images that includes the highest fibula feature. Then, utilizing the input device, the operator places a location marker on the 2D image corresponding to or approximating the highest fibula feature in the 2D images. One such position 3202 is shown in the image of the screenshot 3200 of FIG. 32. The highest fibula feature position identified may provide the computing device with a lower boundary for the tibia cutting guide. The lower boundary for the tibia cutting guide ensures that the resection of the tibia obtained through the use of the tibia cutting guide does not resect any portion of the fibula.

In operation 2908, the operator or computing device defines a tibia slope in the 2D images. In particular, the operator sitting in front of a monitor of the computing device selects one or more 2D sagittal images of the knee. As shown in the screenshot 3300 of FIG. 33A, the operator utilizes the input device to define a slope line 3302 along the anterior-posterior tibia surface on the 2D image. Similar to the reference markers above, the tibia slope line 3302 may be an approximate of the actual tibia slope. In addition, the length of the tibia slope line 3302 may be manipulated by the operator (or computing device) so that the line does not extend past the outer edges of the anterior-posterior length of the tibia. Finally, the tibia slope line 3302, once oriented along the tibia slope, may be placed slightly above the tibia in the 2D image, as shown in the 2D sagittal image 3304 of FIG. 33B. The tibia slope line 3302 identified in the 2D image may aid the computing device in orienting the tibia cutting guide to match the slope of the tibia as shown in the 2D images.

Figure 34A:
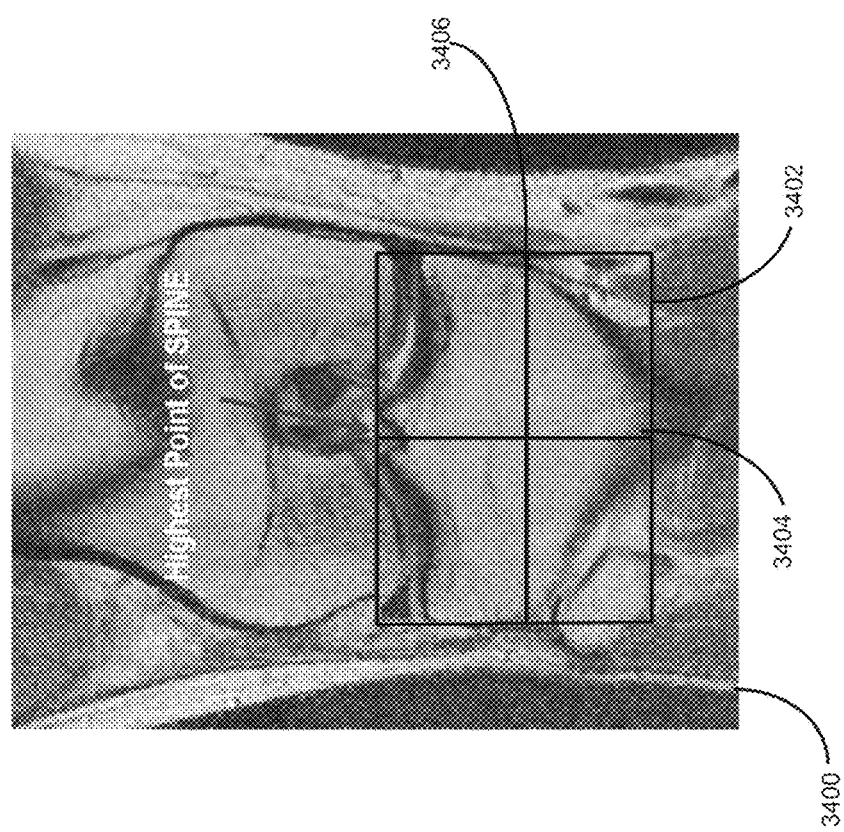
FIGS. 34A through 34C are screenshots of images of a patient's knee with a coronal balance reference box identified in the images.
Figure 34B:
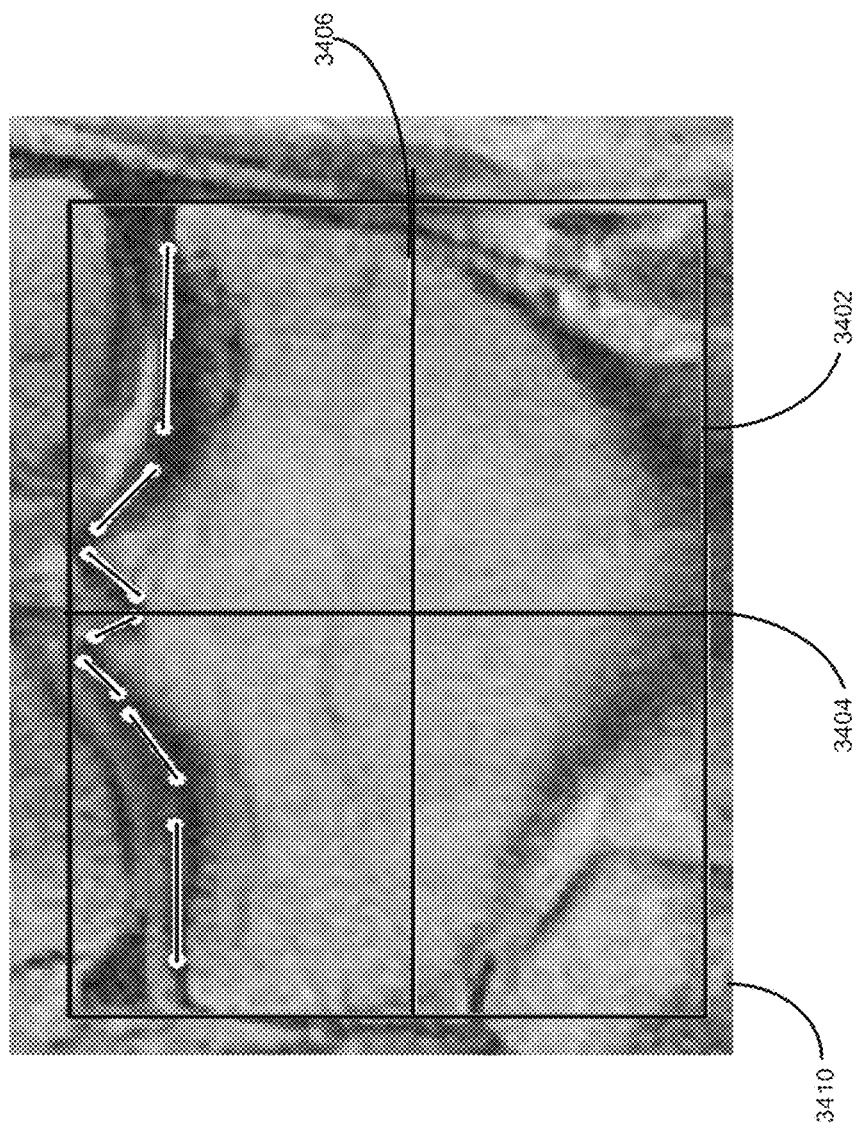

In operation 2206, the operator or computing device defines a tibia coronal balance reference box for the tibia in the 2D images. In particular, the operator sitting in front of a monitor of the computing device selects one or more 2D coronal images of the tibia. In one embodiment, the selected 2D image includes the highest tibia spine feature. Additionally, the computing device provides a reference box for placement within the 2D image. For example, the 2D image shown in the screenshot 3400 in FIG. 34A illustrates one type of reference box 3402. In particular, the reference box 3402 is a four-sided box, with a vertical internal definition line 3404 and a horizontal internal definition line 3406 within the reference box. Utilizing the input device, the operator positions the upper edge of the reference box 3402 to sit at or above the highest point of the tibia spine. Also, the operator positions the vertical internal definition line 3404 to align with the middle of the valley feature of the tibia spine. The reference box 3402 may further be rotated by the operator or computing device to balance the box based on the spine feature of the tibia. In general, the reference box 3402 is balanced on the spine feature when it appears that the internal vertical reference line of the reference box bisects the peaks of the spine feature through the valley center. An example of a balanced reference box 3402 on the spine feature of the tibia is shown in the screenshot 3410 of FIG. 34B. When the reference box 3402 is balanced, the left edge of the reference box should closely align with the left bone edge of the tibia in the 2D image.

Figure 34C:
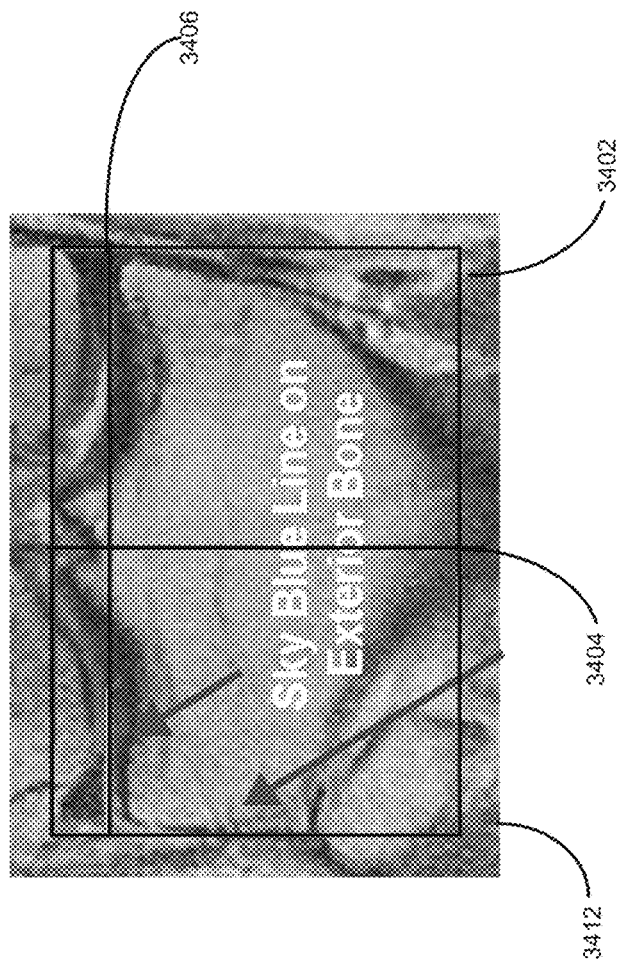
Figure 35A:
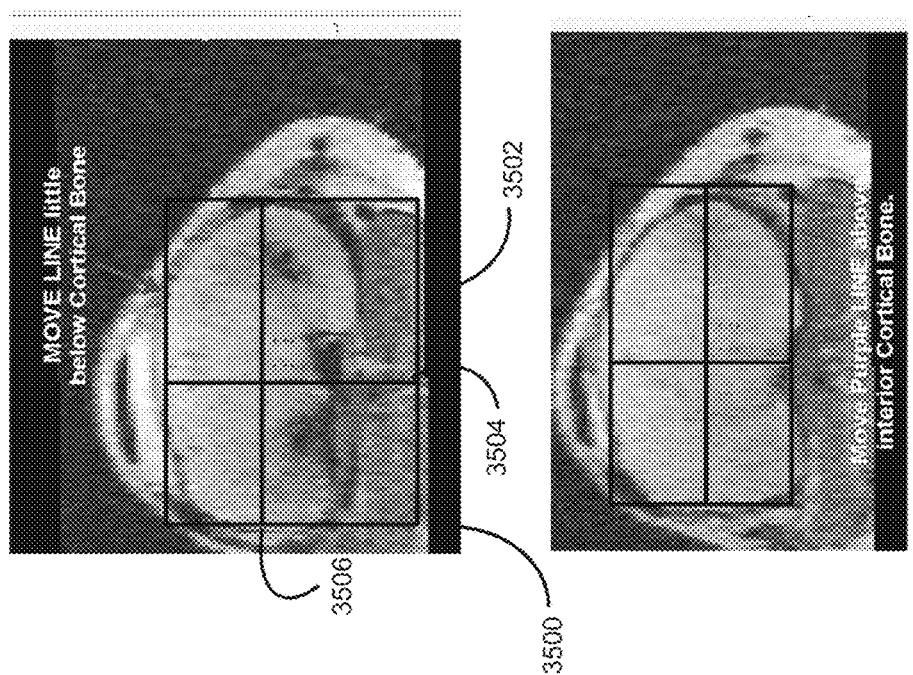
FIGS. 35A through 35C are screenshots of images of a patient's knee with a rotation angle reference box identified in the images.
Figure 35B:
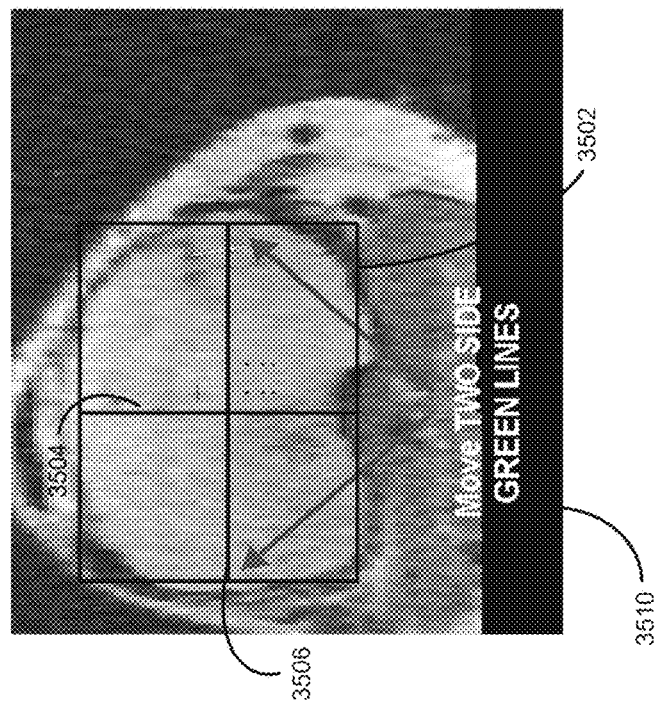
Figure 35C:
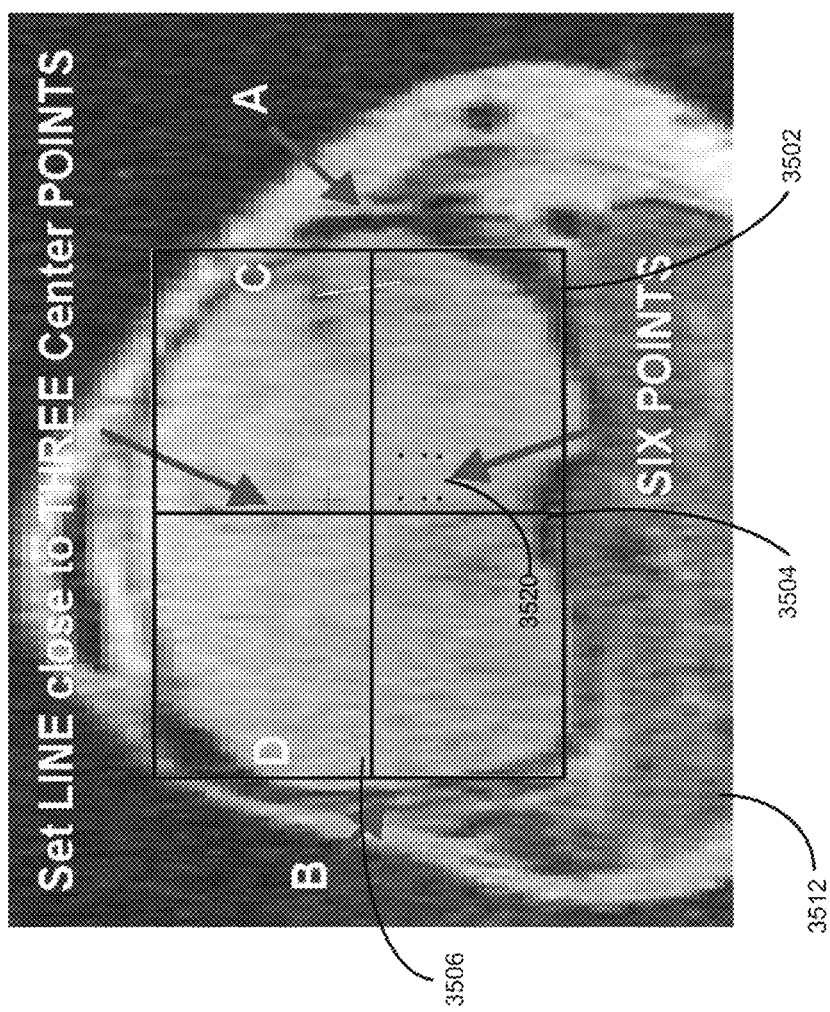
Figure 36:
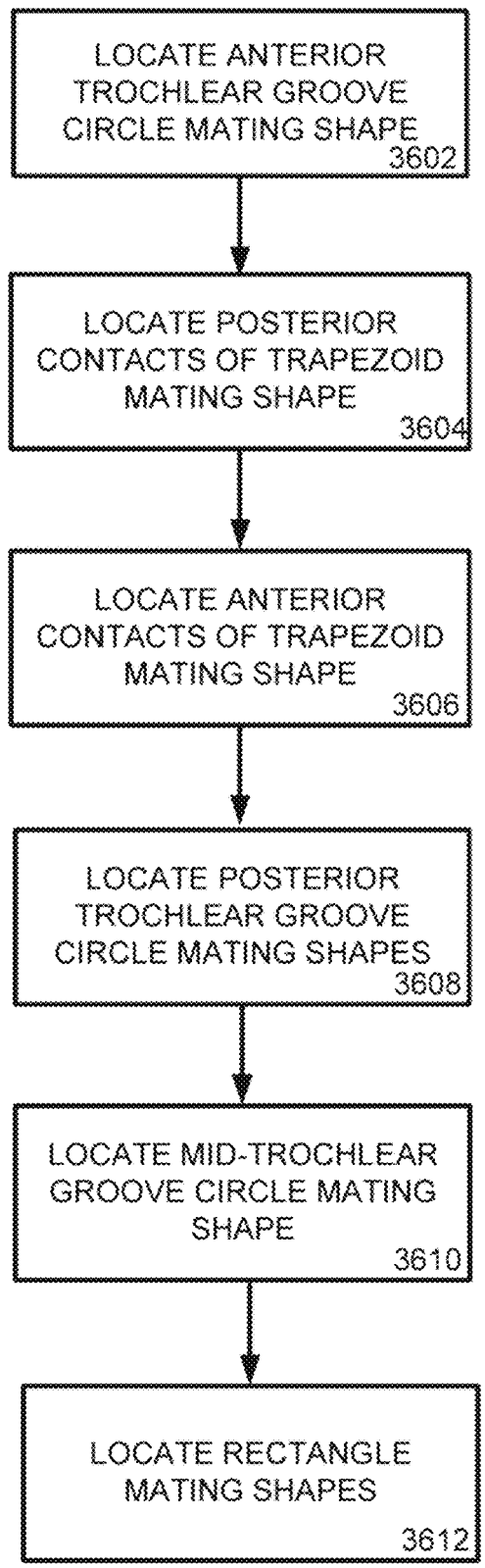
FIG. 36 is a flowchart illustrating a method for a template design stage for a customized arthroplasty cutting jig based on a series of two-dimensional images of a patient's joint to locate one or more contact surfaces of the cutting jig to one or more landmarks of the patient's femur.

The user may also adjust, utilizing the input device, the horizontal internal definition line 3406 of the reference box 3402, as shown in the screenshot 3412 of FIG. 34C. In particular, the horizontal internal definition line 3406 may be placed by the operator to the top of the exterior cortical bone of the tibia plateau. In one embodiment, the location of the horizontal internal definition line 3406 is along the undamaged side of the tibia plateau. As such, the specific location and orientation of the tibia coronal balance reference box 3402 may be stored by the computing device as reference markers for the 2D images for use in generating the customized tibia cutting jig.

Continuing on to operation 2912, the operator or computing device defines an internal rotation/external rotation (IR/ER) reference box for the tibia in the 2D images. In particular, the operator sitting in front of a monitor of the computing device selects one or more images, such as an axial image slice located near the anterior wall of the tibia. In this image slice, a reference box appears on the computing device screen. In the example image illustrated in the screenshot 3500 of FIG. 35A, the reference box 3502 is a four-sided box, with a vertical internal definition line 3504 and a horizontal internal definition line 3506 within the reference box. With the axial 2D image slice selected, the operator, utilizing the input device, positions the upper border of the reference box 3502 to slightly below the upper edge of the interior cortical bone in the 2D axial image of the tibia. Similarly, the lower border of the reference box 3502 is positioned by the operator or computing device slightly above the lower edge of the interior cortical bone in the 2D axial image of the tibia. As should be appreciated, the upper and lower borders of the reference box 3502 now approximate the anterior-posterior length of the tibia in the 2D image.

Although additional modifications to the reference box 3502 may be conducted with reference to the selected 2D image, in one embodiment, one or more additional 2D images are selected to which the reference box is manipulated. For example, the operator may select an axial image slice located near the anterior edge of the patient's tibia for to position the upper border of the reference box 3502 and select another axial image near the posterior edge of the patient's tibia to position the lower border. In general, any number of image slices located within the series of 2D image slices may be utilized to position the reference box 3502.

Additionally, the operator may select an axial 2D image at or near the center of the tibia for additional positioning of the borders and reference lines of the reference box 3502. With the axial 2D image slice selected, the operator, utilizing the input device, positions the left border of the reference box 3502 to a position slightly inside the left interior cortical bone of the tibia in the image. Similarly, the right border of the reference box 3502 is a position slightly inside the right interior cortical bone of the tibia in the image. One example of the positioning of the right and left borders of the reference box 3502 is shown in the screenshot 3510 of FIG. 35B. As should be appreciated, the left and right borders of the reference box 3502 now approximate the medial-lateral length of the tibia in the 2D images.

Using the same or a different image slice, the operator may utilize the reference box 3502 to rotate the reference box to align the box with spine feature of the tibia. In particular and shown in FIG. 35C, the image may include one or more points 3520 that indicate the location of the tibia spine determined above with reference to operation 2902. In the example shown in the screenshot 3512 of FIG. 35C, the identification of the tibia spine 3520 (and in particular, the right peak and the center valley of the spine feature) was performed three times. Thus, the axial image includes six points 3520, indicating the right peak and center valley of the tibia spine feature in the image. With these points as a reference, the operator rotates the reference box 3502 such that the internal vertical reference line 3504 of the reference box is aligned with the spine feature points 3520 in the 2D image. The various parameters of the reference box 3502 may then be stored by the computing device as reference markers for the 2D images for use in generating the customized cutting guide.

Through the operations of FIG. 29, the reference lines for reformatting the 2D images may be obtained by placing electronic markers on the 2D images of the patient's joint, and in particular on the patient's tibia. For example, the center reference line through the tibia spine is oriented in the image to be perpendicular to both the medial-lateral reference line and the anterior-posterior reference line. Similarly, the medial-lateral reference line and the anterior-posterior reference line are parallel. These constraints in the location and orientation of the reference lines may be based at least on the parameters of the cutting jig to be created from the reformatted 2D images. Also, with these reference lines (and any other landmark identified above), the 2D images may be further reformatted to approximate or align with the patient's true anatomical coordinate system.

With the completion of the reformatting stage and the planning stage, the operator or computing device may begin the template design phase for the arthroplasty cutting jigs. In particular, the information determined in the reformatting stage and the planning stage may be utilized by the computing device when generating the templates for the cutting jigs. Further, the operator or computing device may perform one or more of the operations illustrated in FIG. 36 to determine the shape of the cutting jig. Through the template design process, one or more mating surfaces or points of the cutting jig may be determined by the computing device and/or the operator. These mating surfaces or points are then translated into the milling program for milling or cutting the specific, customized cutting jigs from the jig blanks. In this manner, the information determined during the template design stage of the cutting guide design method results in the creation of one or more customized arthroplasty cutting guides or jigs based on the 2D images of a particular patient's joint. The operations detailed in FIG. 36 may be performed as operation 608 described above with relation to FIG. 6. As such, the operations may be performed by an operator of a computing device or the computing device itself through which the 2D images are available for viewing, alterable, and available for identifying landmarks within the images.

Similar to the operations described above, the operations of the method of FIG. 36 involve the operator or computing device analyzing the 2D images, selecting one or more of the 2D images and utilizing an input device to the computing device to define a shape in the images. In particular, the computing device provides a shape on the selected image that corresponds to a surface shape of a customized cutting guide. The operator (or computing device) utilizes an input device to the computing device to locate the provided shape on the 2D image.

Figure 37:
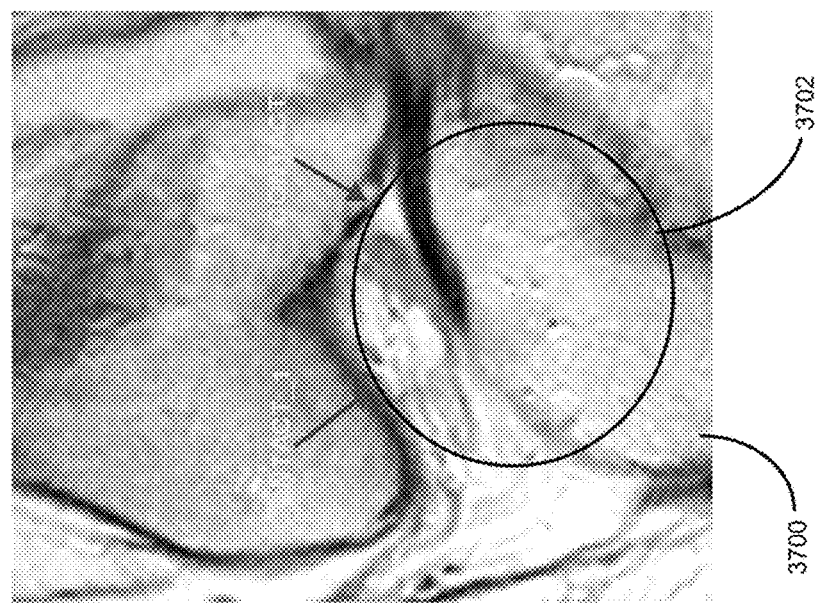
FIG. 37 is a screenshot of a coronal image of a patient's knee with a location of an anterior trochlear groove circle mating shape identified in the image.

Beginning in operation 3602, the operator or computing device may place an anterior trochlear groove circular shape in one of the 2D images. As explained in more detail below, this shape corresponds to a circular mating surface of a customized femoral cutting jig that contacts the femur in the anterior portion of the trochlear groove. Thus, the placement of the circular shape in the 2D images may be translated to a milling program that creates the same or a similar shape in a customized femoral cutting guide for use in an arthroplasty procedure. In one embodiment, an operator sitting in front of a monitor of the computing device tabs through the various axial 2D images of the patient's knee to select an image for placement of the trochlear groove circular shape. In one particular example, the selected image is a coronal image slice lying between the anterior cortex point of the femur and the bottom or valley of the trochlear groove identified above in the planning stage. Once the image is selected, the computing device provides a circular shape on the 2D image that is adjustable by the operator. An example of the circular shape 3702 provided in the coronal 2D image is shown in the screenshot 3700 of FIG. 37. The operator may then utilize the input device to the computing device to move the circular shape 3702 within the 2D image. In particular, the circle shape 3702 is placed in the 2D image such that the circle contacts the two femoral condyles within the trochlear groove shown in the 2D coronal image. As shown in FIG. 37, the circle shape 3702 thus creates two contact points with the femur. The computing device may then utilize the placement information of the circular shape in the 2D image and may translate that placement into the anterior trochlear groove circular shape feature of the customized femoral cutting jig described below.

In operation 3604, the operator or computing device may locate posterior contacts of a trochlear groove trapezoidal mating shape in one of the 2D images. As explained in more detail below, this shape corresponds to a pair of surface contacts of a customized femoral cutting jig that contact the patient's femur on the condyles. Thus, the location of the posterior contacts of a trochlear groove trapezoidal mating shape in the 2D images may be translated to a milling program that creates a mating surface on a customized femoral cutting jig for use in an arthroplasty procedure that corresponds to the placement of the posterior contacts. In this manner, the posterior contacts of a trochlear groove trapezoidal mating shape is customized to the patient's femur as captured in the 2D images of the joint.

Figure 38A:
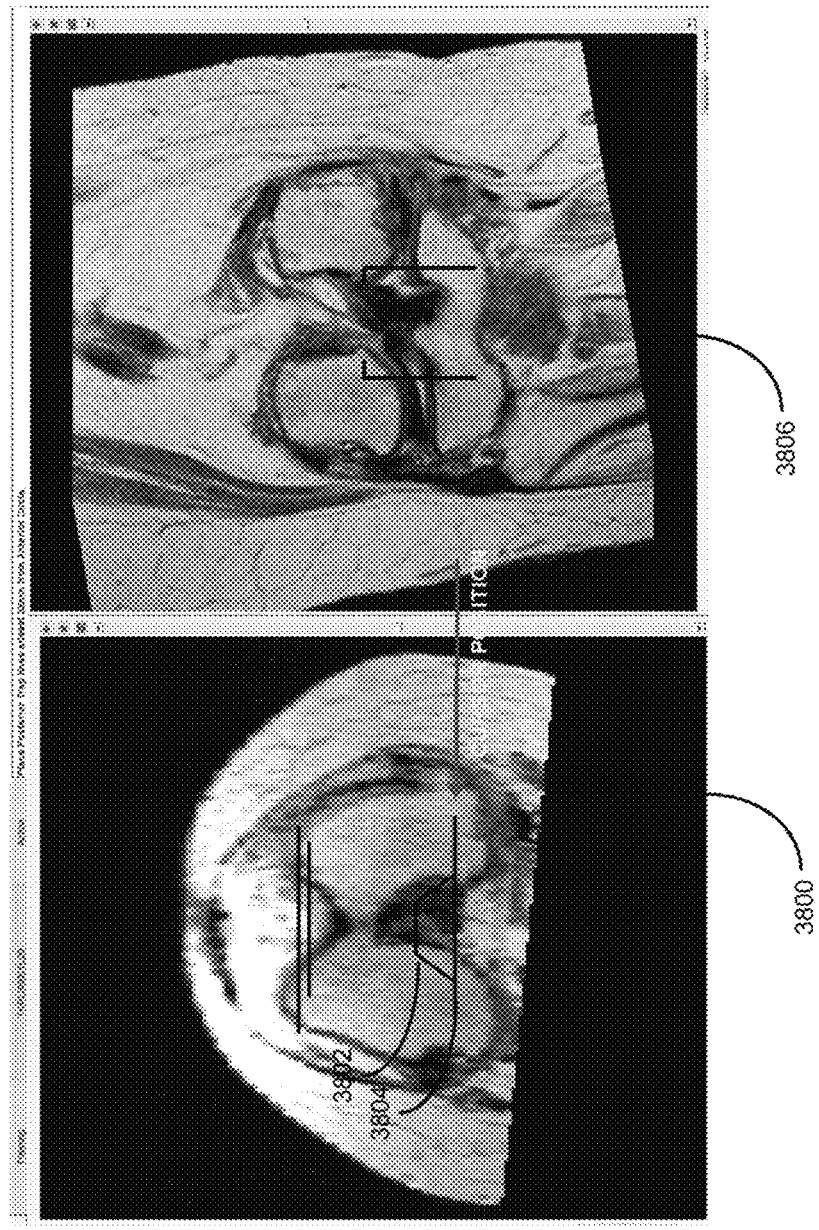
FIGS. 38A and 38B are screenshots of images of a patient's knee with a location of posterior contacts of a trapezoidal mating shape identified in the image.
Figure 38B:
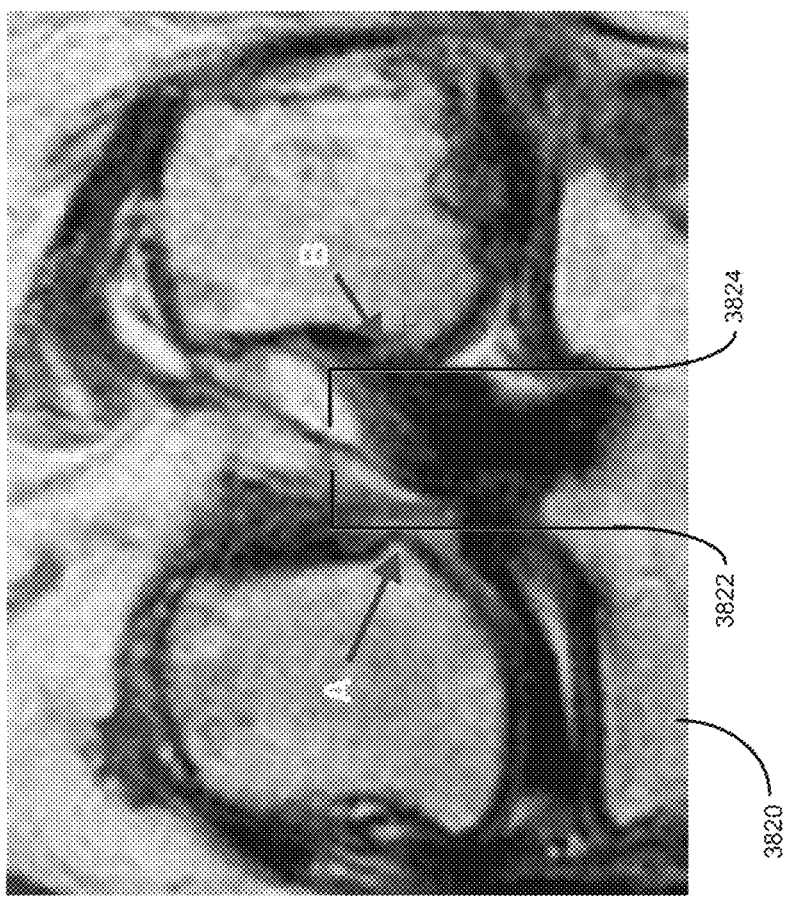

In one embodiment, as shown in the screenshot 3800 of FIG. 38A, the computing device may provide an axial image to the operator. The provided image may also include a trapezoidal shape 3802 that approximates the trapezoidal mating shape of the customized cutting jig discussed above. In other words, the computing device may utilize the information provided in the reorienting and planning stages discussed above to estimate the location of the trapezoidal mating shape of the cutting jig. In particular, the computing device may approximately determine the location of the trochlear groove based on the landmarks noted above and provide a suggested location for the trapezoidal mating shape 3802, including the estimated location of the bottom edge 3804 of the trapezoidal mating surface. Thus, the particular axial image slice provided to the operator corresponds to the bottom edge 3804 of the suggested trapezoidal mating shape 3802 location. Further, the computing device also provides a coronal image 3806 that corresponds to the selected axial image 3800. In one embodiment, the operator is not required to use the suggested image and/or trapezoidal mating shape 3802 location, but rather may adjust the particular axial and coronal image used to place the bottom edge 3804 of the trapezoidal shape.

To adjust the length and placement of the bottom edge 3804 of the trochlear groove trapezoidal shape 3802, a pair of adjustable straight line features may be provided in the coronal image that corresponds to the selected axial image. As shown in the screen shot 3820 of the corresponding coronal image in FIG. 38B, the two straight line features 3822, 3824 may be in the form of two upside-down "L" shapes. To adjust the bottom edge of the trochlear groove trapezoidal shape 3802, the operator may move the left straight line feature 3822 to be tangential to the inner surface of the left condyle that forms a surface of the trochlear groove shown in the 2D image. Similarly, the operator may move the right straight line feature 3824 to be tangential to the inner surface of the right condyle that forms a surface of the trochlear groove. The placement of these straight line features 3822, 3824 acts to adjust the length of the bottom edge 3804 of the trochlear groove trapezoidal shape 3802 to fit within the trochlear groove shown in the 2D images. The computing device may then utilize the placement information of the two straight line features 3822, 3824 in the 2D image and translate that placement into the posterior contacts of a trochlear groove trapezoidal mating shape feature of the customized femoral cutting jig described below.

In a similar manner, the operator or computing device may locate anterior contacts of a trochlear groove trapezoidal mating shape in one of the 2D images in operation 3606. The location of the anterior contacts in the 2D images may also be translated to a milling program that creates a mating surface on a customized femoral cutting jig for use in an arthroplasty procedure that corresponds to the placement of the anterior contacts. In this manner, the anterior contacts of a trochlear groove trapezoidal mating shape is customized to the patient's femur as captured in the 2D images of the joint.

As similar to above, the computing device may provide an axial image (image 3800 as seen in FIG. 38A) to the operator that includes the trapezoidal shape that approximates the anterior contacts of a trochlear groove trapezoidal mating shape of the customized cutting jig. Also similar, the particular axial image slice provided to the operator may correspond to the anterior contacts or upper edge of the suggested trapezoidal mating shape location. Further, a coronal image corresponding to the selected axial image and a pair of adjustable straight line features may also be provided to the operator. As shown in the screenshot 3900 of FIG. 39, the two straight line features 3902, 3904 for the upper edge of the trapezoidal shape may be in the form of two upside-down "L" shapes. To adjust the upper edge of the trochlear groove trapezoidal shape, the operator may move the left straight line 3902 feature to be tangential to the inner surface of the left condyle that forms a surface of the trochlear groove shown in the 2D image and may move the right straight line feature 3904 to be tangential to the inner surface of the right condyle that forms a surface of the trochlear groove. The placement of these straight line features 3902, 3904 acts to adjust the length of the upper edge of the trochlear groove trapezoidal shape to fit within the trochlear groove shown in the 2D images.

Figure 39:
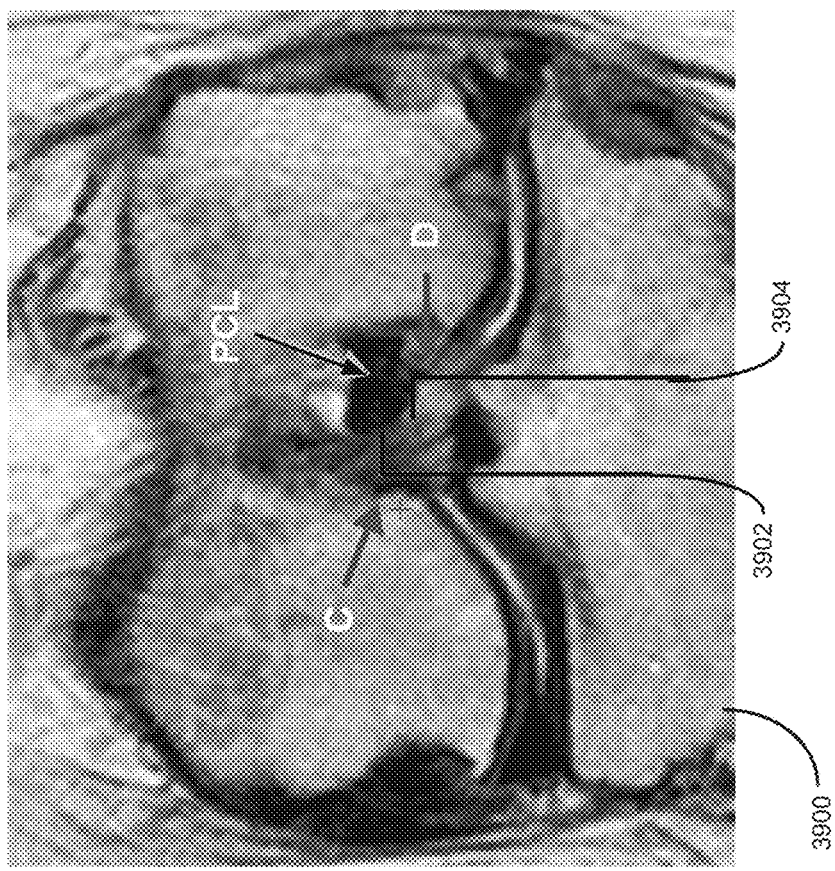
FIG. 39 is a screenshot of a coronal image of a patient's knee with a location of anterior contacts of a trapezoidal mating shape identified in the image.
Figure 40:
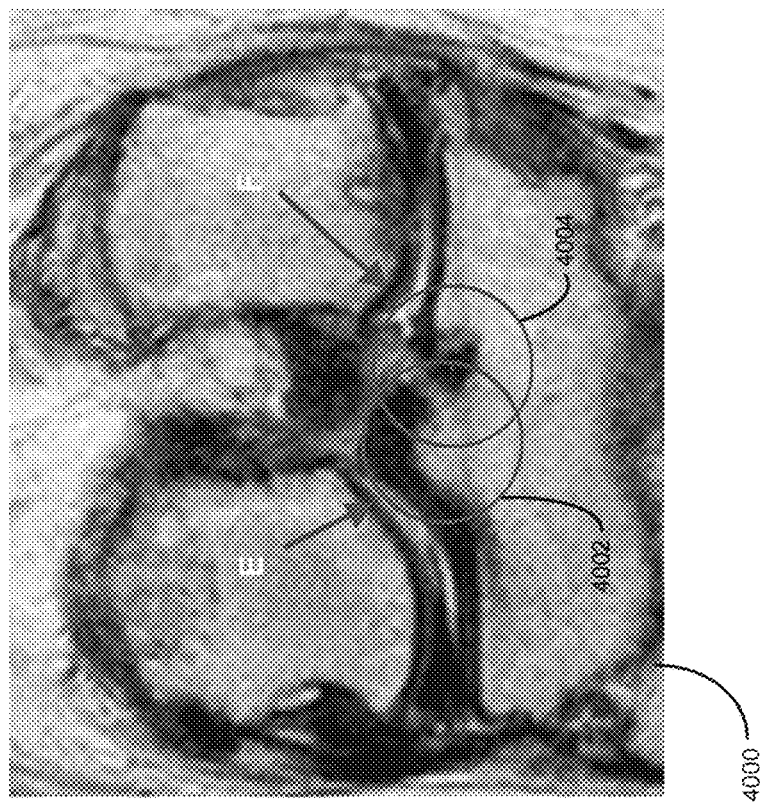
FIG. 40 is a screenshot of a coronal image of a patient's knee with a location of a pair of posterior trochlear groove circular mating shapes identified in the image.

In addition, the right straight line feature 3904 may be placed to account for the location of the PCL in the 2D image. More particularly, the right straight line feature 3904 may be positioned slightly below the PCL location to ensure that the cutting guide mates with the femur and not on the PCL. The horizontal line of the right straight line feature 3904 may indicate the upper bound of the straight line feature and may be placed below the PCL shown in the 2D image. As should be appreciated, it is not necessary that the contact points of the upper edge of the trapezoid be aligned. Rather, the contact of the upper edge of the trapezoid on the right condyle may not be aligned with the contact of the upper edge of the trapezoid on the left condyle. This is shown in FIG. 39 by the horizontal lines of the two straight line features not being aligned. Once placed, the computing device may then utilize the placement information of the two straight line features in the 2D image and translate that placement into the anterior contacts of a trochlear groove trapezoidal mating shape feature of the customized femoral cutting jig described below.

In operation 3608, the operator or computing device may place a pair of trochlear groove posterior circle shapes in one of the 2D images. As explained in more detail below, these shapes correspond to the posterior trochlear groove circle mating surfaces of a customized femoral cutting jig. Thus, the location of the pair of trochlear groove posterior circle shapes in the 2D image may be translated to a milling program that creates a mating surface on a customized femoral cutting jig for use in an arthroplasty procedure that corresponds to the placement of the posterior circles. In this manner, the pair of trochlear groove posterior circle shapes is customized to the patient's femur as captured in the 2D images of the joint.

In one embodiment, the computing device may provide an axial image to the operator that includes the trapezoidal shape discussed above. In addition, a coronal view corresponding to a position near the bottom edge of the trapezoidal shape may also be provided to the operator on the computing device monitor. Within the coronal view, the computing device provides a pair of trochlear groove posterior circle shapes within the image. Similar to the circular shape described above, the pair of trochlear groove posterior circle shapes within the 2D image may be adjustable by the operator. In particular, the operator utilizes the input device to the computing device to move the pair of trochlear groove posterior circle shapes within the 2D image. In particular, the circle shape is placed in the 2D image such that the circle contacts the two femoral condyles within the trochlear groove. As shown in the screenshot 4000 of the coronal image in FIG. 40, the pair of trochlear groove posterior circle shapes 4002, 4004 are placed in the 2D image on the inner surface of the condyles of the femur, along the trochlear groove. In this manner, the pair of trochlear groove posterior circle shapes create two contact points with the femur within the trochlear groove. The computing device may then utilize the placement information of the pair of trochlear groove posterior circle shapes in the 2D image and translate that placement into the posterior trochlear groove circle mating surfaces feature of the customized femoral cutting guide described below.

In operation 3610, the operator or computing device may place a mid-trochlear groove circle shape in one of the 2D images. This shape corresponds to a circular mating surface of a customized femoral cutting jig that contacts the femur in the middle portion of the trochlear groove when mated with the femur. Thus, the location of the mid-trochlear groove circle shape in the 2D image may be translated to a milling program that creates a mating surface on a customized femoral cutting jig for use in an arthroplasty procedure that corresponds to the placement of the mid-trochlear circle shape. In this manner, the mid-trochlear groove circle shape is customized to the patient's femur as captured in the 2D images of the joint.

Figure 41:
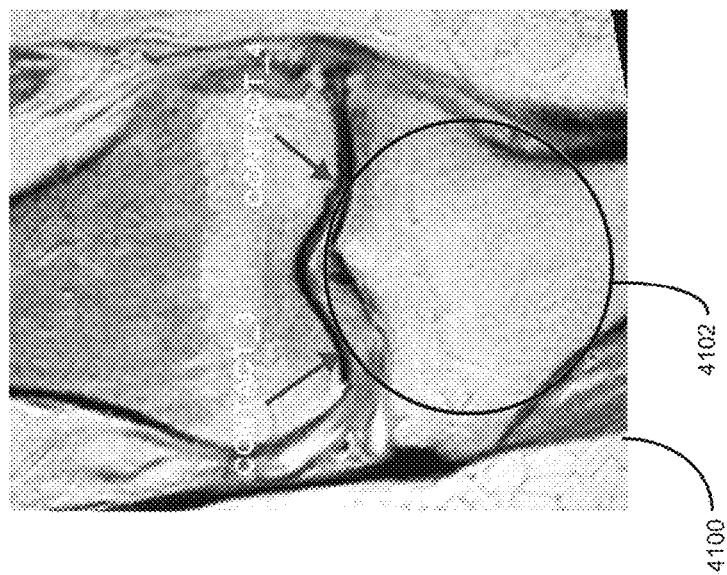
FIG. 41 is a screenshot of a coronal image of a patient's knee with a location of mid-trochlear groove circular mating shape identified in the image.

In one embodiment, the computing device may provide an axial image to the operator that is near the center axis of the femur shaft. In addition, a coronal view corresponding to the selected axial image is provided to the operator. Within the coronal view, the computing device provides a circular shape. An example of the circular shape 4102 provided in the image is shown in screenshot 4100 in FIG. 41. Similar to the circular shape described above, the mid-trochlear circular shape 4102 within the 2D image may be adjustable by the operator. Thus, the operator may utilize the input device to the computing device to move the circular shape 4102 within the 2D image such that the circle contacts the two femoral condyles within the trochlear groove. As shown in FIG. 41, the circle shape thus creates two contact points with the femur. The computing device may then utilize the placement information of the circular shape in the 2D image and translate that placement into the mid-trochlear groove circle mating surface feature of the customized femoral cutting guide described below.

In operation 3612, the operator or computing device may place a pair of rectangle shapes in one of the 2D images. As explained in more detail below, this shape corresponds to a pair of rectangular shaped mating surfaces of a customized femoral cutting jig. Thus, the location of the rectangular shapes in the 2D image may be translated to a milling program that creates a mating surface on a customized femoral cutting jig for use in an arthroplasty procedure that corresponds to the placement of the rectangular shapes in the 2D image. In this manner, the rectangular shapes are customized to the patient's femur as captured in the 2D images of the joint.

Figure 42:
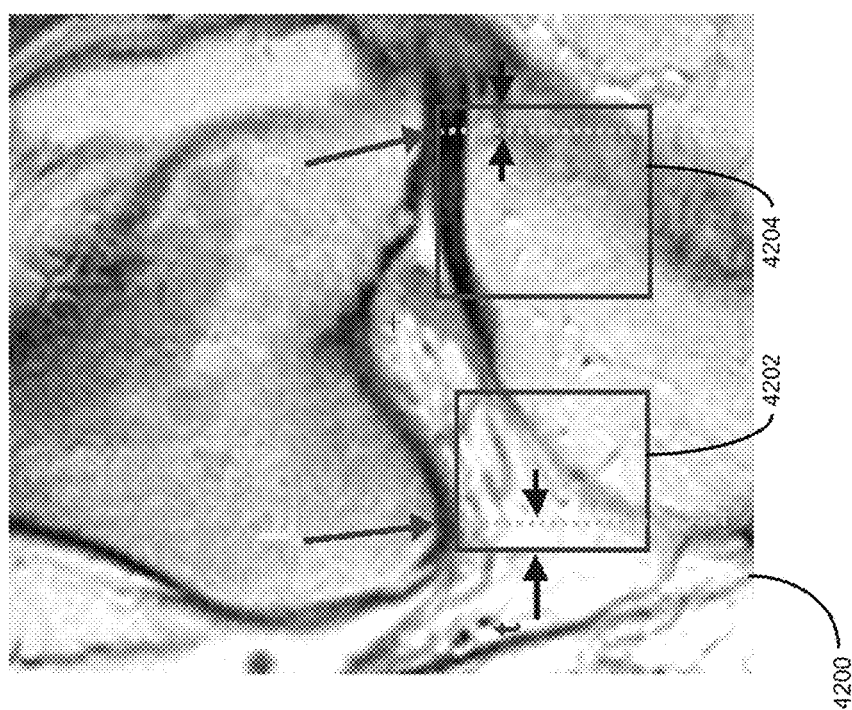
FIG. 42 is a screenshot of a coronal image of a patient's knee with a location of a pair of rectangular mating shapes identified in the image.
Figure 43:
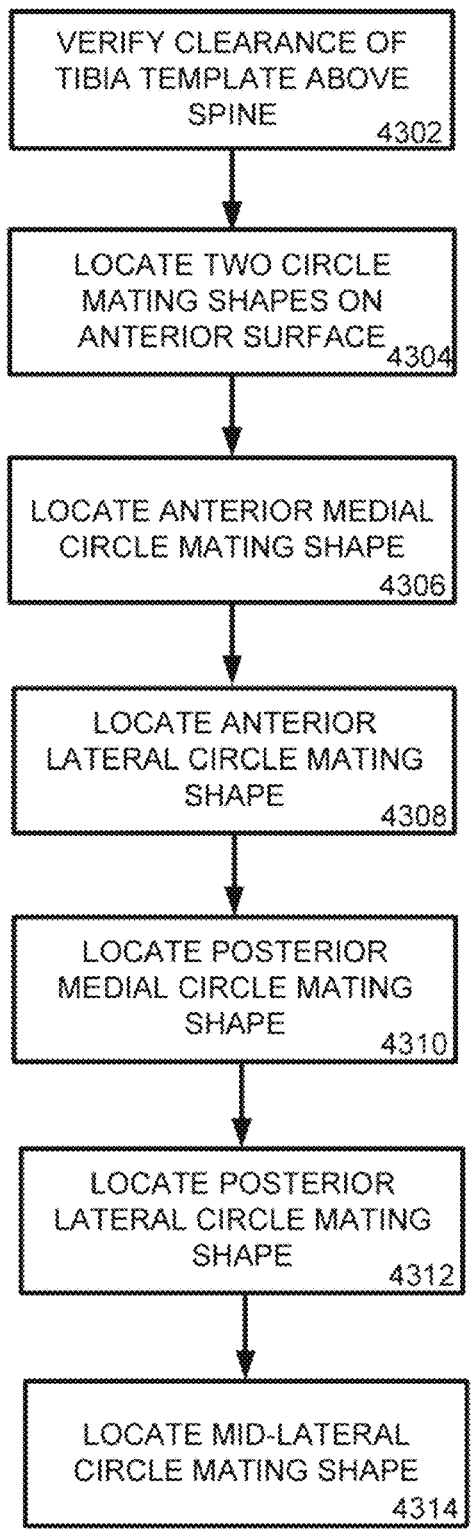
FIG. 43 is a flowchart illustrating a method for a template design stage for a customized arthroplasty cutting jig based on a series of two-dimensional images of a patient's joint to locate one or more contact surfaces of the cutting jig to one or more landmarks of the patient's tibia.
Figure 44:
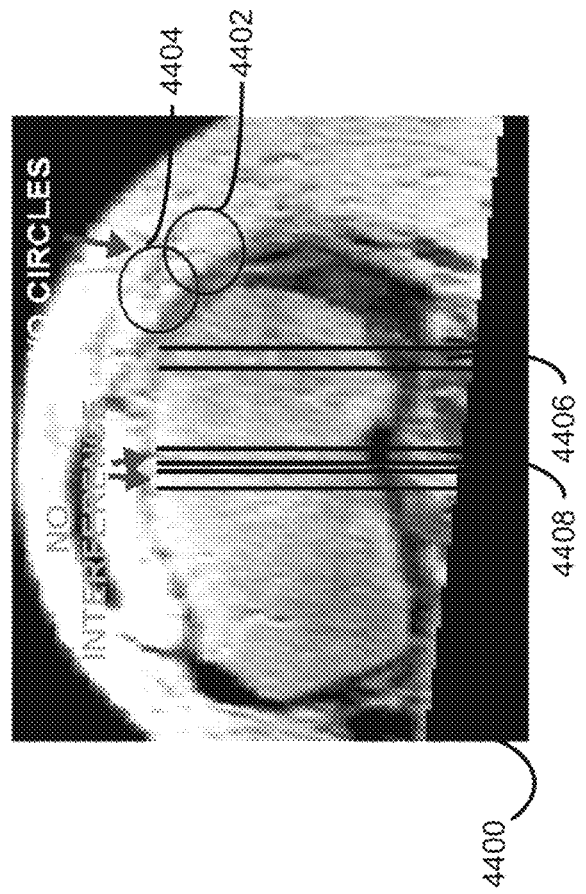
FIG. 44 is a screenshot of an axial image of a patient's knee with a location of a pair of circular mating shapes for the anterior surface of the tibia identified in the image.

In one embodiment, the computing device provides an axial image to the operator that is the same or similar to the axial image for the anterior trochlear groove circle shape discussed above. In addition, a coronal view corresponding to the selected axial image is provided to the operator. Within the coronal view, the computing device provides a pair of rectangular shapes. An example of the rectangular shapes 4202, 4204 provided in the image is shown in the screenshot 4200 of FIG. 42. Utilizing the input device to the computing device, the operator may adjust the two rectangles to correspond to landmarks in the selected 2D image. For example and as shown in FIG. 42, the left rectangular shape 4202 may be positioned within the 2D image to be tangential to the lowest point on the left femoral condyle. Similarly, the right rectangular shape 4204 may be positioned within the 2D image to be tangential to the lowest point on the right femoral condyle. Also, each rectangle 4204, 4204 may be positioned such that the edges of the rectangles do not extend past the outer edge of each condyle. For example, the left rectangular shape 4202 is positioned such that the rectangle does not extend past the left-most edge of the left condyle. This ensures that the corresponding rectangular feature on the customized cutting guide does not extend past the condyle and interfere with the patient's anatomy during the arthroplasty procedure. The computing device may then utilize the placement information of the pair of rectangular shapes in the 2D image and translate that placement into the pair of rectangular shaped mating surfaces feature of the customized femoral cutting guide described below.

In a similar manner, a template for the customized tibia jig may also be created. Thus, the operator or computing device may perform one or more of the operations illustrated in FIG. 43 to determine the shape of the customized tibia cutting jig. Through the template design process, one or more mating surfaces or points of the tibia cutting jig may be determined by the computing device and/or the operator. These mating surfaces or points are then translated into the milling program for milling or cutting the specific, customized cutting jigs from jig blanks. In this manner, the information determined during the template design stage of the cutting jig design method results in the creation of one or more customized arthroplasty cutting guides or jigs based on the 2D images of a particular patient's joint. The operations may be performed by an operator of a computing device or the computing device itself through which the 2D images are available for viewing, alterable, and available for identifying landmarks within the images.

Similar to the operations described above, the operations of the method of FIG. 43 involve the operator or computing device analyzing the 2D images, selecting one or more of the 2D images and utilizing an input device to the computing device to define a shape in the images. In particular, the computing device provides a shape on the selected image that corresponds to a surface shape of a customized cutting jig. The operator (or computing device) then utilizes an input device to the computing device to locate the provided shape on the 2D image based at least on one or more landmarks or features of the patient's tibia as shown in the selected 2D image.

Beginning in operation 4302, the operator may verify that the bottom of the template of the customized cutting jig sits above the spine feature of the tibia. In particular, the computing device may provide an indicator, such as a reference box, in the 2D image that shows the location of the bottom of the template of the customized guide in relation to the 2D images. The operator may then tab through the set of coronal images that show the tibia to determine if the bottom edge of the reference box remains above the spine feature of the tibia. If an interference with the spine feature is detected on one or more of the image slices, the operator may move the reference box up in one or more of the 2D images to avoid interference with the spine.

In operation 4304, the operator or computing device may place a pair of circular shapes on the anterior surface of the tibia in one of the 2D images. These shapes correspond to the anterior surface circular contact surfaces of a customized femoral cutting guide. As such, the location of the pair of circular shapes on the anterior surface of the tibia in the 2D image may be translated to a milling program that creates a mating surface on a customized tibia cutting jig for use in an arthroplasty procedure that corresponds to the placement of the circular shapes. In this manner, the pair of circular shapes on the anterior surface of the tibia is customized to the patient's tibia as captured in the 2D images of the joint.

In one embodiment, the operator or computing device may select a 2D axial image of the tibia that is located slightly below the proposed resection line through the tibia. Within the axial image, the computing device provides a pair of circular shapes on the anterior surface of the tibia. Further, the pair of circular shapes on the anterior surface of the tibia within the 2D image may be adjustable by the operator. In particular, the operator utilizes the input device to the computing device to move the pair of circular shapes on the anterior right side surface of the tibia within the 2D image. One example of the position of the pair of circular shapes 4402, 4404 on the anterior surface of the tibia is shown in the screenshot 4400 of FIG. 44. In this manner, the pair of circular shapes 4402, 4404 on the anterior surface of the tibia create two contact points with the anterior surface. The computing device may then utilize the placement information of the pair of circular shapes 4402, 4404 on the anterior surface of the tibia in the 2D image and translate that placement into the anterior surface circular contact surfaces feature of the customized tibia cutting jig described herein.

In one embodiment, the pair of circular shapes 4402, 4404 on the anterior surface of the tibia may include a corresponding straight line reference 4406, 4408 that moves with the particular circular shape when the circular shape is moved by the operator. For example, when one of the circular shapes 4402, 4404 is moved to the right in the 2D image, the corresponding straight line reference 4406, 4408 also moves to the right. In this embodiment, the straight line references 4406, 4408 correspond to a potential drill hole of the tibia cutting jig. The location of the drill hole in relation to the circular shape is determined by the computing device through the general shape of the tibia cutting jig blank. In other words, the location of the drill hole in relation to the circular shape 4402, 4404 may be common among the cutting jig blanks and is known by the computing device. Thus, in this embodiment, the placement of the pair of circular shapes 4402, 4404 on the anterior surface of the tibia may be made in relation to the corresponding drill hole locations.

In operation 4306, the operator or computing device may place an anterior medial circular shape in one of the tibia 2D images. As explained in more detail below, this shape corresponds to the anterior medial circular mating surface of a customized tibia cutting guide. Thus, the location of the anterior medial circular shape in the 2D image may be translated to a milling program that creates a mating surface on a customized tibia cutting jig for use in an arthroplasty procedure that corresponds to the placement of the anterior medial circular shape. In this manner, the anterior medial circular shape is customized to the patient's tibia as captured in the 2D images of the joint.

Figure 45:
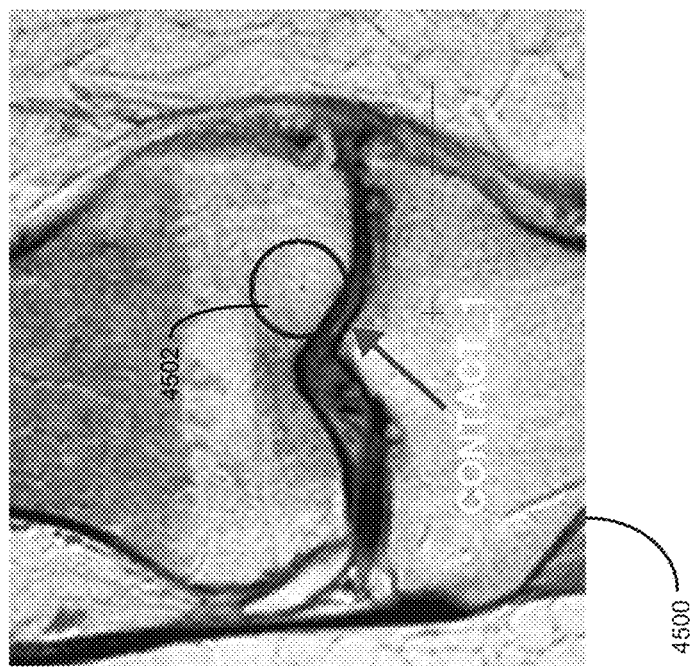
FIG. 45 is a screenshot of a coronal image of a patient's knee with a location of an anterior medial circular mating shape for the tibia identified in the image.

In one embodiment, the operator or computing device selects an axial image of the tibia from which a coronal image slice is selected. In one particular embodiment, the coronal image is selected from an area between the center and the lower edge of the lowest circular shape on the anterior surface of the tibia in the axial image discussed above. From this selection in the axial image, a coronal view corresponding to the selected axial image is provided to the operator. Within the coronal view, the computing device provides a circular shape. An example of the circular shape 4502 is provided in the coronal image is shown in screenshot 4500 of FIG. 45. Utilizing the input device to the computing device, the operator adjusts the circular shape 4502 to correspond to one or more landmarks in the selected 2D image. For example and as shown in FIG. 45, the circular shape 4502 may be positioned within the 2D image on the right side surface of the tibia plateau, near the spine feature. This positioning of the circular shape 4502 provides the corresponding customized tibia cutting guide with one contact point with the tibia plateau of the patient. As such, the computing device may then utilize the placement information of the anterior medial circular shape in the 2D image and translate that placement into the anterior medial circular mating surface feature of the customized tibia cutting jig described below.

In operation 4308, the operator or computing device may place an anterior lateral circular shape in one of the tibia 2D images. As explained in more detail below, this shape corresponds to the anterior lateral circular mating surface of a customized tibia cutting jig. Thus, the location of the anterior lateral circular shape in the 2D image may be translated to a milling program that creates a mating surface on a customized tibia cutting jig for use in an arthroplasty procedure that corresponds to the placement of the anterior lateral circular shape. In this manner, the anterior lateral circular shape is customized to the patient's tibia as captured in the 2D images of the joint.

Figure 46:
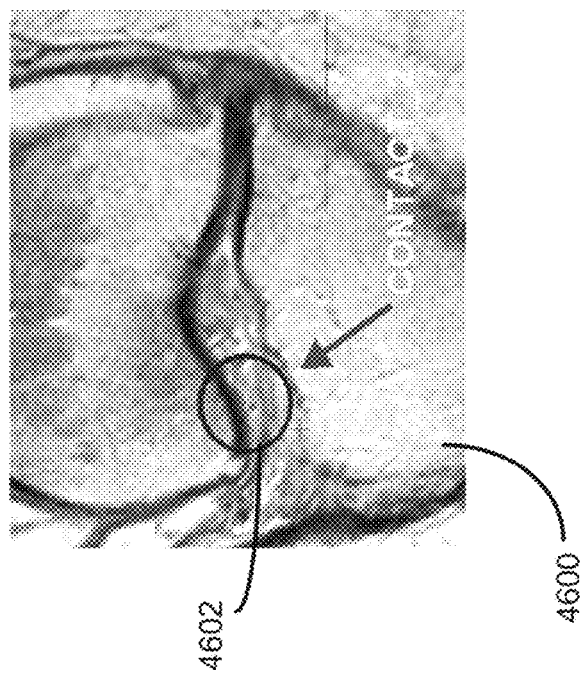
FIG. 46 is a screenshot of a coronal image of a patient's knee with a location of an anterior lateral circular mating shape for the tibia identified in the image.

In one embodiment, the operator or computing device selects a sagittal image of the tibia from which a coronal image slice is selected. In one particular embodiment, the coronal image is selected from an area above the anterior slope of the tibia in the sagittal image discussed above. From this selection in the sagittal image, a coronal view corresponding to the position in the sagittal image is provided to the operator. Within the coronal view, the computing device provides a circular shape. An example of the circular shape 4602 provided in the coronal image is shown in the screenshot 4600 of FIG. 46. Utilizing the input device to the computing device, the operator adjusts the circular shape 4602 to correspond to one or more landmarks in the selected 2D image. For example and as shown in FIG. 46, the circular shape 4602 may be positioned within the 2D image on the left side cortical bone surface of the tibia plateau. This positioning of the circular shape 4602 provides the corresponding customized tibia cutting jig with one contact point with the tibia plateau of the patient. As such, the computing device may then utilize the placement information of the anterior lateral circular shape in the 2D image and translate that placement into the anterior lateral circular mating surface feature of the customized tibia cutting jig described below.

In operation 4310, the operator or computing device may place a posterior medial circular shape in one of the tibia 2D images. As explained in more detail below, this shape corresponds to the posterior medial circular mating surface of a customized tibia cutting jig. Thus, the location of the posterior medial circular shape in the 2D image may be translated to a milling program that creates a mating surface on a customized tibia cutting jig for use in an arthroplasty procedure that corresponds to the placement of the posterior medial circular shape. In this manner, the posterior medial circular shape is customized to the patient's tibia as captured in the 2D images of the joint.

Figure 47:
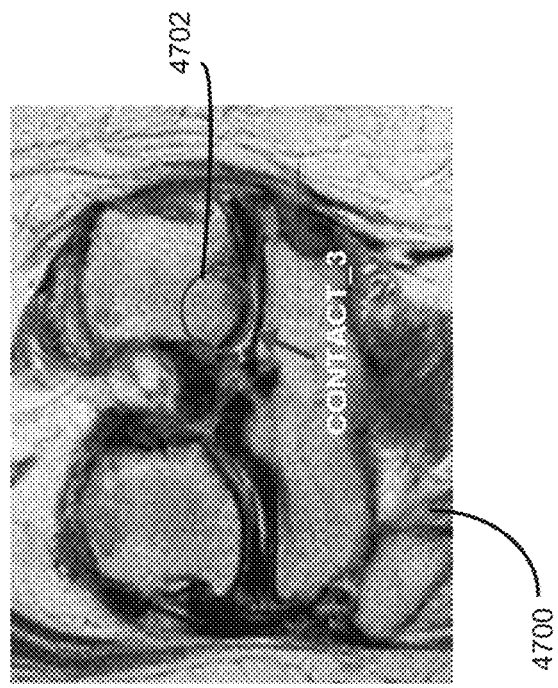
FIG. 47 is a screenshot of a coronal image of a patient's knee with a location of a posterior medial circular mating shape for the tibia identified in the image.

In one embodiment, the operator or computing device selects an axial image of the tibia from which a coronal image slice is selected. In one particular embodiment, the coronal image is selected from a posterior medial area spaced apart from the anterior medial circle position determined above. From this selection in the axial image, a coronal view corresponding to the position in the axial image is provided to the operator. Within the coronal view, the computing device provides a circular shape. An example of the circular shape 4702 provided in the coronal image is shown in the screenshot 4700 of FIG. 47. Utilizing the input device to the computing device, the operator adjusts the circular shape 4702 to correspond to one or more landmarks in the selected 2D image. For example and as shown in FIG. 47, the circular shape 4702 may be positioned within the 2D image on the tibia right side plateau surface. This positioning of the circular shape 4702 provides the corresponding customized tibia cutting jig with one contact point with the tibia plateau of the patient. As such, the computing device may then utilize the placement information of the posterior medial circular shape in the 2D image and translate that placement into the posterior medial circular mating surface feature of the customized tibia cutting guide described below.

Similarly, in operation 4312, the operator or computing device may place a posterior lateral circular shape in one of the tibia 2D images. As explained in more detail below, this shape corresponds to the posterior lateral circular mating surface of a customized tibia cutting jig. Thus, the location of the posterior lateral circular shape in the 2D image may be translated to a milling program that creates a mating surface on a customized tibia cutting jig for use in an arthroplasty procedure that corresponds to the placement of the posterior lateral circular shape. In this manner, the posterior lateral circular shape is customized to the patient's tibia as captured in the 2D images of the joint.

Figure 48:
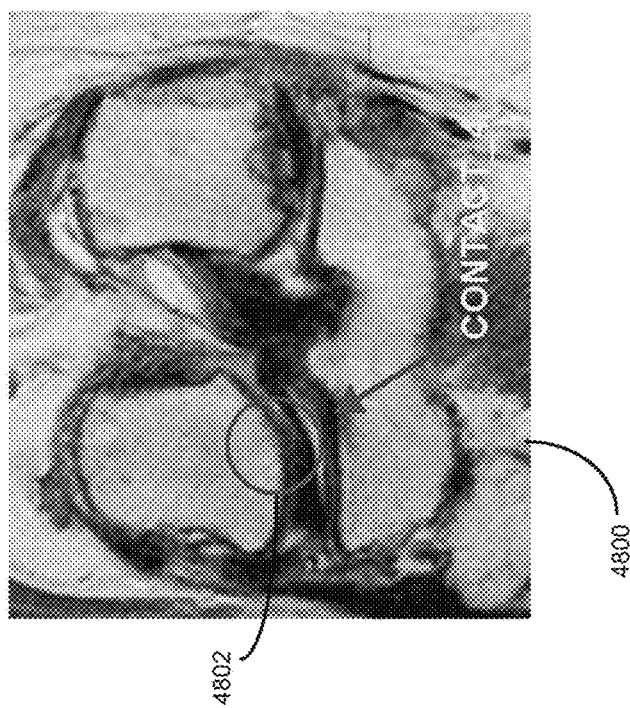
FIG. 48 is a screenshot of a coronal image of a patient's knee with a location of a posterior lateral circular mating shape for the tibia identified in the image.

In one embodiment, the operator or computing device selects an axial image of the tibia from which a coronal image slice is selected. In one embodiment, the axial image may be the same or similar image selected in operation 4310 discussed above. From this selection in the axial image, a coronal view corresponding to the position in the axial image is provided to the operator. Within the coronal view, the computing device provides a circular shape. An example of the circular shape 4802 provided in the coronal image is shown in FIG. 48. Utilizing the input device to the computing device, the operator adjusts the circular shape 4802 to correspond to one or more landmarks in the selected 2D image. For example and as shown in FIG. 48, the circular shape 4802 may be positioned within the 2D image on the tibia left side plateau surface near the spine feature. This positioning of the circular shape 4802 provides the corresponding customized tibia cutting jig with one contact point with the tibia plateau of the patient. As such, the computing device may then utilize the placement information of the posterior lateral circular shape in the 2D image and translate that placement into the posterior lateral circular mating surface feature of the customized tibia cutting guide described below.

In operation 4314, the operator or computing device may place a mid-lateral circular shape in one of the tibia 2D images. As explained in more detail below, this shape corresponds to the mid-lateral circular mating surface feature of a customized tibia cutting jig. Thus, the location of the mid-lateral circular shape in the 2D image may be translated to a milling program that creates a mating surface on a customized tibia cutting jig for use in an arthroplasty procedure that corresponds to the placement of the mid-lateral circular shape. In this manner, the mid-lateral circular shape is customized to the patient's tibia as captured in the 2D images of the joint.

Figure 49:
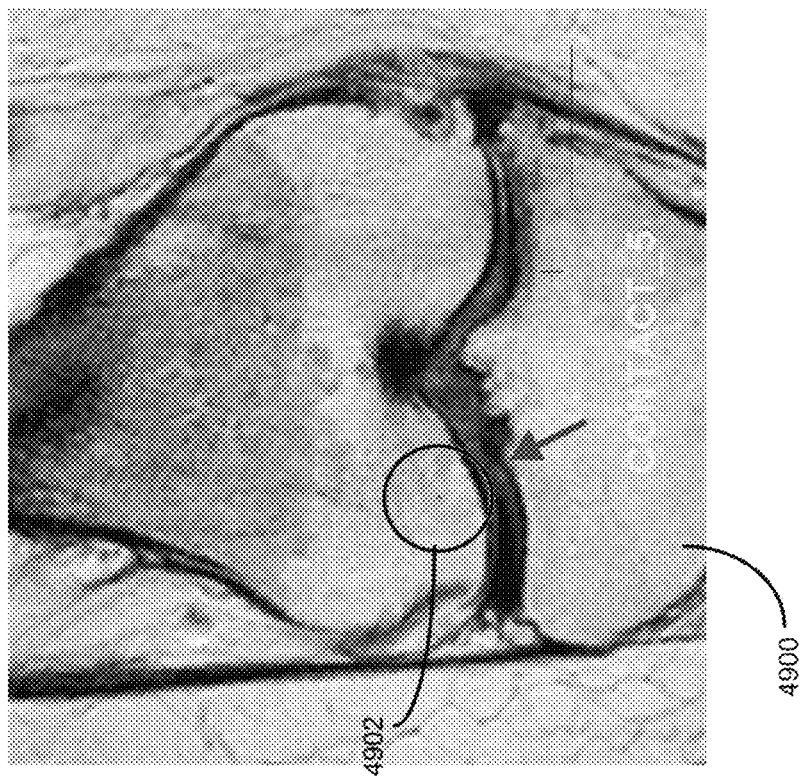
FIG. 49 is a screenshot of a coronal image of a patient's knee with a location of a mid-lateral circular mating shape for the tibia identified in the image.

In one embodiment, the operator or computing device selects an axial image of the tibia from which a coronal image slice is selected. In one particular embodiment, the coronal image is selected from a position slightly below the anterior lateral circle position determined above. From this selection in the axial image, a coronal view corresponding to the position in the axial image is provided to the operator. Within the coronal view, the computing device provides a circular shape. An example of the circular shape 4902 provided in the coronal image is shown the screenshot 4900 in FIG. 49. Utilizing the input device to the computing device, the operator adjusts the circular shape 4902 to correspond to one or more landmarks in the selected 2D image. For example and as shown in FIG. 49, the circular shape 4902 may be positioned within the 2D image on the tibia left side plateau surface. This positioning of the circular shape 4902 provides the corresponding customized tibia cutting jig with one contact point with the tibia plateau of the patient. As such, the computing device may then utilize the placement information of the mid-lateral circular shape in the 2D image and translate that placement into the mid-lateral circular mating surface feature of the customized tibia cutting jig described below.

Through the methods described above, a customized arthroplasty cutting guide or jig for a joint may be created specific to the anatomy of the patient. In particular, the methods provide for creating a customized arthroplasty cutting jig from one or more 2D images of the patient's joint. The method includes receiving the 2D images of the joint from an imaging device, reformatting the images, and creating a customized jig template from the images. In general, one or more landmarks are electronically marked on one or more of the series of 2D images of the patient's joint through a computing device. These electronic markers on the series of 2D images correspond to landmarks of the patient's joint undergoing the arthroplasty procedure. Once the template for the cutting jig is created by the computing device utilizing one or more of the electronic markers on the 2D images, a cutting or milling program is generated by the computing device. The cutting or milling program may then be provided to a milling machine to create the cutting jig corresponding to the milling program. The cutting jig is thus customized to the landmarks identified in the series of 2D images of the patient's joint.

Figure 50:
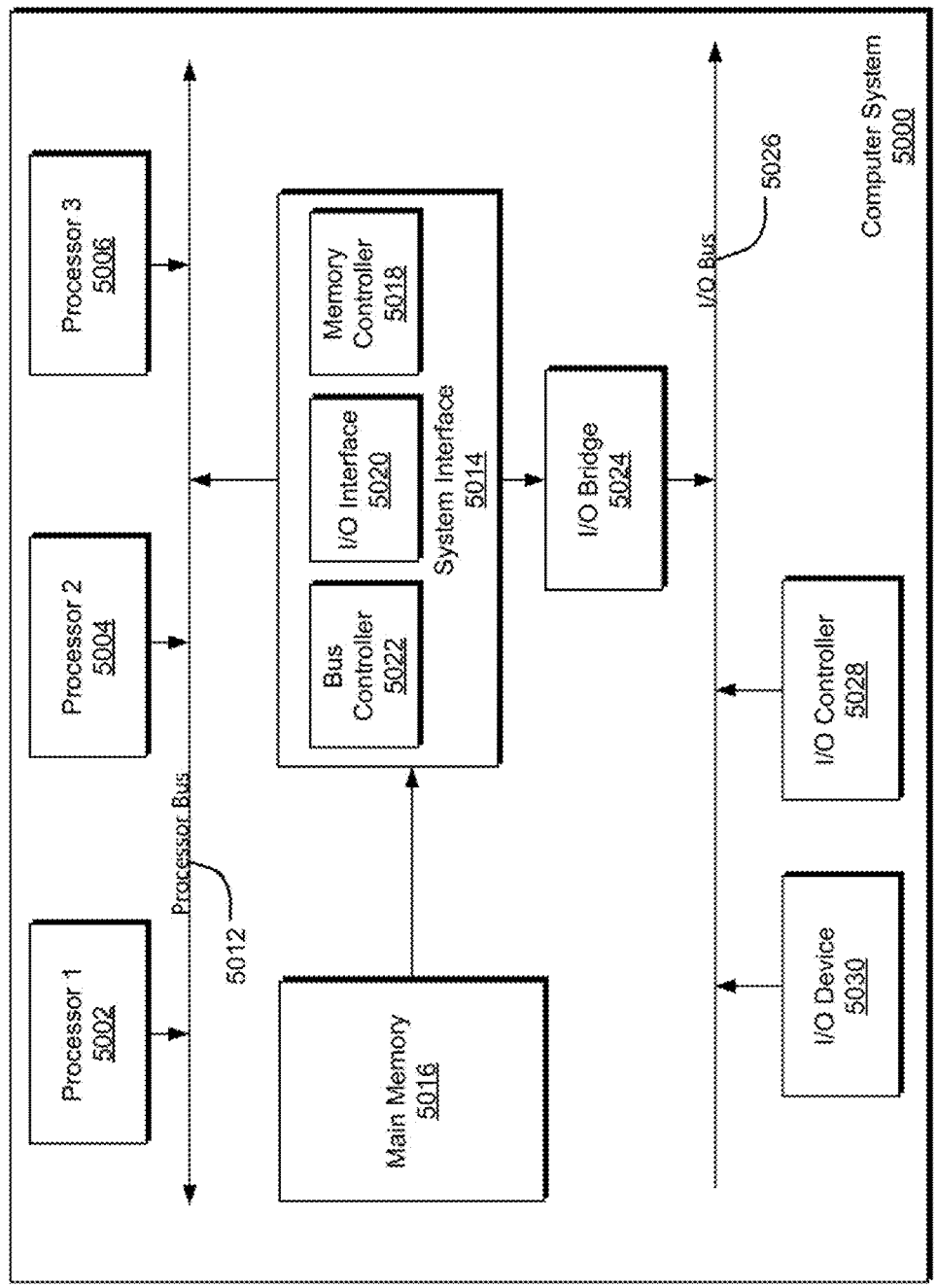
FIG. 50 is a block diagram illustrating an example of a computing system which may be used in implementing embodiments of the present disclosure.

FIG. 50 is a block diagram illustrating an example of a computing device or computer system 5000 which may be used in implementing the embodiments disclosed above. The computer system (system) includes one or more processors 5002-5006. Processors 5002-5006 may include one or more internal levels of cache (not shown) and a bus controller or bus interface unit to direct interaction with the processor bus 5012. Processor bus 5012, also known as the host bus or the front side bus, may be used to couple the processors 5002-5006 with the system interface 5014. System interface 5014 may be connected to the processor bus 5012 to interface other components of the system 5000 with the processor bus 5012. For example, system interface 5014 may include a memory controller 5018 for interfacing a main memory 5016 with the processor bus 5012. The main memory 5016 typically includes one or more memory cards and a control circuit (not shown). System interface 5014 may also include an input/output (I/O) interface 5020 to interface one or more I/O bridges or I/O devices with the processor bus 5012. One or more I/O controllers and/or I/O devices may be connected with the I/O bus 5026, such as I/O controller 5028 and I/O device 5030, as illustrated.

I/O device 5030 may also include an input device (not shown), such as an alphanumeric input device, including alphanumeric and other keys for communicating information and/or command selections to the processors 5002-5006. Another type of user input device includes cursor control, such as a mouse, a trackball, or cursor direction keys for communicating direction information and command selections to the processors 5002-5006 and for controlling cursor movement on the display device.

System 5000 may include a dynamic storage device, referred to as main memory 5016, or a random access memory (RAM) or other computer-readable devices coupled to the processor bus 5012 for storing information and instructions to be executed by the processors 5002-5006. Main memory 5016 also may be used for storing temporary variables or other intermediate information during execution of instructions by the processors 5002-5006. System 5000 may include a read only memory (ROM) and/or other static storage device coupled to the processor bus 5012 for storing static information and instructions for the processors 5002-5006. The system set forth in FIG. 50 is but one possible example of a computer system that may employ or be configured in accordance with aspects of the present disclosure.

According to one embodiment, the above techniques may be performed by computer system 5000 in response to processor 5004 executing one or more sequences of one or more instructions contained in main memory 5016. These instructions may be read into main memory 5016 from another machine-readable medium, such as a storage device. Execution of the sequences of instructions contained in main memory 5016 may cause processors 5002-5006 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media. Non-volatile media includes optical or magnetic disks. Volatile media includes dynamic memory, such as main memory 5016. Common forms of machine-readable medium may include, but is not limited to, magnetic storage medium; optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

A femoral cutting jig conforming with various aspects of the present disclosure includes a substrate from which various jig contact points project, are otherwise supported or defined. In one possible implementation, the jig is a unified structure formed from a block of base material using a computer numerical control (CNC) machine. However, it is possible for the jig to be an assembly of various components that form the final cutting jig structure. Alternatively, the jig may be created through molding, machining, milling, forming, 3D printing, assembling, or other processes. The jig contact points are arranged and spaced such that a surgeon may press the jig onto the distal surface of the femur and the jig will be properly positioned when the jig contact points are seated on respective femoral contact points. Notably, there are a discrete number of jig contact points (e.g., 9-14) as opposed to full surfaces or far more numerous numbers of contact locations. The jig also includes a cutting guide support structure onto which may be mounted a cutting guide (CG). When the jig is seated on the femur, the jig may be pinned to the femur to properly position the cutting guide so that a resection of the femur may be performed pursuant to a total knee replacement.

Referring now to FIGS. 102A and 102B, and 103A-103E, the jig includes a first substrate portion 48 and a second substrate portion 50 generally perpendicular the first substrate portion. The relative position and orientation between the first substrate portion and the second substrate portion need not be perpendicular, however. As can be seen in FIG. 103B, the first substrate portion 48 is generally transverse to a femoral axis 52 of the femur 6 (substantially in the axial plane when mounted) and the second substrate portion 50 is generally perpendicular to the first substrate portion (substantially in the coronal plane when mounted). It should be noted that the jig positions the cut plane bar, and hence the jig position on the femur will vary based on the anatomy of the patient, the type of procedure, the type of prosthetic, and any number of other factors. Hence, the anatomical relationships described are illustrative and not limiting.

Beginning at the trochlear groove end of the jig 20, a vertical projection 11 (FIG. 102A) is located at the center of an anterior end of the second substrate portion 50. The vertical projection provides a visual queue or reference for a surgeon. When the jig is properly positioned on the femur, the central vertical projection aligns visually with the anterior proximal end region of the trochlear groove 14. In the specific jig shown, the vertical projection is positioned on and between a first and a second horizontal surface, 12-1 and 12-2, which are in turn positioned between first and second curved, descending concave surfaces 13-1 and 13-2, which may be formed by tooling elements, such as from CNC machine router bits. The descending surfaces are formed from the removal of material, and the material may be removed to allow a surgeon to see past the vertical projection to where the points along the curvilinear surface 16 contact the respective condyles 10, 12 to either side of the trochlear groove as discussed in further detail below. The features 11, 12-1, 12-2, 13-1, and 13-2 are bounded on a first side by first and second vertical surfaces, 14-1 and 14-2, of the second substrate portion. The various features discussed and shown herein are but one way to create a jig defining the various jig contact points of interest. In the example shown, the CNC machine tool bits and other cutting mechanisms influence the jig shapes. The various surfaces and jig features, on which the jig contact points are defined, are thus defined in part by requirements of the CNC machine. If the jig were formed in another way, such as through 3D printing or molding, the jig contact point features and overall jig shape may be different than illustrated although the position and relative location of the jig contact points, depending on the patient, would be substantially the same regardless of the jig manufacturing technique employed.

The implementation of the jig illustrated herein includes two curvilinear (e.g., partial circle or section) trochlear groove surfaces, with each surface defining two jig contact points (JCP1, JCP2 and JCP5, JCP6) configured to engage respective first and second femoral contact points (CP1 and CP2) and respective fifth and sixth contact points (CP5 and CP6) to either side of the trochlear groove 14 adjacent the respective condyles. More specifically, a first curved surface 15 defining the first jig contact point (JCP1) and the second jig contact point (JCP2). The first and second jig contact points contact respective first and second femoral contact points (CP1 and CP2). In the specific implementation illustrated, the surface 15 defines a curvilinear lip 16, which is bounded between the first and second vertical surfaces 14-1, 14-2, a third and a fourth horizontal surface, 17-1 and 17-2, and vertical surface 18. A third jig contact point JCP3 and a fourth jig contact point JCP4 are defined along a boundary between the respective horizontal surfaces 17-1/17-2 and a third vertical surface 18. The jig contact points JCP3 and JCP4 may be in the same plane as JCP1 and JCP4 (substantially parallel to the femoral axis), and contact respective femoral contact points CP3 and CP4, on the respective lateral and medial condyles adjacent the trochlear groove with points CP1 and CP2 above points CP3 and CP4, respectively on the lateral and medial condyles. Stated differently, the contact points CP3 and CP4 may be on the portions of the condyles facing each other at the trochlear groove 14, and may be on the walls of the groove itself, and the respective points CP3 and CP4 medially and laterally, respectively, CP1 and CP2.

As discussed throughout, the jig structure illustrated is a convenience of manufacturing, with the jig originally formed from a block of material and machined away to form the resulting structures. It is possible to also define a curvilinear surface 16 as a discrete planar element extending from the first substrate portion, and defining the curvilinear (arcuate) surface with contact points JCP1 and JCP2. Jig contact points JCP3 and JCP4 may be defined using a planar rectangular element, a radial planar element, or other structures. In the implementation shown, the surface 15 is machined to a smaller size relative to the 16 so that the jig contact points defined along surface 16 may contact the appropriate femur surface without unintentional contact by surface 15. Since the groove 14 descends away from the jig when positioned, the arced surface shape 15 is believed to not interfere with the groove while at the same time not requiring extensive machine time. The surface 16 may be machined to a greater extent than illustrated but such machining would require greater time and is not believed to be required for most patients. Finally, should there be contact between surface 15 and the knee, the shape is believed to allow the surgeon to press the jig into place and ensure proper contact between the jig contact points and the femur contact points.

The third vertical surface 18 bounds the first curved surface 15 and bounds the third and fourth horizontal surfaces, 17-1 and 17-2. The third vertical surface 18 is bounded on one side by a second curved surface 19 defining fifth and sixth jig contact points JCP5 and JCP6, which contact respective femoral contact points CP5 and CP6. In the specific implementation shown, the contact points are defined along a second curved surface lip 54, bounded on one side by a fourth vertical surface 21. The contact points CP5 and CP6 are on the respective lateral and medial condyles 10, 12, and posterior relative to the contact points CP1 and CP6. Stated differently, the contact points CP5 and CP6 are on the respective lateral and medial condyles or the portion of the groove 14 adjacent thereto, at the posterior region of the trochlear groove 14 adjacent the intercondylar fossa 16. As with other surfaces, projections and the likely structure illustrated is a convenience of manufacturing, with the jig originally formed from a block of material and machined away to form the resulting jig contact points JCP5 and JCP6. It is possible to also define a curvilinear surface 54 as a discrete planar element extending from the first substrate portion 48, and defining the curvilinear (arcuate) surface with contact points JCP5 and JCP6. The first curvilinear surface 16 is concentric with the second curvilinear surface 20.

As illustrated, there are six jig contact points defined to contact the respective lateral and medial condyles to either side of the trochlear groove. In the embodiment shown, there are four contact points defined along two curvilinear arcuate surfaces 16 and 54. The arcuate surfaces are defined to fit down within the space above groove with portion of the arcs touching the groove or respective condyles. The respective condyles are generally rounded and come to a peak region where the contact points CP3 and CP4 are defined and where the planar/linear surfaces 17-1, 17-2 may define the jig contact points JP3 and JP4. In this way, the jig may be placed down on the femur and the jig contact points may touch and seat against the respective femoral contact points.

A first and a second horizontal plateau projection, 22-1 and 22-2, each with an aperture, 30A and 30B defined therein, extend transversely adjacent to the fourth vertical surface 21 and are part of the first substrate, in one possible implementation. As shown in FIG. 102B, the apertures extend through the respective bosses 42A and 42B extending from the first substrate, and on a side of the jig away from where the jig contacts the femur. A diagonally oriented surface 31 extends from the first substrate 48 to a fifth vertical surface 32. The diagonal surface 31 has the boss 42C and an aperture 30C therein. The fifth vertical surface is contiguous to a rectangle bar 35 for cut bar orientation, which lies between the fifth vertical surface and a sixth vertical surface 36, and to which the cut plane bar 40 is mounted.

With respect now to contact points adjacent the intercondylar fossa 16, six additional jig contact points may be defined that cooperate with the first six contact points discussed above, to secure the jig to the femur for a procedure. More particularly, first and second curvilinear quadrilaterals, 23 and 24, extend from the first substrate and are contiguous to each other. The quadrilaterals may be generally parallel the second substrate portion 50. The vertical surfaces are part of the second substrate portion. Additionally, adjacent and outward from the quadrilaterals, two curvilinear surfaces 25 and 26 project from the first substrate. Collectively, the quadrilaterals and curvilinear surfaces define jig contact points JCP7-JCP12 that contact respective femoral contact points CP7-CP12 lying on the lateral and medial condyles adjacent the intercondylar fossa 16. More specifically, as shown in FIGS. 101A and 101B, the contact points CP7, CP9 and CP11 lie on an inner surface of the medial condyle (facing the fossa and lateral condyle) successively posterior relative to the groove 14 and adjacent the intercondylar fossa 16. Contact points CP8, CP10, and CP12 lie on an inner surface of the lateral condyle (facing the fossa and medial condyle) also successively posterior relative to the groove 14 and adjacent the intercondylar fossa 16. CP7 may be coplanar to CP8, CP9 may be coplanar to CP10, and CP11 may be coplanar to CP12, in planes substantially parallel the femoral axis 52. The planes are substantially parallel but will deviate from parallel depending on numerous factors including the femur axis relative to the knee and cut plane, the type of procedure, the degree of degeneration the knee and the jig form to deal with the same, and other anatomical and/or requirements of the procedure.

Figure 104A:
FIGS. 104A-104I illustrate two dimensional, closed and open, linear and curvilinear formats that can be used to construct tangent lines and other linear and curvilinear approximation elements used in obtaining relevant dimensions in different embodiments, illustrated in an example in FIG. 104J.

FIGS. 104A through 104I illustrate some two dimensional, linear and curvilinear formats that can be used in embodiments to construct tangent lines, other approximation elements (FIG. 104J), and geometrical structures that provide one more jig contact points along a surface thereof. Stated differently, various geometric shapes may be used to define a jig contact point and FIG. 4 provides various examples of such shapes. Referring first to FIG. 104J, a portion of an MRI slice is illustrated. The MRI slice shows a line 56 denoting a boundary of the femur where a femur contact point 58 is located and where a corresponding jig contact point 60 is defined, which will contact the fibia at the femur contact point. The femur portion illustrated may be cortical bone, cancellous bone or cartilage at a boundary to open space or otherwise. Because each such material may have its own range of grey scales in the MRI image, the line is merely representative of a contact area, which may not be in fact a discrete line. The femur contact area of the MRI may be a slice through all or a portion of either or both condyles, the trochlear groove, the femur shaft, or other regions of the distal area of the femur relevant to a total knee replacement procedure or other femoral procedure that may take advantage of the jig described herein.

In the view illustrated in FIG. 104J, a portion of a coronal plane MRI slice of the distal femur is illustrated. More specifically, the line represents a coronal plane MRI slice of the lateral condyle encompassing a femoral contact point 58 (e.g., CP1). In order to define a jig contact point 60 (e.g., JCP1), various lines and geometrical shapes may be deployed. In the case of FIG. 104A, a rectangle is used to define the jig contact point at the corresponding femoral contact point. The line defined by the MRI slice encompassing the femoral contact point is characterized by a curve, $y=f(x)$, which is assumed to be continuously differentiable in an interval $a \le x \le b$, and to have a well-defined tangent line slope, $dy/dx=df/dx$, at a point, $(x, y)=(x0, y0)$. For example, three spaced apart, noncollinear coordinate pairs, $(xm, ym)$ $(m=1, 2, 3)$ can be used to determine an optimal rectangle (length and width) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a rectangular contact point defining structure or other structures, the structure may be made to intersect or touch the femoral contact area of interest at and with coinciding tangent lines.

Figure 104B:

In the case of FIG. 104B, a line segment is used to define the jig contact point at the corresponding femoral contact point. The line defined by the MRI slice encompassing the femoral contact point is characterized by a curve, $y=f(x)$, which is assumed to be continuously differentiable in an interval $a \le x \le b$, and to have a well-defined tangent line slope, $dy/dx=df/dx$, at a point, $(x, y)=(x0, y0)$. For example, three spaced apart, noncollinear coordinate pairs, $(xm, ym)$ $(m=1, 2, 3)$ can be used to determine an optimal line (length) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a linear contact point defining structure or other structures, the structure may be made to intersect or touch the femoral contact area of interest at and with coinciding tangent lines.

Figure 104C:

In the case of FIG. 104C, a circle is used to define the jig contact point at the corresponding femoral contact point. The line defined by the MRI slice encompassing the femoral contact point is characterized by a curve, $y=f(x)$, which is assumed to be continuously differentiable in an interval $a \le x \le D$, and to have a well-defined tangent line slope, $dy/dx=df/dx$, at a point, $(x, y)=(x0, y0)$. For example, three spaced apart, noncollinear coordinate pairs, $(xm, ym)$ $(m=1, 2, 3)$ can be used to determine an optimal circle (center and radius) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a circular contact point defining structure or other structures, the structure may be made to intersect or touch the femoral contact area of interest at and with coinciding tangent lines.

Figure 104D:

In the case of FIG. 104D, an ellipse is used to define the jig contact point at the corresponding femoral contact point. The line defined by the MRI slice encompassing the femoral contact point is characterized by a curve, $y=f(x)$, which is assumed to be continuously differentiable in an interval $a \le x \le D$, and to have a well-defined tangent line slope, $dy/dx=df/dx$, at a point, $(x, y)=(x0, y0)$. For example, three spaced apart, noncollinear coordinate pairs, $(xm, ym)$ $(m=1, 2, 3)$ can be used to determine an optimal ellipse (center and radius) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of an elliptical contact point defining structure or other structures, the structure may be made to intersect or touch the femoral contact area of interest at and with coinciding tangent lines.

Figure 104E:

In the case of FIG. 104E, a triangle is used to define the jig contact point at the corresponding femoral contact point. The line defined by the MRI slice encompassing the femoral contact point is characterized by a curve, $y=f(x)$, which is assumed to be continuously differentiable in an interval $a \le x \le D$, and to have a well-defined tangent line slope, $dy/dx=df/dx$, at a point, $(x, y)=(x0, y0)$. For example, three spaced apart, noncollinear coordinate pairs, $(xm, ym)$ $(m=1, 2, 3)$ can be used to determine an optimal triangle (base and height) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a triangular contact point defining structure or other structures, the structure may be made to intersect or touch the femoral contact area of interest at and with coinciding tangent lines.

Figure 104F:

In the case of FIG. 104F, a trapezoid is used to define the jig contact point at the corresponding femoral contact point. The line defined by the MRI slice encompassing the femoral contact point is characterized by a curve, $y=f(x)$, which is assumed to be continuously differentiable in an interval $a \le x \le D$, and to have a well-defined tangent line slope, $dy/dx=df/dx$, at a point, $(x, y)=(x0, y0)$. For example, three spaced apart, noncollinear coordinate pairs, $(xm, ym)$ $(m=1, 2, 3)$ can be used to determine an optimal trapezoid (base and height) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a trapezoidal contact point defining structure or other structures, the structure may be made to intersect or touch the femoral contact area of interest at and with coinciding tangent lines.

Figure 104G:

In the case of FIG. 104G, a parallelogram is used to define the jig contact point at the corresponding femoral contact point. The line defined by the MRI slice encompassing the femoral contact point is characterized by a curve, $y=f(x)$, which is assumed to be continuously differentiable in an interval $a \le x \le D$, and to have a well-defined tangent line slope, $dy/dx=df/dx$, at a point, $(x, y)=(x0, y0)$. For example, three spaced apart, noncollinear coordinate pairs, $(xm, ym)$ $(m=1, 2, 3)$ can be used to determine an optimal parallelogram (base and height) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a parallelogram contact point defining structure or other structures, the structure may be made to intersect or touch the femoral contact area of interest at and with coinciding tangent lines.

Figure 104H:

In the case of FIG. 104H, a quadratic curve is used to define the jig contact point at the corresponding femoral contact point. The line defined by the MRI slice encompassing the femoral contact point is characterized by a curve, $y=f(x)$, which is assumed to be continuously differentiable in an interval a≤x≤D, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal quadratic curve (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a quadratic curve contact point defining structure or other structures, the structure may be made to intersect or touch the femoral contact area of interest at and with coinciding tangent lines.

Figure 104I:
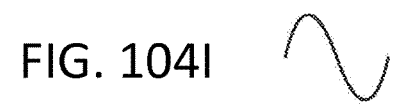
Figure 104J:
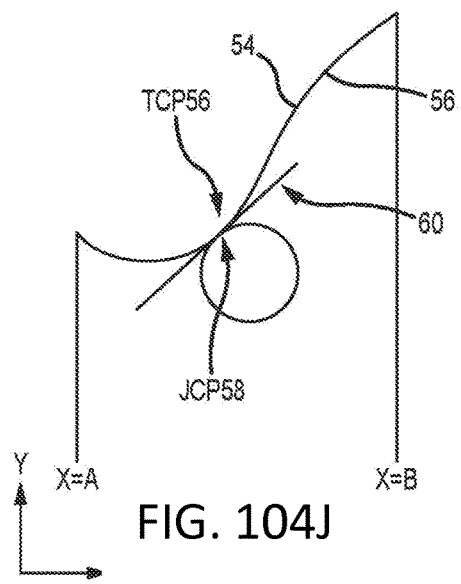

In the case of FIG. 104I, a cubic curve is used to define the jig contact point at the corresponding femoral contact point. The line defined by the MRI slice encompassing the femoral contact point is characterized by a curve, y=f(x), which is assumed to be continuously differentiable in an interval a≤x≤D, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal cubic curve (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a cubic curve contact point defining structure or other structures, the structure may be made to intersect or touch the femoral contact area of interest at and with coinciding tangent lines.

FIG. 104J, illustrates the use of a circle to define the jig contact point at the corresponding femoral contact point. Depending on the implementation, it may be preferable that no corner point, such as a jig contact point, be sharp or otherwise have a high degree of sharpness such as is often associated with a true "point"; rather, a contact point may have an associated point radius that is at least about 0.3 mm in actual size or larger up to and including a line, in one possible implementation. The incorporation of this constraint will help ensure that, for example, a jig contact point will have adequate frictional contact such that the contact point will not slip or otherwise move relative to a region on the femur but at the same time the contact point will not penetrate or pierce any soft tissue on the portion of the femur being contacted which would possibly distort the fit of the jig to the femur. It is less of a concern about damaging the femur as the portion of the femur being contacted is likely to be removed (resected) and replaced with a prosthetic implant. Notably, if a linear segment surface, such as a segment of a square, rectangle, triangle or trapezoid, is used as the contact point defining structure, and a corner of such structure is not the contact point, the area along the linear segment surface at which contact is made, is considered to be a contact point. Moreover, in such an implementation, the linear segment surface may have a rounded or otherwise non-knife edge cross section, particularly at the area where the surface is intended to contact the femur.

Figure 105A:
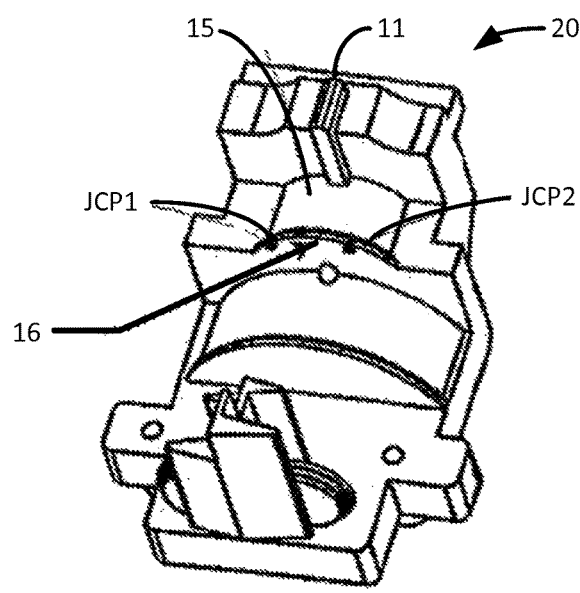
FIGS. 105A-105B are isometric and schematic views indicating suitable locations of FCJM contact points, according to an embodiment.
Figure 105B:
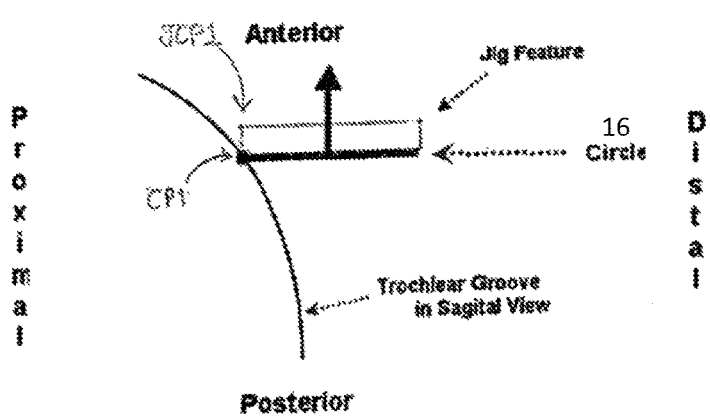

FIGS. 105-105O will now be discussed with additional reference to the various jig contact points. FIG. 105A is an isometric view of an embodiment of the jig 20, showing suitable positions for jig contact points, JCP1 and JCP2. FIG. 105B is a representative sagittal plane view of the lateral condyle area containing CP1 and illustrating the jig feature 16 (e.g., a portion of a circle) defining the jig contact point (JCP1) contacting the lateral condyle/trochlear groove at CP1. Referring to FIGS. 105A, 101A and 101B, with the femur size illustrated, the contact points CP1 and CP2 are spaced apart approximately 1.5 cm and lie on the semi-circle 16 with a radius determined by a radius r(15) (millimeters). Accordingly, the first curved surface 16 (FIG. 2A) defines the radius r(15), which will cause JCP1 and JCP2 to contact the femur at CP1 and CP2 with about 1.5 cm of spacing therebetween. Of course, with a larger or smaller sized femur or differently spaced and/or shaped condyles and trochlear groove, the contact points may be more or less separated, and typically with spacing between 11 mm and 19 mm, although variations outside of this range are possible. As indicated in a sagittal view of a portion of the trochlear groove, with the jig in contact with the respective condyles of the lower femur (FIG. 105B), each of the contact points, JCP1 and JCP2, can move anteriorly (indicated by the vertical upward arrow), but cannot move posteriorly (downward), because of the presence of a solid object—a portion of the trochlear groove and the respective condyles where jig contact points (JCP1 and JCP2) contact the respective femoral contact points (CP1 and CP2) when the jig is pressed on the femur.

Figure 106A:
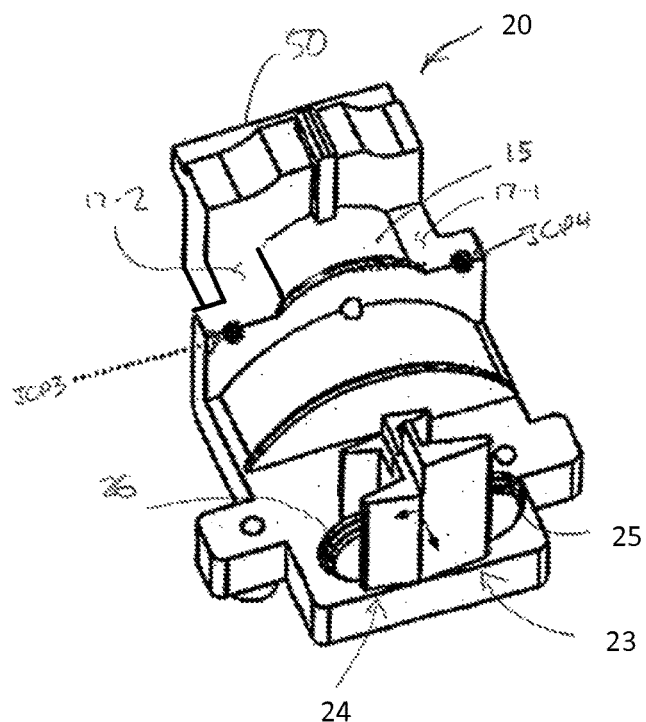
FIGS. 106A-106B are isometric and schematic views indicating suitable locations of FCJM contact points, according to an embodiment.
Figure 106B:
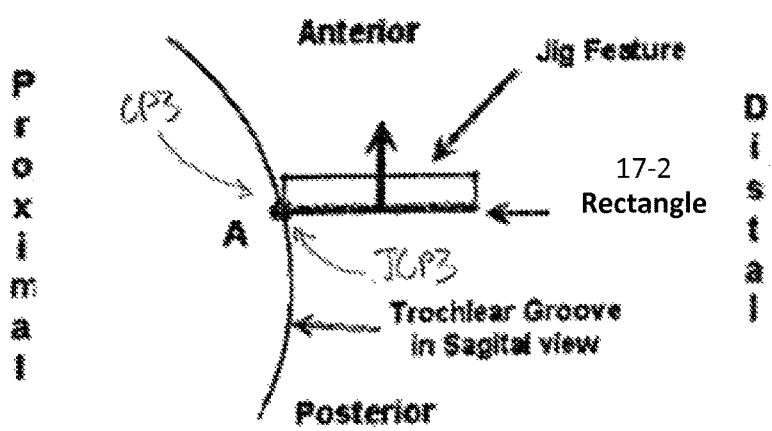

FIG. 106A is an isometric view of the jig 20, showing one or two suitable positions for jig contact points, JCP3 and JCP4. FIG. 106B is a representative sagittal plane view of the lateral condyle containing CP3 and illustrating a jig feature (a portion of rectangle) defining the jig contact point JCP3 contacting the lateral condyle at CP3. The femoral contact points CP3 and CP4 are spaced apart approximately 2 cm, but will typically fall within a range of 15 mm to 25 mm, depending on patient anatomy with variations outside this range possible. In the implementation illustrated, CP3 and CP4 are in the same sagittal plane as CP1 and CP2. Similarly, JCP3 and JCP4 are in the same sagittal plane as JCP1 and JCP2. However, such a coplanar arrangement is not necessary. In the specific implementation illustrated in FIG. 106A, JCP3 and JCP4 lie on the third and fourth horizontal surfaces, 17-1 and 17-2 (shown in FIG. 2A), and particularly along edge regions co planar with the lip 16 defining JCP1 and JCP2. While illustrated as surfaces, the contact points may also be defined on a rectangular planar projection extending from the substrate. Alternatively, the contact points may be defined on other surfaces or projections. For example, it would be possible to form the contact points on a circular surface, similar to the surface supporting contact points JCP1 and JCP2. However, with a CNC machine formed jig, the surface is an efficient and effective way to define the third and fourth jig contact points. Similar to the relation between JCP1 and JCP2, and as indicated in a sagittal view of a portion of the trochlear groove TG with the jig in contact with the lower femur (FIG. 106B), each of the jig contact points, JCP3 and JCP4, can move anteriorly (indicated by the vertical upward arrow), but cannot move posteriorly (downward), because of the presence of a solid object—a portion of the trochlear groove and the respective condyles where jig contact points (JCP3 and JCP4) contact the respective femoral contact points (CP3 and CP4) when the jig is pressed on the femur.

Figure 107A:
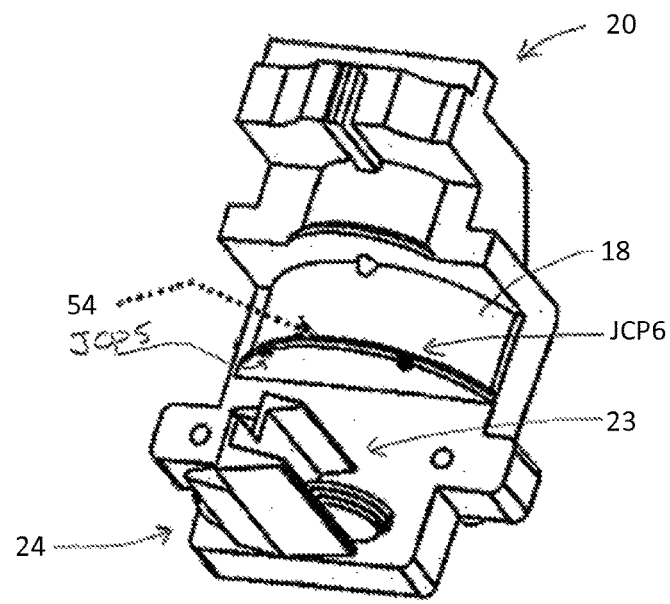
FIGS. 107A-107B are isometric and schematic views indicating suitable locations of FCJM contact points, according to an embodiment.
Figure 107B:
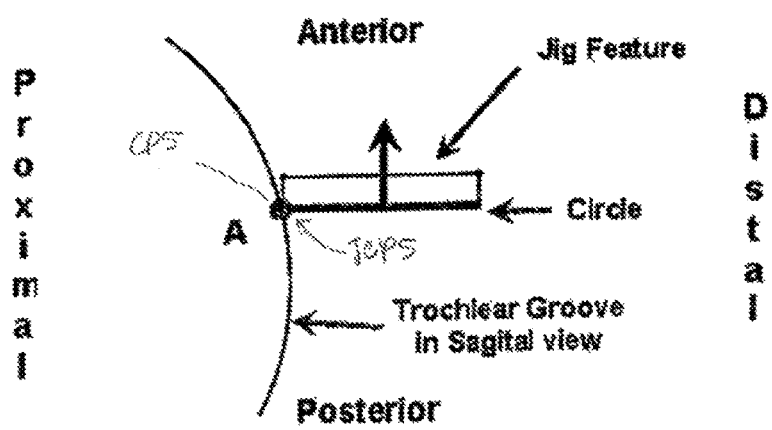

FIGS. 107A and 107B are isometric and schematic views of an embodiment of the jig, showing one or two suitable positions for jig contact points, JCP5 and JCP6, which contact the femur at respective contact points CP5 and CP6. The contact points CP5 and CP6 are spaced apart approximately 2.5 cm, but may typically fall within a range of 21 mm to 29 mm, although deviations outside this range are possible. Contact points CP5 and CP6 are positioned posteriorly relative to contact points CP1-CP4. The jig contact points lie on the semi-circular surface 54, which may have a radius determined by a radius r(18) (millimeters). Since the separation between CP5 and CP6, across the trochlear groove, is larger than the separation between CP1 and CP2 across the trochlear groove, the radius of the curvilinear (e.g. partial circular) surface 54 is larger than the radius of the curved surface 16. It is also possible to define a different structure to provide contact points CP5 and CP6. For example, a trapezoid defining a face at both JCP5 and JCP6 could be used, with the faces being defined along a tangent to the femur surface at CP5 and CP6. In another example, a discrete triangle defining respective surfaces at JCP5 and JCP6 might be deployed, again with a face of the triangle defined along a tangent to the femur surface at CP5 and CP6. As indicated in a sagittal view of a portion of the trochlear groove TG (FIG. 107B), with the jig in contact with the femur lower portion, each of the contact points, CP5 and CP6, can move anteriorly (indicated by vertical upward arrow), but cannot move posteriorly (downward), because of the presence of a solid object.

Figure 108:
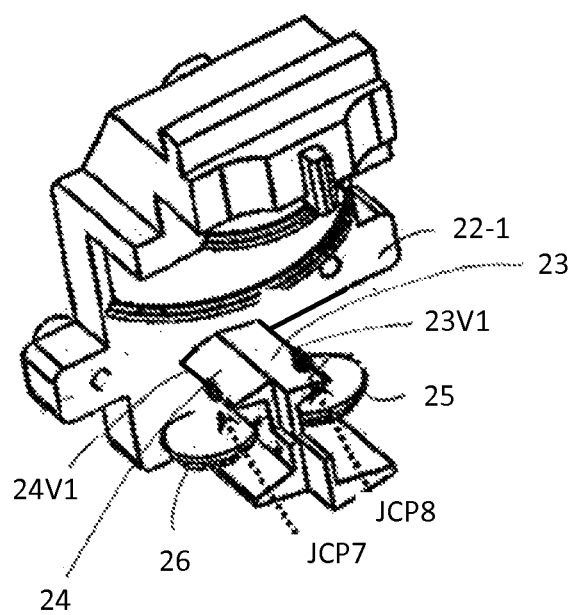
FIG. 108 is an isometric view indicating suitable locations of FCJM contact points (7-8), according to an embodiment.

FIGS. 108-1010B illustrate jig contact points defined on the extending quadrilaterals of the vertical projection 11, and partial circular projections 25, 26, from the first substrate portion 48 at a region distal the second substrate portion 50. FIG. 108 is an isometric view of the jig 20, showing one or two suitable positions for jig contact points, JCP7 and JCP8, that contact the femur at contact points CP7 and CP8 on the respective inner portions of the lateral and medial condyles adjacent to the intercondylar fossa 16. The jig contact points JCP7 and JCP8 lie on first vertices, 23V1 and 24V1, of the first and second curvilinear quadrilaterals, 23 and 24. The jig contact points are spaced apart approximately 2 cm, but may typically be in a range of 16 mm to 24 mm depending on patient anatomy. In the example illustrated, the quadrilaterals have a substantially triangular cross section, with intersection side walls coming together to define the respective vertices 23V1 and 24V1. The vertices are rounded and otherwise do not define a knife edge, in the implementation illustrated. The contact points lie in substantially the same sagittal plane but are offset slightly in the axial plane, with the contact points being on the inner portions of the respective condyles proximate to the intercondylar fossa. In contrast to jig contact points JCP1-JCP6, jig contact points JCP7 and JCP8 can move posteriorly but are restricted from moving anteriorly by the shape of the condyles and fossa. Here, the contact points are constrained by the respective inner (adjacent) portions of the lateral and medial condyles, as those features become closer together anteriorly.

Figure 109:
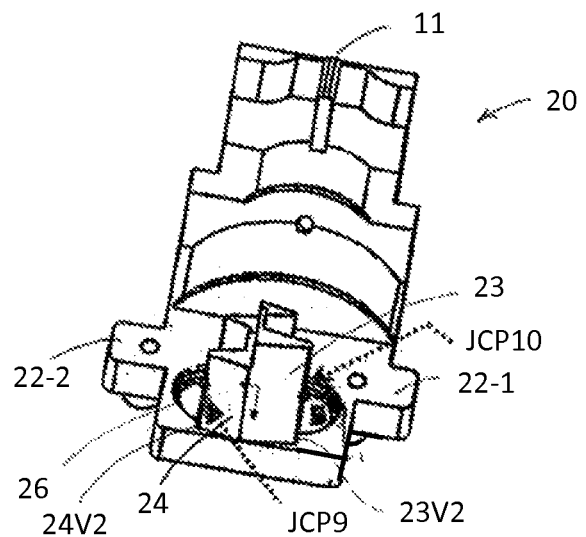
FIG. 109 is an isometric view indicating suitable locations of FCJM contact points (9-10), according to an embodiment.

FIG. 109 is an isometric view of the jig 20, showing one or two suitable positions for jig contact points, JCP9 and JCP10, that contact the femur at contact points CP9 and CP10 on the respective inner portions of the lateral and medial condyles posteriorly from contact points CP7 and CP8, and near the posterior end regions of the respective condyles. The contact points CP9 and CP10 lie on second vertices, 23V2 and 24V2, of the first and second curvilinear quadrilaterals, 23 and 24, and are spaced approximately 3 cm apart, but may typically be in a range of 26 mm to 34 mm depending on patient anatomy, although variations outside that range are possible. In the example illustrated, the quadrilaterals have a substantially triangular cross section, with intersection side walls coming together to define the respective vertices 23V2 and 24V2. The vertices are rounded and otherwise do not define a knife edge, in the implementation illustrated. The contact points lie in substantially the same sagittal plane but are offset slightly in the axial plane, with the contact points being on the inner portions of the respective condyles proximate the intercondylar fossa. Relative to JCP7 and JCP8, the separation between the condyles at JCP9 and JCP10 is greater. Contact points JCP9 and JCP10 can move posteriorly but are constrained from moving anteriorly when the jig is seated. Depending on the shape of the condyles where contact is made at JCP7-JCP10, it is possible that some of the jig contact points may not be constrained posteriorly or anteriorly, or not all of the points make contact.

FIGS. 1010A and 1010B are isometric and schematic views of the jig 20, showing one or two suitable positions for jig contact points, JCP11 and JCP12. The jig contact points JCP11 and JCP12 lie on the first and second circle sectors, 25 and 26 (FIG. 102A). As indicated in a sagittal view of a portion of the trochlear groove 14, with the jig in contact with the femur lower portion (FIG. 10B), each of the jig contact points, JCP11 and JCP12, can move posteriorly (indicated by vertical arrow), but cannot move anteriorly, because of the presence of a solid object, a portion of one or the other condyle, LC and/or MC. JCP11 and JCP12 are in the same or substantially the same sagittal plane as JCP9 and JCP10 in the embodiment illustrated.

The contact points CP1, CP2, CP3, CP4, CP5 and/or CP6 are associated with features of the trochlear groove and condyle features adjacent thereto, and the contact points CP7, CP8, CP9, CP10, CP11 and/or CP12 are associated with features of one or both of the condyles adjacent to and posterior from the intercondylar fossa. One goal of the contact points on the jig 20 is to provide an optimal position of the jig in contact with the distal femur for which lateral rotation (posterior to anterior, or anterior to posterior) of the jig relative to the lower femur, or longitudinal (sagittal) translation of the jig relative to the lower femur, or axial twisting (rotation) clockwise or counterclockwise is strongly resisted by friction. Stated differently, when the jig is properly positioned on the femur such that the jig contact points are touching the respective femoral contact points, the jig is firmly held on the femur through the intercooperation of the jig contact points to the femoral contact points. While it is possible, that a small number of the jig contact points, e.g., one or two, may not actually touch the femur due to actual femoral inconsistencies relative to the images of the femur, the jig will nonetheless be held in position.

More specifically and as illustrated in FIG. 1011, which is an axial representative view of the distal region of the femur and the jig contact surfaces and associated points, there are six contact points (JCP1-JCP6) constrained against posterior movement. The shape of the trochlear groove and condyles where JCP1-JCP6 contact the femur cooperatively constrain the jig from posterior movement. Similarly, there are six contact points (JCP7-JCP12) constrained against anterior movement. The shape of the condyles where JCP7-JCP12 contact the femur cooperatively constrain the jig from anterior movement. Further, CP1-CP6 cooperate with CP7-CP12 to constrain the jig from any form of anterior or posterior movement or rotation over the femur, by cooperatively opposing both posterior and anterior movement, respectively.

The jig is also held against rotational movement in the axial plane or twisting or canting off the sagittal plane. For perspective, if the femoral head above and adjacent the intercondylar fossa is considered along the axis of the femur, or relatively close, the contact points JCP1, JCP3 and JCP5 cooperate with JCP8, JCP10, and JCP12 to oppose rotational forces in the counterclockwise direction with the axis as reference. Similarly, the contact points JCP2, JCP4, and JCP6 cooperate with JCP7, JCP9 and JCP11 to oppose rotational forces in the clockwise direction with the axis as reference.

Referring primarily to FIG. 1011, and discussing relative relationships between jig contact points anteriorly to posteriorly, it can be seen that the jig contact points JCP1, JCP2, JCP3 and JCP4 may be substantially coplanar in a coronal plane. Similarly, jig contact points JCP5 and JCP6 may be define a plane substantially parallel to the plane of JCP1-JCP3, JCP7 and JCP8 may define a plane substantially parallel with the place of JCP5 and JCP6, and JP9, JCP10, JCP11, and JCP12 may be substantially coplanar. As shown, the contact points defining planes or when defining planes are parallel, may lie in the same plane with possibly some deviation based on manufacturing tolerances or the like, and the defined planes may not be parallel also depending on manufacturing tolerances. The points, however, do not necessarily lie in a common transverse plane due to the contact point anatomies at the points. In some implementation, the contact points may be considered coplanar but be anterior or posterior (sagittally offset from illustrated) to a common plane by 2 millimeters. Of course, depending on patient anatomy, manufacturing efficiency, design considerations or the like, contact points may not be coplanar as described, and the planes may deviate from parallel based on optimal point positioning due to patient anatomy, joint degradation, MRI image quality and the like.

As illustrated, the contact points JCP1-JCP4, may be separated from JCP5, JCP6 by between about 15 millimeters (a range of 12-18 millimeters being typical). The contact points JCP5 and JCP6 are posteriorly relative to JCP1-JCP4. The contact points JCP5 and JCP6 may be separated from JCP7 and JCP8 by about 14 millimeters (a range of 11-17 millimeters being typical). The contact points JCP7 and JCP8 posterior relative to JCP5 and JCP6. The contact points JCP9-JCP12 may be separated from JCP7 and JCP8 be about 10 millimeters (a range of 7 to 13 millimeters being typical). The contact points JCP9-JCP12 are posterior relative to JCP7 and JCP8. The dimensions are from a sagittal plane to a sagittal plane, measured transversely (posteriorly) with reference to the orientation and arrangement illustrated in FIG. 1011.

While the jig implementation illustrated includes 12 jig contact points, it is possible to provide a jig with slightly more or slightly less contact points. For example, JCP3 and JCP4 might be eliminated. In another example, JCP3 and JCP4 and/or JCP5 and JCP6 might be eliminated. In another example, JCP8 and JCP7 might be eliminated. In another example, JCP3 and JCP4, and/or JCP5 and JCP6, and JCP7 and JCP8 might be eliminated.

Additionally, it is possible to move the various points anteriorly or posteriorly relative to the positions indicated. Such movement may depend on damage to the knee being replaced, shape of the trochlear groove, shape of one or both condyles, the size of the femur, and the type of procedure being performed.

A tibial cutting jig 20 conforming with various aspects of the present disclosure includes a substrate from which various jig contact points (JCPm) project, are otherwise supported or defined. In one possible implementation, the jig 20 is a unified structure formed from a block of base material using a computer numerical control (CNC) machine. However, it is possible for the jig to be an assembly of various components to form the final cutting jig structure. Alternatively, the jig may be created through molding, machining, milling, forming, 3D printing, assembling, or other processes. The term "substrate" as used herein is meant to refer to a base structure upon which the various jig contact points and jig contact point supporting structures are provided or otherwise supported, and by which the relative positioning of the various jig contact points are maintained. As mentioned, the jig may be a unified structure and hence the substrate and jig contact points are formed from the same material and thus the relative positioning of the jig contact points is naturally maintained. Other processes, such as milling a base material or forming a jig in a mold, would provide a similar unified structure. It is not necessary, however, that the jig be unified structure in which case the substrate may be a frame or other structure or assembly on which various jig contact point defining structures are attached or otherwise associated.

The jig contact points are arranged and spaced such that a surgeon may press the jig onto the proximal surface of the tibia and the jig will be properly positioned when the jig contact points are seated on respective tibial contact points (TCPm). Notably, there are a discrete number of jig contact points (e.g., 5-8) as opposed to full surfaces or far more numerous numbers of contact locations. The jig also includes a cutting guide support structure onto which the cutting guide 31 may be mounted. When the jig 20 is seated on the tibia 10, the jig may be pinned to the tibia and properly position the cutting guide so that a resection of the tibia may be performed pursuant to a total knee replacement, for example.

Figure 201A:
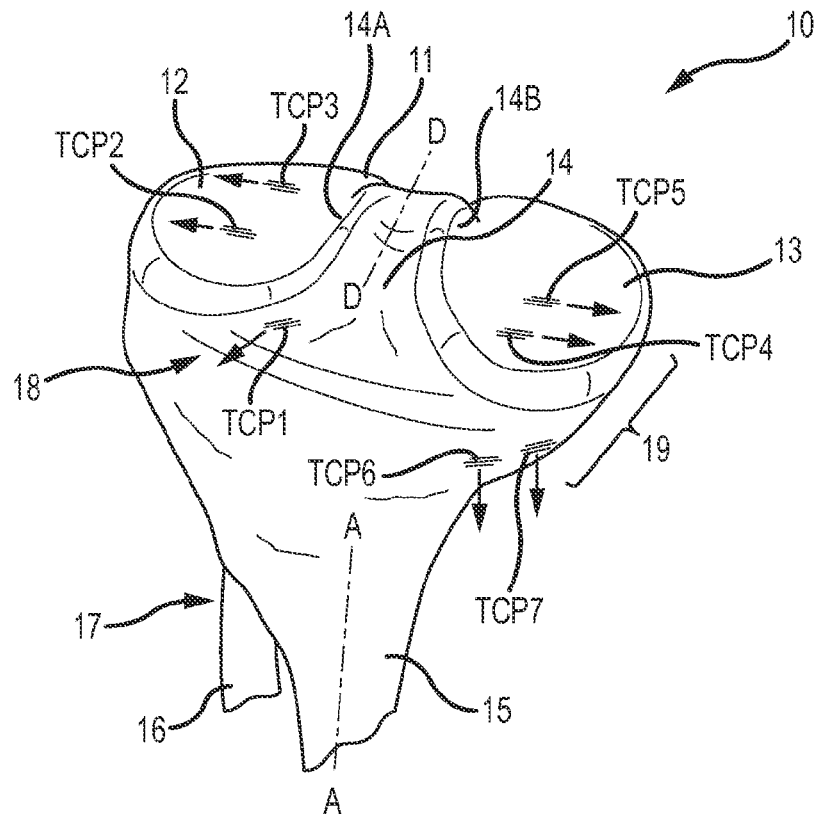
FIGS. 201A and 201B are isometric views of a proximal portion of a tibia (right knee), indicating tibia contact points for a tibia cutting jig mechanism.
Figure 201B:
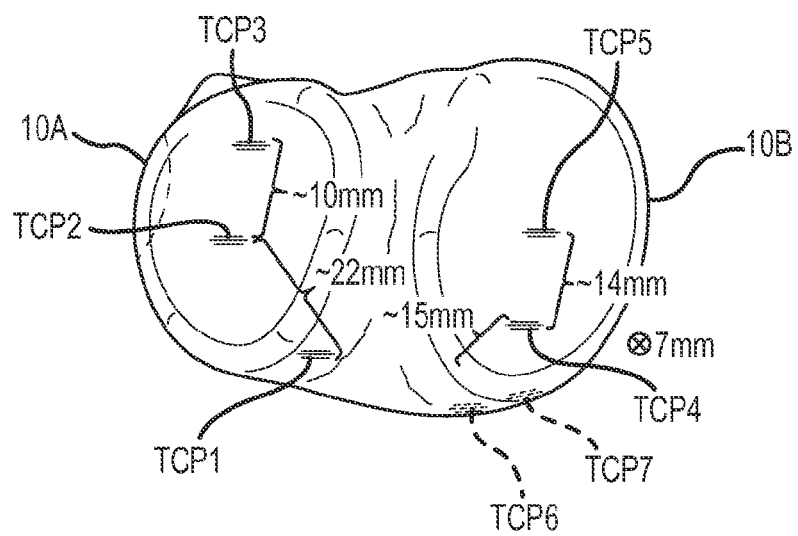

The tibia plateau 11 at a proximal surface of the tibia 10, shown in FIGS. 201A and 201B, includes a concave first region 12, a second region 13, which may be concave (depressed), be partly or wholly "flat," or be convex, spaced apart from the first region 12. As shown, both the first and second region, which may also be referred to as the superior articular surfaces of the lateral 10A and medial 10B tibial condyles, respectively, are both slightly concave. The tibial spine 14, lying between intercondylar tubercles (14A, 14B), with an associated spine direction D-D, is located between and spaced apart from the first region 12 and the second region 13. The tibia shaft 15 extends downward (distally) along a tibia axis A-A from the tibia plateau 11. The fibula 16, which provides stability for the tibia, is connected at its proximal end 17 to the tibia 10 at the articular facet, which is near but below the tibia plateau 11 on the lateral condyle. Several tibia contact points, TCPm (m=1, 2, M; M≅7) are identified in FIGS. 201A and 201B on or near the tibia plateau 11, in the first region 12 (m=1, 2)), in the second region (m=3, 4), and in a third region 18 adjacent to and anterior from the spine 14 (m=5) in an intercondylar area at the anterior of the tibia plateau. One or two other tibia contact points (m=6, 7) are identified on an upper surface of the tibia shank 15, approximately 1 cm below the tibia plateau 11, and on the medial tibial condyle 10B. Additional contact points may be included but would not contribute substantially to stability of the tibia cutting jig mechanism 20, when fitted against the tibia 10.

Figure 202A:
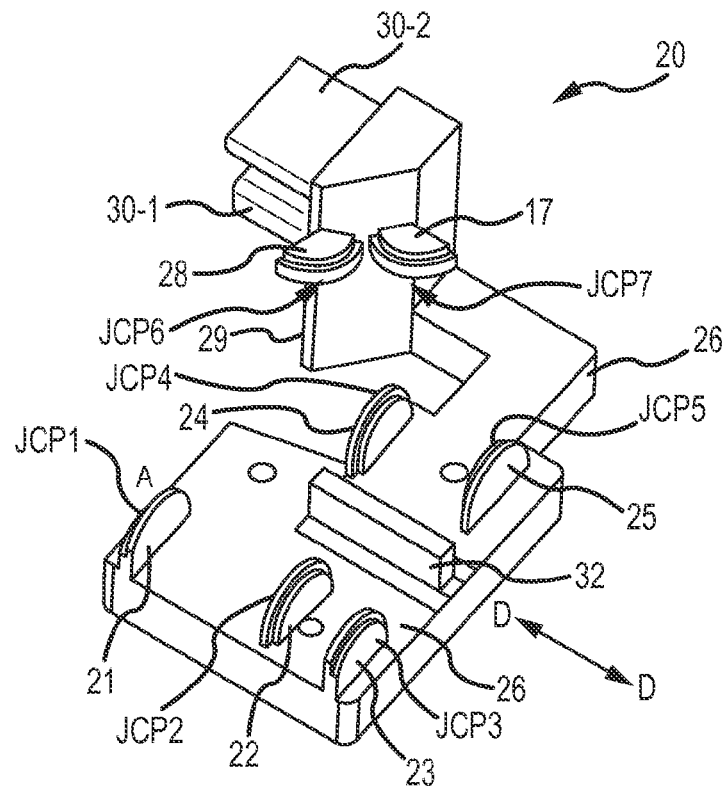
FIGS. 202A and 202B are isometric views of a tibia cutting jig mechanism (TCJM), indicating jig contact points that correspond to the tibia contact points in FIGS. 201A and 201B.
Figure 202B:
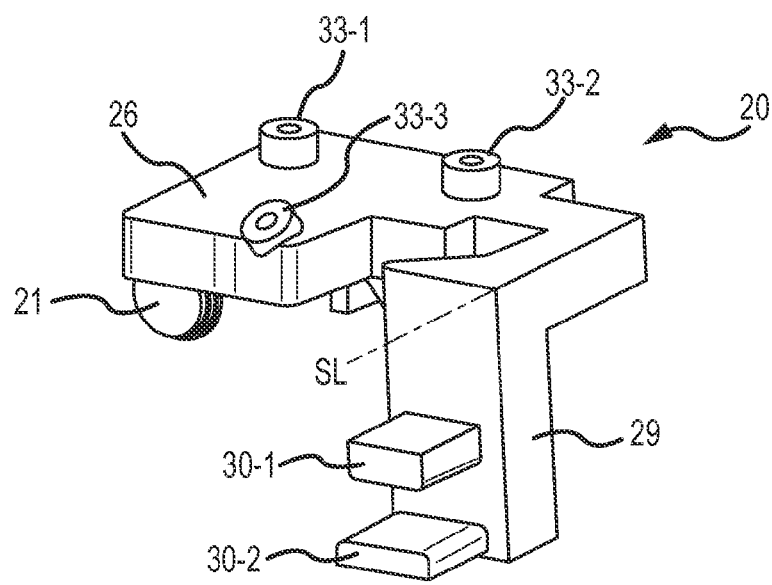
Figure 203A:
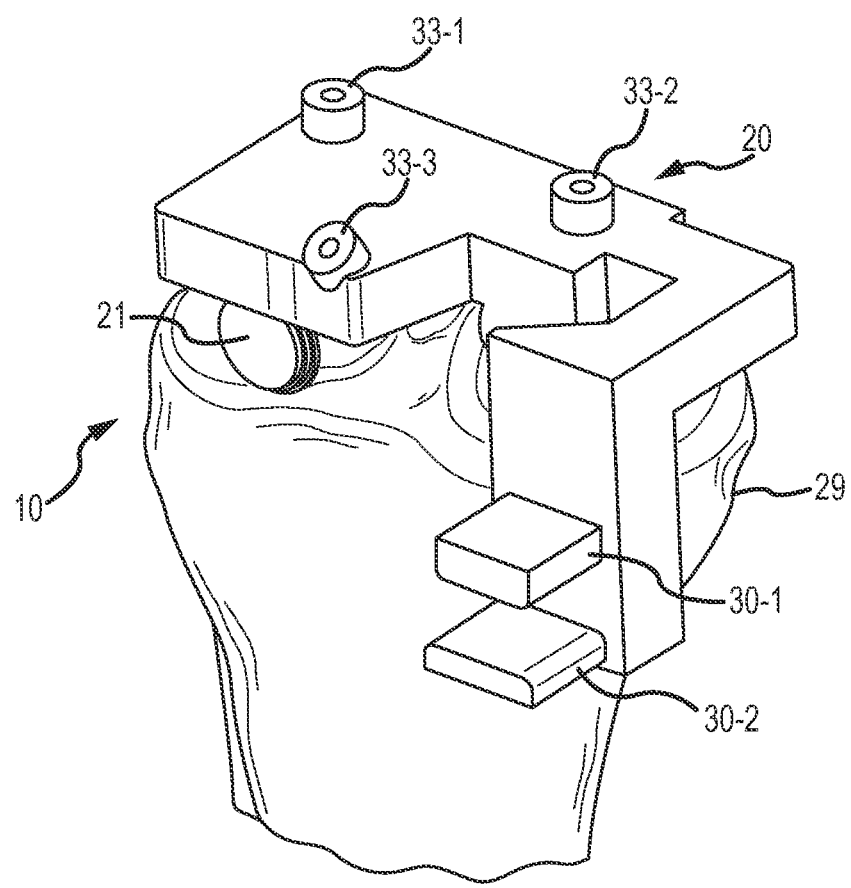
FIGS. 203A-203C and 203E are views of a tibia with a jig pressed thereon.
Figure 203B:
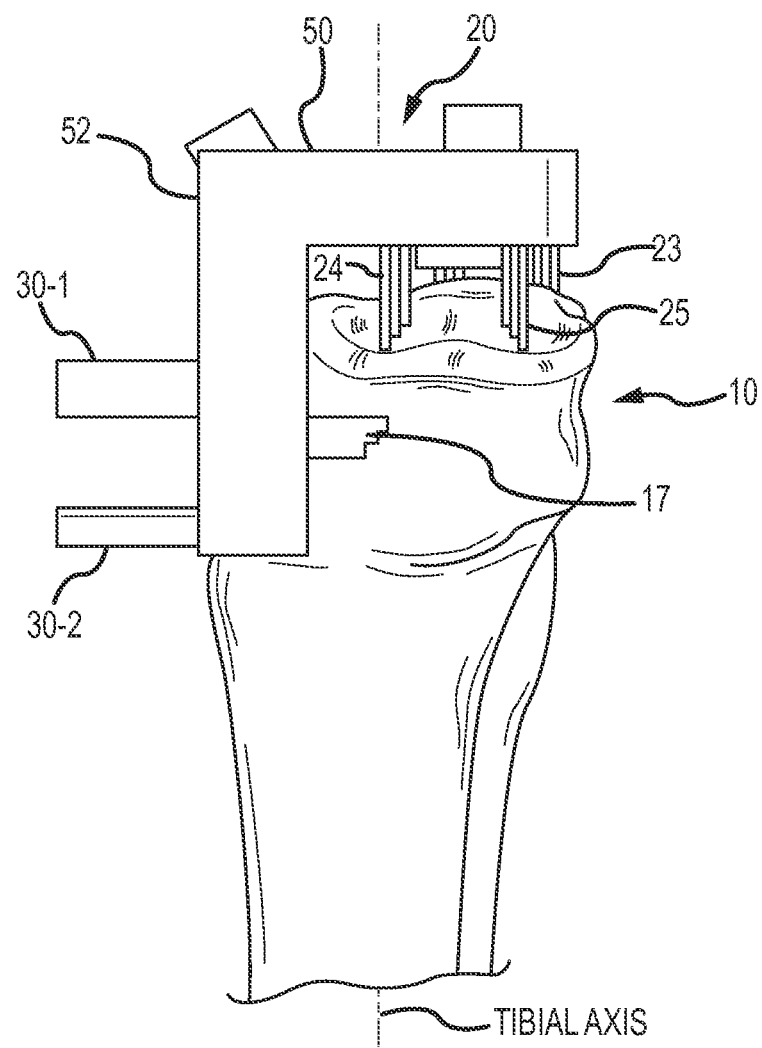
Figure 203C:
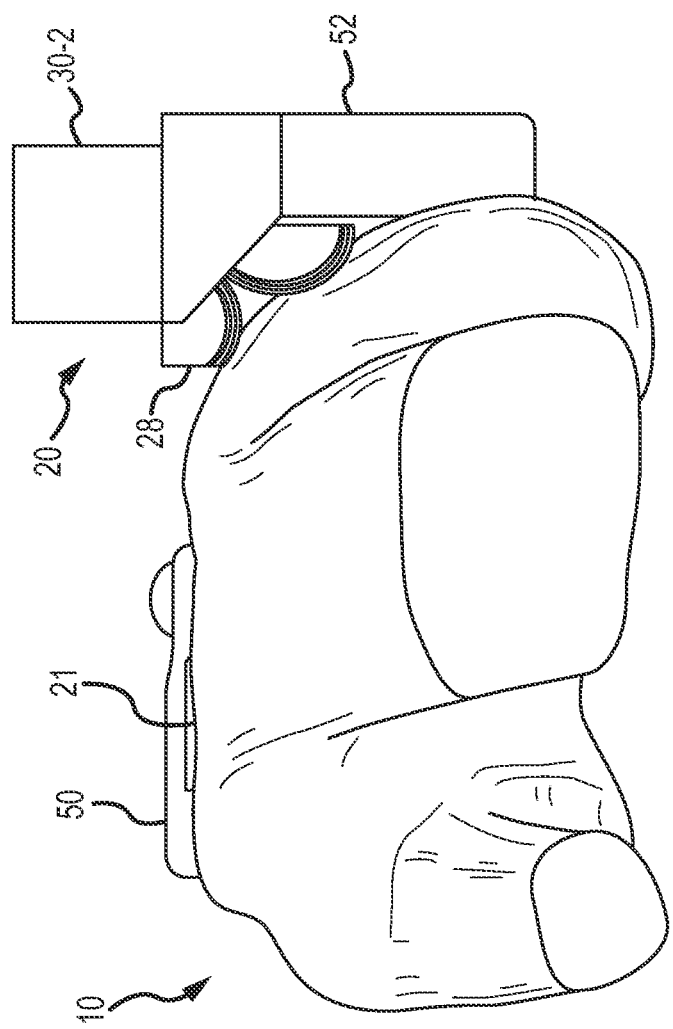

FIGS. 202A and 202B are isometric views of an embodiment of the jig 20, and FIGS. 203A-203F are various views of the jig in relation to the tibia 10. The jig includes a first substrate portion 50 and a second substrate portion 52 generally perpendicular to the first substrate portion. As can be seen in FIG. 203B and elsewhere, the first substrate portion 50 is generally transverse to the tibial axis A-A of the tibia (substantially in the axial plane when mounted) and the second substrate portion 52 is generally perpendicular to the first substrate portion. It should be noted that the jig positions the cut plane bar 31, and hence the jig position on the tibia will vary based on the anatomy of the patient, the type of procedure, the type of prosthetic, and any number of other factors. Hence, the anatomical relationships described are illustrative and not limiting. Further, the jig structure illustrated is a convenience of manufacturing, with the jig originally formed from a block of material and machined away to form the resulting structures. Thus, it is not necessary that the first substrate portion be perpendicular to the second portion, for example. It is possible to machine these structures more or less so long as the resulting jig contact points are formed, and there are not obstructions to positioning the jig on the tibia properly. Moreover, different shapes (besides the partial circles shown) may be used to form the surfaces providing the jig contact points.

Figure 203D:
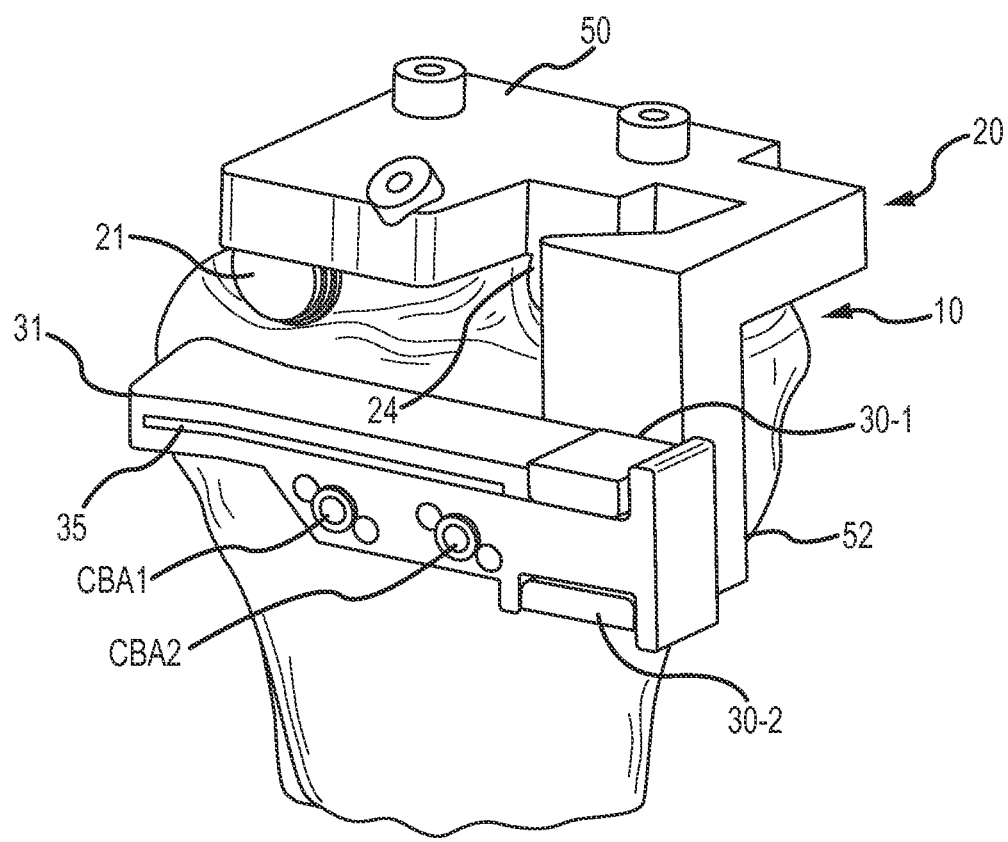
FIG. 203D is a view of the jig pressed on the tibia and with a cut plane guide on the jig.
Figure 203E:
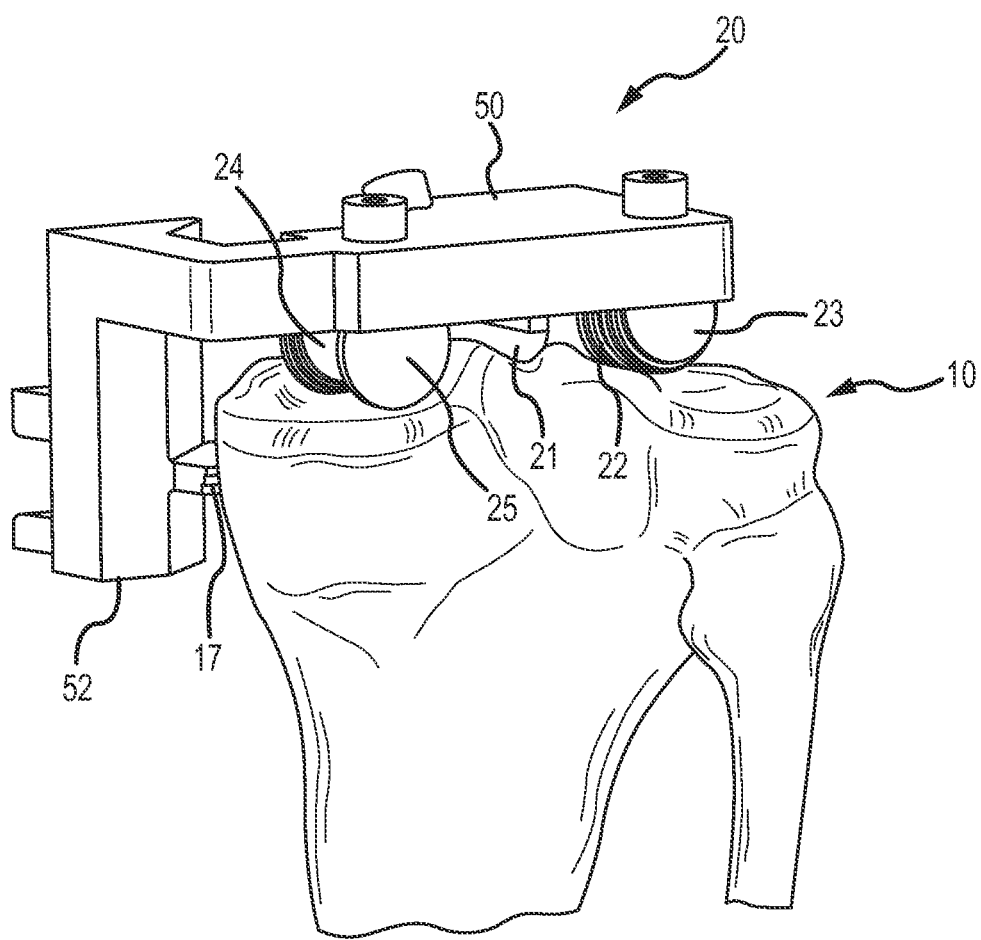

Five curvilinear surfaces, 21, 22, 23, 24, 25, project from a first substrate surface 26 of the jig 20 to provide jig contact points, JCPm (m=1, 2, . . . , 5) corresponding to the respective tibia contact points, TCPm (m=1, 2, . . . , 5) (FIGS. 201A-201B). One or two additional jig contact points JCPm (m=6, 7) are provided by curvilinear surfaces, 27 and 28, which correspond to the respective tibia contact points TCP6 and TCP7. It is possible to use fewer contact points on the tibia surface, and to use one or no contact points below the surface, or to use an additional point or two below the surface. In the implementation shown, the curvilinear surfaces are in the form of sectors (partial circles with a radius). The surfaces 27 and 28 project from a vertically oriented polygonal structure 29 defined by the second substrate portion 52. The polygonal structure 29 provides regions of attachment support for the first and second, spaced projecting plates, 30-1 and 30-2, that define the cut plane guide support for the cut guide 31 (FIG. 203D). While two plates are shown, one plate may suffice and other forms of members may also serve as features whereby a cut plane support is mounted. The placement of the surfaces and respective contact points JCP6 and JCP7 provide stability when the CPG 31 is being pinned to the bone due to the position of the contact points TCP6, TCP7 on the jig contact points JCP6, JCP7 formed by projections 28 and 29 from the second substrate and facing the bone.

As shown, some of the curvilinear surfaces are formed of a plurality of curvilinear surfaces (e.g., sectors) arranged proximate each other and forming radial steps of increasing (or decreasing) radiuses depending on perspective. The collection of radial steps of any given projection provides greater structural integrity of the projection due to the thickness of the projection. The contact point for any given projection, however, may be defined along only one of the radial steps and preferably the largest radius step in the example jig implementation shown here. Moreover, it is possible to provide a larger projection, without any steps, one or more steps of differing thicknesses, depending on the particular contact point being defined as well as the contour and surface shape of the tibia at the tibial contact point for the corresponding jig contact point. The use of steps, however, helps ensure that any of the contact points touch the bone while also maintaining structural support for the projection due to the increasing thickness at and below the steps.

A linear sight projection 32, projecting from the substrate surface 26 and located between the jig contact points, JCP1, JCP2 and JCP3, and the jig contact points, JCP4 and JCP5, serves to align itself with the spine direction D-D defined by the spine aperture (FIG. 201A) when the jig is properly positioned on the tibia. Hence, a surgeon may use the sight 32 to visually align the jig relative to the intercondylar tubercles 14A, 14B and the spine 14 therebetween. In the specific jig shown, the central vertical projection, as well as other features discussed herein, may be formed by tooling elements, such as from a CNC machine router bits. Adjacent the projection and in the space between the surfaces 21, 22, 23, 24 and 25, material may be removed to allow a surgeon to see past the vertical projection to where the points along the various curvilinear surfaces contact the respective tibial contact points as discussed herein.

FIGS. 204A through 204I illustrate two dimensional, linear and curvilinear formats that can be used in embodiments to construct tangent lines and other approximation elements (FIG. 204J) used in obtaining relevant dimensions of the upper tibia and corresponding tibia cutting jig mechanism 20 shown in the various figures. Referring first to FIG. 204J, a portion of an MRI slice is illustrated. The MRI slice shows a line 54 denoting a boundary of the tibia, where a tibia contact point 56 is located and where a corresponding jig contact point 58 is defined, which will contact the tibia at the tibia contact point. The tibia portion illustrated may be cortical bone, cancellous bone cartilage at a boundary to open space or otherwise. Since each such material may have its own range of grey scales in the MRI image, the boundary line is merely representative of a contact area, which may not be in fact a discrete line. The tibia contact area of the MRI may be a slice through all or a portion of either or both condyles, the shank, or other regions of the proximal area of the tibia and particularly the tibia plateau relevant to a total knee replacement procedure or other tibial procedure that may take advantage of the jig described herein.

In the view illustrated in FIG. 204J, a portion of a coronal plane MRI slice of the proximal tibia is illustrated. More specifically, the boundary line 54 represents a coronal plane MRI slice of the lateral condyle encompassing the tibia contact point 56. In order to define a jig contact point, various lines and geometrical shapes may be deployed. The curve, $y=f(x)$ shown in an example in FIG. 204J is assumed to be continuously differentiable in an interval $a<x<b$, and to have a well-defined tangent line slope 60, $dy/dx=df/dx$, at a point, $(x, y)=(x0, y0)$. For example, three spaced apart, noncollinear coordinate pairs, $(xm, ym)$ ($m=1, 2, 3$) can be used to determine an optimal circle (center and radius) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the tibia contact area of interest. In the case of a circular contact point-defining structure or other structures, the structure may be made to intersect or touch the tibia contact area of interest at and with coinciding tangent lines.

Figure 204A:
FIGS. 204A-204I illustrate one- and two-dimensional, closed and open, linear and curvilinear formats that can be used to construct tangent lines and other linear and curvilinear approximation elements used in obtaining relevant dimensions for surfaces defining jig contact points in different embodiments of the invention, illustrated in one example in FIG. 204J.

In the case of FIG. 204A, a rectangle is used to define the jig contact point at the corresponding femoral contact point. The line defined by the MRI slice encompassing the femoral contact point is characterized by a curve, $y=f(x)$, which is assumed to be continuously differentiable in an interval $a \leq x \leq D$, and to have a well-defined tangent line slope, $dy/dx=df/dx$, at a point, $(x, y)=(x0, y0)$. For example, three spaced apart, noncollinear coordinate pairs, $(xm, ym)$ ($m=1, 2, 3$) can be used to determine an optimal rectangle (length and width) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a rectangular contact point defining structure or other structures, the structure may be made to intersect or touch the femoral contact area of interest at and with coinciding tangent lines.

Figure 204B:

In the case of FIG. 204B, a line segment is used to define the jig contact point at the corresponding femoral contact point. The line defined by the MRI slice encompassing the femoral contact point is characterized by a curve, y=f(x), which is assumed to be continuously differentiable in an interval a≤x≤D, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal line (length) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a linear contact point defining structure or other structures, the structure may be made to intersect or touch the femoral contact area of interest at and with coinciding tangent lines.

Figure 204C:

In the case of FIG. 204C, a circle is used to define the jig contact point at the corresponding femoral contact point. The line defined by the MRI slice encompassing the femoral contact point is characterized by a curve, y=f(x), which is assumed to be continuously differentiable in an interval a≤x≤D, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal circle (center and radius) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a circular contact point defining structure or other structures, the structure may be made to intersect or touch the femoral contact area of interest at and with coinciding tangent lines.

Figure 204D:

In the case of FIG. 204D, an ellipse is used to define the jig contact point at the corresponding femoral contact point. The line defined by the MRI slice encompassing the femoral contact point is characterized by a curve, y=f(x), which is assumed to be continuously differentiable in an interval a≤x≤D, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal ellipse (center and radius) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of an elliptical contact point defining structure or other structures, the structure may be made to intersect or touch the femoral contact area of interest at and with coinciding tangent lines.

Figure 204E:

In the case of FIG. 204E, a triangle is used to define the jig contact point at the corresponding femoral contact point. The line defined by the MRI slice encompassing the femoral contact point is characterized by a curve, y=f(x), which is assumed to be continuously differentiable in an interval a≤x≤D, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal triangle (base and height) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a triangular contact point defining structure or other structures, the structure may be made to intersect or touch the femoral contact area of interest at and with coinciding tangent lines.

Figure 204F:

In the case of FIG. 204F, a trapezoid is used to define the jig contact point at the corresponding femoral contact point. The line defined by the MRI slice encompassing the femoral contact point is characterized by a curve, y=f(x), which is assumed to be continuously differentiable in an interval a≤x≤D, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal trapezoid (base and height) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a trapezoidal contact point defining structure or other structures, the structure may be made to intersect or touch the femoral contact area of interest at and with coinciding tangent lines.

Figure 204G:

In the case of FIG. 204G, a parallelogram is used to define the jig contact point at the corresponding femoral contact point. The line defined by the MRI slice encompassing the femoral contact point is characterized by a curve, y=f(x), which is assumed to be continuously differentiable in an interval a≤x≤D, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal parallelogram (base and height) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a parallelogram contact point defining structure or other structures, the structure may be made to intersect or touch the femoral contact area of interest at and with coinciding tangent lines.

Figure 204H:

In the case of FIG. 204H, a quadratic curve is used to define the jig contact point at the corresponding femoral contact point. The line defined by the MRI slice encompassing the femoral contact point is characterized by a curve, y=f(x), which is assumed to be continuously differentiable in an interval a≤x≤D, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal quadratic curve (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a quadratic curve contact point defining structure or other structures, the structure may be made to intersect or touch the femoral contact area of interest at and with coinciding tangent lines.

Figure 204I:
Figure 204J:
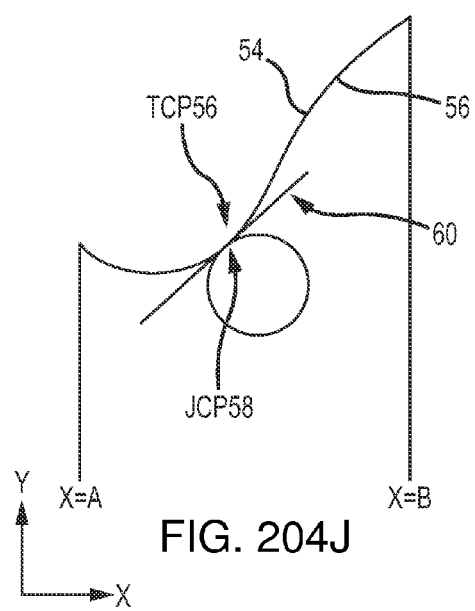

In the case of FIG. 204I, a cubic curve is used to define the jig contact point at the corresponding femoral contact point. The line defined by the MRI slice encompassing the femoral contact point is characterized by a curve, y=f(x), which is assumed to be continuously differentiable in an interval $a \leq x \leq D$, and to have a well-defined tangent line slope, $dy/dx=df/dx$, at a point, $(x, y)=(x0, y0)$. For example, three spaced apart, noncollinear coordinate pairs, (xm, ym) (m=1, 2, 3) can be used to determine an optimal cubic curve (1) that is coincident with the curve, $y=f(x)$, at each of the locations (xm, ym) or (2) that has the same tangent line slope as the function $y=f(x)$ at one or more of the locations (ym, ym). In general, a jig contact point may be defined at a point or region along the curve $y=f(x)$ defining the femoral contact area of interest. In the case of a cubic curve contact point defining structure or other structures, the structure may be made to intersect or touch the femoral contact area of interest at and with coinciding tangent lines.

Depending on the implementation, it may be preferable that no corner point, such as a jig contact point, be sharp or otherwise have a high degree of sharpness such as is often associated with a true "point". Rather, a contact point may have an associated point segment that is at least about 0.3 mm in actual size or larger up to and including a line, in one possible implementation. The incorporation of this constraint will help ensure that, for example, a jig contact point will have adequate frictional contact such that the contact point will not slip or otherwise move relative to a region on the tibia, but at the same time the contact point will not penetrate or pierce any soft tissue on the portion of the tibia being contacted and hence possibly distort the fit of the jig to the tibia. It is less of a concern about damaging the tibia as the portion of the tibia being contacted is likely to be removed (resected) and replaced with a prosthetic implant. Notably, where a straight line segment from a square, rectangle, triangle or trapezoid is used as the contact point defining structure, and a corner of such structure is not the contact point, the area along the straight line segment at which contact is made, is considered a contact point. Moreover, in such an implementation, the straight line segment may have a rounded or otherwise non-knife edge cross section, particularly at the area where the surface is intended to contact the femur.

Figure 203F:
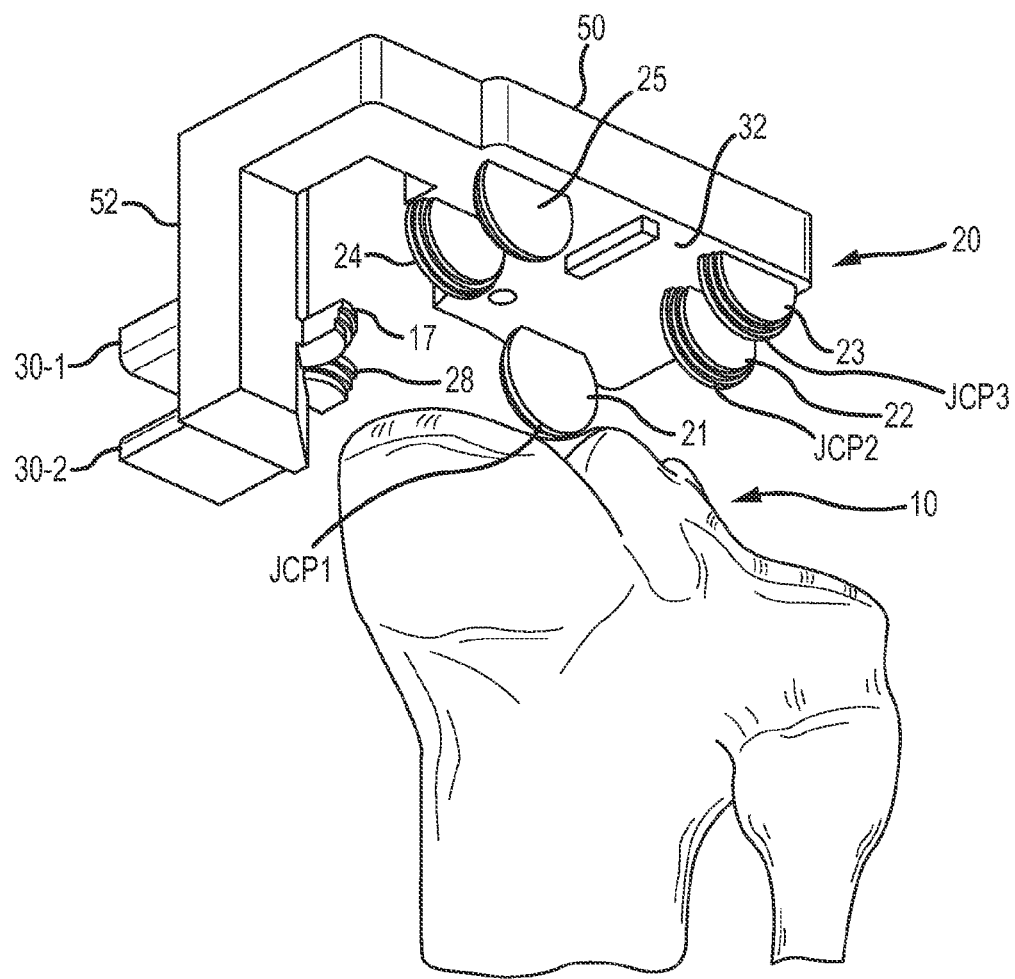
FIG. 203F is a view of the jig proximate but above the tibia.
Figure 205:
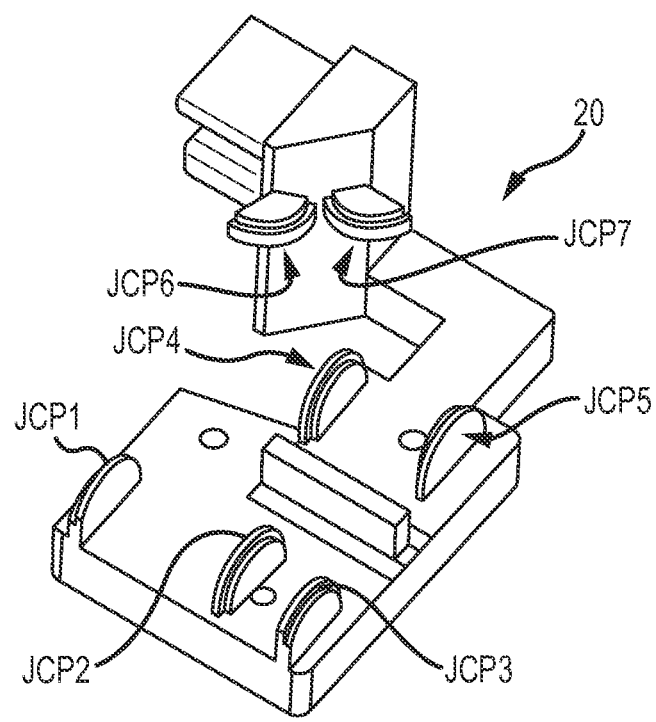
FIG. 205 is an isometric and schematic view indicating suitable locations of a jig defining jig contact points according to an embodiment.

FIGS. 205 and 203F illustrate suitable locations of jig contact points, JCP1, JCP2 and JCP3, for the jig 20, spaced apart by separation distances of approximately 1 cm (JCP2 to JCP3) and 2 cm (JCP1 to JCP2). With respect to JCP2 and JCP3, the separation may be in range, such as between 7 mm and 13 mm, depending on the dimension of the particular tibia to which the jig is built. As shown in this embodiment, the jig contact point JCP2 is located between the jig contact points JCP1 and JCP3 and is closer to the jig contact point JCP3. The three jig contact points JCP1, JCP2 and JCP3 are located on the curvilinear projections 21, 22 and 23 (FIG. 202A), respectively, which are substantially parallel to each other. The various curvilinear projection are shown parallel but they may, of course, be substantially parallel and may vary from parallelism due to manufacturing tolerance, design differences, and the like. Thus, to be substantially parallel, the projections may vary from true parallel by 1-10 degrees. Similarly, design preference or functionality, may dictate that the projections not be parallel where shown. For example, in some instances, the projections may be substantially perpendicular from the movement constricting feature to which the projections are positioned. For example, for contact points JCP2 and JCP3, the respective curvilinear projections may be positioned substantially perpendicular to the slope of the adjacent articular surface that restricts medial movement of the jig. Also, with a larger or smaller sized tibia, or differently spaced and/or shaped condyles and/or surfaces, the contact points may be more or less separated. Moreover, the contact points may be arranged, laterally, medially, anteriorly and/or posteriorly to other locations or as illustrated in the figures. As with other surfaces, projections and the likely structure illustrated is a convenience of manufacturing, with the jig originally formed from a block of material and machined away to form the resulting jig contact points JCP1, JCP2 and JCP3.

In the implementation shown, the curvilinear surfaces 21, 22, and 23 each comprise a plurality of semi-circular portions, each of slightly differing radius (lesser radius). The same situation is also present with the surfaces 24 and 25, and 17 and 28. In each case, the largest radius portion provides the jig contact point and the adjacent portions (steps) of lesser radius enhance the structural integrity of the projection but are not meant to contact the tibia, although some unintended contact is possible. Accordingly, the decreasing radius portions are positioned on the side of the projection best suited to not interfere with the tibia or the jig contact point. For example, with respect to surfaces 24 and 25, the decreasing radius portions of each surface face each respective surface. The tibia in the area where the jig contacts the tibia at tibia contacts points TCP4 and TCP5, however, is concave. Accordingly, the radiuses do not track the slope of the tibia in the contact area, but instead are counter to the slope, thereby minimizing the likelihood of inadvertent contact. In contrast, if the decreasing radius portions were placed on the opposite sides shown, the decreasing radiuses would be similar to the upward slope of the tibia in these areas and while they may not contact the tibia, the decreasing radiuses would have less of a distance and thus more possibly contact the tibia.

FIGS. 205, 203B and 203F, and others illustrate suitable locations of jig contact points, JCP4 and JCP5, for the jig 20, spaced apart by a separation distance of approximately 1 cm (or in a range of 7 mm to 13 mm, although others ranges are possible), as shown. The two jig contact points, JCP4 and JCP5, are located on the curvilinear sector projections 24 and 25 (FIG. 2A), respectively, which are substantially parallel to each other. Each of the jig contact points, JCP1, JCP2, JCP3, JCP4 and JCP5, can move in one direction in a plane of the tibia plateau 11 (indicated by arrows in FIG. 1A) but cannot move in an opposite direction (see FIG. 6) because of presence of solid features that are part of the topography of the tibia plateau 11. With a larger or smaller sized tibia or differently spaced and/or shaped condyles and/or articular surfaces, the contact points may be more or less separated. Moreover, the contact points may be arranged, laterally, medially, anteriorly and/or posteriorly to where illustrated.

The curvilinear projections illustrated may define sectors with the contact point defined along the edge of the sector. In the implementation illustrated, the projections extend from the substrate as discrete planar elements with the surface intended to contact the tibia defining the sector. As discussed, the edge may define a stepped structure in one possible example. Moreover, the edge may define a relatively narrow flat edge so as not to define a sharp edge. Other suitable shapes may be used to define the contact points. For example, a conical projection with the contact point defined as the tip area of the cone may extend from the substrate. In another example, a post may extend from the substrate, with the tip area of the post defining the jig contact point. The tip may be rounded, flat, beveled, etc. Other planar shapes, such as those illustrated in FIGS. 4A-41, may also be used, with an edge of the planar shape including the contact point.

FIGS. 205, 206, 203B, 203C, and 203E illustrate suitable locations of jig contact points, JCP6 and JCP7, for the jig 20, spaced apart by a separation distance of approximately 1 cm, as shown (measured from the respective contact points). The two jig contact points, JCP6 and JCP7, are located on the curvilinear sector projections 28 and 27 (FIG. 202A), respectively, and are substantially coplanar. Each of the jig contact points, JCP6 and JCP7, can move downward (indicated by arrows in FIG. 201A) along the tibia shank axis A-A, but cannot move upward because of presence of a solid object, the upper portion 19 of the tibia, when the jig is properly positioned with points JCP6 and JCP7 contacting the tibia at TCP6 and TCP7.

The contact points JCP1, JCP2, JCP3, JCP4 and JCP5 are associated with features of the tibia plateau 11, and the jig contact points JCP6 and JCP7 are associated with features of the shaft. One goal of the contact points on the jig 20 is to provide an optimal position of the jig in contact with the proximal tibia, for which lateral rotation (posterior to anterior, or anterior to posterior) of the jig relative to the tibia, or longitudinal (sagittal) translation of the jig relative to the tibia, or axial twisting (rotation) clockwise or counterclockwise, is resisted by friction caused by contact between the jig and the tibia at the contact point. Stated differently, when the jig is properly positioned on the tibia such that the jig contact points are touching the respective tibial contact points and firmly seated there by a surgeon, the jig is firmly held in the correct orientation on the tibia through the interoperation of the jig contact points to the tibia contact points. While it is possible that a small number of the jig contact points, e.g., one or two, may not actually touch the tibia due to actual tibial inconsistencies relative to the images of the tibia, the jig will nonetheless be held in position.

Figure 206:
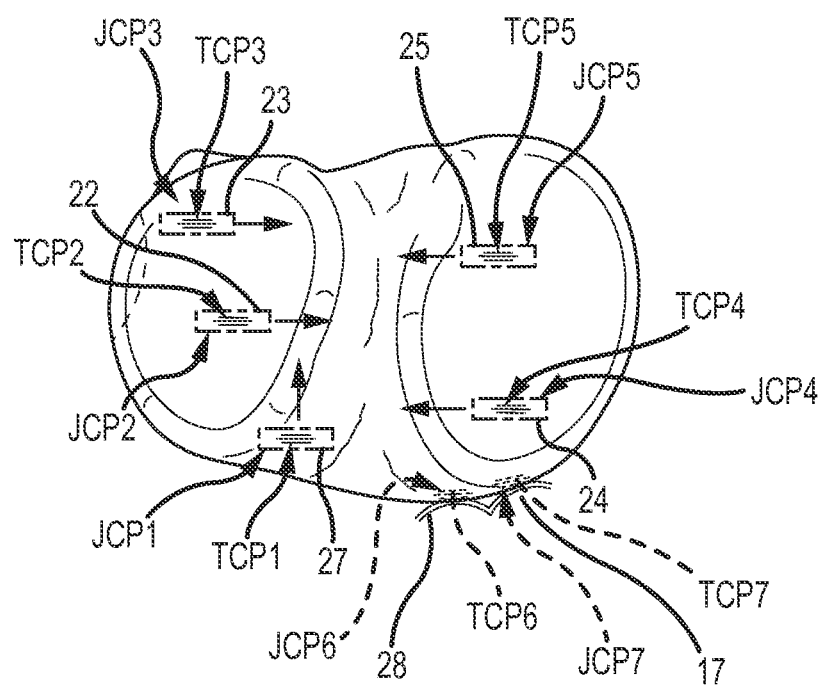
FIG. 206 is a top representative view of a proximal portion of the tibia indicating examples of tibia contact points and also illustrating jig features and jig contact points to hold the jig in the proper orientation.

As illustrated in FIGS. 201A, 201B, and 206, contact points (JCP2 and JCP3) are constrained from medial movement by the slope of the articular surface adjacent the lateral intercondylar tubercle 14A. Similarly, contact points (JCP4 and JCP5) are constrained from lateral movement by the slope of the articular surface adjacent the medial intercondylar tubercle 14B. The contact point that is most anterior, JCP1, is constrained from posterior movement by the distally sloping anterior wall of the tibia adjacent to the tubercles 14A, 14B. Finally, contact points TCP6 and TCP7 help to hold the jig against the plateau 11 by butting against the inwardly sloping wall 19 of the medial condyle 10B, and thus trapping the jig from proximal movement (away from the tibia along the axis A-A). Some or all of the points work in harmony, once the jig is properly seated on the tibia, to hold the jig in place and properly align the jig in order to pin the cut plane guide.

Although the jig implementation illustrated includes seven (7) jig contact points, it is possible to provide a jig with slightly more or slightly fewer contact points. For example, JCP2 and JCP3 might be eliminated, and replaced with a contact point lying therebetween, and perhaps with a larger cross section, while still abutting the articular surface adjacent to the lateral intercondylar tubercle 14A. In another example, JCP1 may be eliminated. In yet another example, JCP4 and JCP5 may be eliminated, and replaced with a contact point lying therebetween, and perhaps with a larger cross section, while still abutting the articular surface adjacent to the medial intercondylar tubercle 14B. In another example, JCP2 and/or JCP4 may be eliminated. While the jig implementation illustrated includes seven jig contact points, it is possible to provide a jig with slightly more or slightly less contact points. For example, JCP2 might be eliminated. In another example, JCP1 may be shifted medially, and JCP4 eliminated. Additionally, it is possible to move the various points anteriorly or posteriorly relative to the positions indicated. Such movement may depend on damage to the knee being replaced, shape of the trochlear groove, shape of one or both condyles, the size of the tibia, and the type of procedure being performed.

Additionally, it is possible to move the various contact points anteriorly, posteriorly, laterally and/or medially relative to the positions indicated. Such movement may depend on damage to the knee being replaced, shape of the trochlear groove, shape of one or both condyles, the size of the tibia, and the type of procedure being performed. Additionally, one of more points may be defined below the tibial plateau at different locations than TCP 6 and TCP 7. For example, points may be positioned to engage the anterior surface, below the plateau, of the lateral tibial condyle.

Providing a different perspective as illustrated in FIG. 206, which is an axial representative view of the proximal region of the tibia and the jig contact surfaces and associated points, the movement constraints are shown with symbols (arrows encircled) illustrating the constraining directions. FIG. 201A, in contrast, illustrates arrows oriented in the direction where the surfaces are unconstrained where the opposite direction (and possibly other directions) is constrained. There are three contact points (JCP1, JCP6 and JCP7) constrained against posterior movement. In some instances, JCP3 and JCP5 may also be constrained against posterior movement by the superior articular surfaces of the respective condyles at TCP3 and TCP5. Similarly, there are one or two contact points (JCP2 and JCP4) constrained against anterior movement by the superior articular surfaces of the respective condyles at TCP2 and TCP4. Further, some or all of the contact points intercooperate to constrain the jig from any form of anterior or posterior movement or rotation over the tibia, by cooperatively opposing both posterior and anterior movement, respectively.

The jig is also held against rotational movement in the axial plane or twisting or canting off the sagittal plane. For perspective, if the tibial plateau region generally between the tubercles is considered along the axis of the tibia, or relatively close, the contact points JCP1 and JCP2 cooperate with JCP4 to oppose rotational forces in the clockwise direction with the axis as reference. Similarly, the contact point JCP5 cooperates with JCP1 to oppose rotational forces in the counter clockwise direction with the axis as reference. JCP6 and JCP7 also work in conjunction with the other contact points to help prohibit rotation, and to prevent the jig from rotating off the tibia coronally.

Referring primarily to FIG. 206, JCP2 is posteriorly offset from JCP1 by about 22 millimeters (a range of 19-25 millimeters being typical) and JCP4 is posteriorly offset from JCP1 by about 15 millimeters (a range of 12 to 28 millimeters being typical). The measurement being transversely (posteriorly) between a sagittal plane defined through each respective point rather than directly from point to point. Using the same technique, JCP5 is posteriorly offset from JCP4 by about 13 millimeters (a range of 10 to 16 millimeters being typical). JCP3 is posteriorly offset from JCP2 by about 10 millimeters (a range of 7 to 13 millimeters) being typical. In contrast, JCP6 and JCP7 are measured a common transverse plane to a common transverse plane of JCP4 (the most proximate contact point in the implementation shown) and is offset by about 7 millimeters (a range of 4 to 10 millimeters being typical).

The various features discussed and shown herein are but one way to create a jig defining the various jig contact points of interest. In the example shown, the CNC machine tool bits and other cutting mechanisms influence the jig shapes. The various surfaces and jig features, on which the jig contact points are defined, are thus defined in part by requirements of the CNC machine. If the jig were formed in another way, such as through 3D printing, molding, and the like, the jig contact point features and overall jig shape may be different than illustrated although the position and relative location of the jig contact points, depending on the patient, would be substantially the same regardless of the jig manufacturing technique employed.

The embodiment shown contemplates a cut plane guide that is separately pinned to the femur so that the jig may be removed prior to resection. This embodiment contemplates the jig being of possibly different material (e.g., a surgical grade polymer) rather than stainless steel or the like. It is possible, however, to fabricate the cutting guide into the body of the jig and form a unified structure where the entirety of the jig is pinned to the femur and stays in place during the resectioning procedure. It is also possible, depending on the material used for the jig, to place a liner within the cut slot of the cutting guide, where the liner is stainless steel such that the saw will not cut the slot during the back and forth sawing action. It is also possible for the slot to be integrated in the jig directly, in which case the cut plane guide will be a part of the jig.

The embodiment discussed above contemplates the use of pins to secure the jig and the cutting plane guide in place. It is possible, however, to use other forms of anchors such as screws or combinations of screws and pins. It is also possible, in the case of pins, to use some relatively small (smaller than threads of a screw) of some form of abrasive surface—e.g., annular ridges, roughing, or the like along some or all of the pin shaft, to ensure the pins stay in place and therefore holds the respective jig and/or cutting plane guide in place. Moreover, the jig is shown as defining a plurality of apertures, along with respective bosses, to receive such anchors. It is possible, however, to have the apertures defined in separate structures attached to or otherwise associate with the jig or to secure the jig to the femur in some other way, or to simply hold it in place while the cut plane guide is secured to the femur.

It should be noted that the flowcharts above are illustrative only. Alternative embodiments of the present invention may add operations, omit operations, or change the order of operations without affecting the spirit and scope of the present invention. The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

I claim:

1. A method for creating a cutting jig for an arthroplasty procedure, the method comprising: receiving a plurality of two-dimensional images of a patient's joint the subject of the arthroplasty procedure; reformatting the two-dimensional images to approximate a true anatomical coordinate of the patient's joint; locating a plurality of mating shapes within the reformatted plurality of two-dimensional images of the patient's joint, the plurality of mating shapes corresponding to a plurality of mating shapes of a cutting jig for use during the arthroplasty procedure; generating a milling program based at least on the placement of the mating shapes within the reformatted plurality of two-dimensional images of the patient's joint; and milling the cutting jig based at least on the milling program, wherein locating the plurality of mating shapes within the reformatted plurality of two-dimensional images comprises indicating a position of a first circular mating shape of a femoral portion of the cutting jig such that the first circular mating shape of the femoral portion contacts at least one femoral condyle within an anterior trochlear groove of the patient's joint as illustrated in a first one of the plurality of two-dimensional images of the patient's joint.

2. The method of claim 1 further comprising:
generating the plurality of two-dimensional images of a patient's joint the subject of the arthroplasty procedure utilizing a magnetic-resonance imaging machine.

3. The method of claim 1 wherein reformatting the two-dimensional images comprises:
identifying one or more landmarks on the plurality of two-dimensional images of a patient's joint; and
reorienting the plurality of two-dimensional images of a patient's joint based at least on the one or more landmarks.

4. The method of claim 1 wherein locating the plurality of mating shapes within the reformatted plurality of two-dimensional images further comprises:
indicating a position of a first portion of a trapezoidal mating shape of the femoral portion of the cutting jig such that the first portion of a trapezoidal mating shape tangentially contacts an inner surface of a first condyle of the patient's joint as illustrated in a second one of the plurality of two-dimensional images of the patient's joint; and
indicating a position of a second portion of a trapezoidal mating shape of the femoral portion of the cutting jig such that the second portion of a trapezoidal mating shape tangentially contacts an inner surface of a second condyle of the patient's joint as illustrated in the second one of the plurality of two-dimensional images of the patient's joint.

5. The method of claim 4 wherein locating the plurality of mating shapes within the reformatted plurality of two-dimensional images further comprises:
indicating a position of a second circular mating shape of the femoral portion of the cutting jig such that the second circular mating shape of the femoral portion contacts at least the first condyle of the patient's joint as illustrated in a third one of the plurality of two-dimensional images of the patient's joint, the contact of the second circular mating shape of the femoral portion posterior of the position of the first circular mating shape of the femoral portion; and
indicating a position of a third circular mating shape of the femoral portion of the cutting jig such that the third circular mating shape of the femoral portion contacts at least the second condyle of the patient's joint as illustrated in the third one of the plurality of two-dimensional images of the patient's joint, the contact of the third circular mating shape of the femoral portion also posterior of the position of the first circular mating shape of the femoral portion.

6. The method of claim 5 wherein locating the plurality of mating shapes within the reformatted plurality of two-dimensional images further comprises indicating a position of a fourth circular mating shape of the femoral portion of the cutting jig such that the fourth circular mating shape of the femoral portion contacts at least one femoral condyle within a middle portion of the trochlear groove of the patient's joint as illustrated in a fourth one of the plurality of two-dimensional images of the patient's joint, the middle portion of the trochlear groove located between the contact of the first circular mating shape of the femoral portion and the second circular mating shape of the femoral portion along the trochlear groove of the patient's joint as illustrated in a fourth one of the plurality of two-dimensional images of the patient's joint.

7. The method of claim 6 wherein locating the plurality of mating shapes within the reformatted plurality of two-dimensional images further comprises indicating a position of a first circular mating shape of a tibial portion of the cutting jig and a second circular mating shape of the tibial portion of the cutting jig such that the first circular mating shape of the tibial portion and the second circular mating shape of the tibial portion contact the tibial anterior surface of the patient's joint as illustrated in a fifth one of the plurality of two-dimensional images of the patient's joint.

8. The method of claim 7 wherein locating the plurality of mating shapes within the reformatted plurality of two-dimensional images further comprises:
  indicating a position of a third circular mating shape of the tibial portion of the cutting jig such that the third circular mating shape of the tibial portion contacts a medial tibial plateau surface of the patient's joint as illustrated in a sixth one of the plurality of two-dimensional images of the patient's joint; and
  indicating a position of a fourth circular mating shape of the tibial portion of the cutting jig such that the fourth circular mating shape of the tibial portion contacts a lateral tibial plateau surface of the patient's joint as illustrated in a seventh one of the plurality of two-dimensional images of the patient's joint.

9. The method of claim 8 wherein locating the plurality of mating shapes within the reformatted plurality of two-dimensional images further comprises:
  indicating a position of a fifth circular mating shape of the tibial portion of the cutting jig such that the fifth circular mating shape of the tibial portion contacts a medial tibial plateau surface of the patient's joint as illustrated in an eighth one of the plurality of two-dimensional images of the patient's joint, the contact of the fifth circular mating shape of the tibial portion being posterior of the position of the third circular mating shape of the tibial portion; and
  indicating a position of a sixth circular mating shape of the tibial portion of the cutting jig such that the sixth circular mating shape of the tibial portion contacts a lateral tibial plateau surface of the patient's joint as illustrated in a ninth one of the plurality of two-dimensional images of the patient's joint, the contact of the sixth circular mating shape of the tibial portion being posterior of the position of the fourth circular mating shape of the tibial portion.

10. The method of claim 9 wherein locating the plurality of mating shapes within the reformatted plurality of two-dimensional images further comprises indicating a position of a seventh circular mating shape of the tibial portion of the cutting jig such that the seventh circular mating shape of the tibial portion contacts the lateral tibial plateau surface of the patient's joint as illustrated in a tenth one of the plurality of two-dimensional images of the patient's joint, the contact of the seventh circular mating shape of the tibial portion being between the contact of the fourth circular mating shape of the tibial portion and the sixth circular mating shape of the tibial portion on the lateral tibial plateau surface of the patient's joint as illustrated in the tenth one of the plurality of two-dimensional images of the patient's joint.

* * * * *